United States Patent
Cusack et al.

(10) Patent No.: US 11,767,310 B2
(45) Date of Patent: Sep. 26, 2023

(54) NICOTINAMIDE RIPK1 INHIBITORS

(71) Applicant: AbbVie Inc., North Chicago, IL (US)

(72) Inventors: Kevin Patrick Cusack, Worcester, MA (US); Michael Zeller Hoemann, Worcester, MA (US); David Andrew Kinsman, Worcester, MA (US); Sami Osman, Worcester, MA (US); James Patrick Stambuli, Worcester, MA (US); Maria Anastasia Argiriadi, Worcester, MA (US); Ciaran O'Reilly, Nottingham (GB); Hannah Dexter, Nottingham (GB); Euan Fordyce, Nottingham (GB); Steve St. Gallay, Nottingham (GB)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 17/882,709

(22) Filed: Aug. 8, 2022

(65) Prior Publication Data

US 2023/0127127 A1 Apr. 27, 2023

Related U.S. Application Data

(60) Provisional application No. 63/231,590, filed on Aug. 10, 2021.

(51) Int. Cl.
| | |
|---|---|
| *C07D 401/06* | (2006.01) |
| *A61P 1/04* | (2006.01) |
| *C07D 405/14* | (2006.01) |
| *C07D 413/06* | (2006.01) |
| *C07D 417/06* | (2006.01) |
| *C07D 498/04* | (2006.01) |

(52) U.S. Cl.
CPC .............. *C07D 401/06* (2013.01); *A61P 1/04* (2018.01); *C07D 405/14* (2013.01); *C07D 413/06* (2013.01); *C07D 417/06* (2013.01); *C07D 498/04* (2013.01)

(58) Field of Classification Search
CPC .. C07D 401/06; C07D 405/06; C07D 413/06; C07D 417/06; A61K 31/455
See application file for complete search history.

(56) References Cited

U.S. PATENT DOCUMENTS

| | | | |
|---|---|---|---|
| 6,218,387 B1 | 4/2001 | Wehner et al. | |
| 6,723,727 B1 | 4/2004 | Peyman et al. | |
| 2021/0284647 A1 | 9/2021 | Li et al. | |

FOREIGN PATENT DOCUMENTS

| | | |
|---|---|---|
| WO | WO-1997/05131 A1 | 2/1997 |
| WO | WO-2005/018547 A2 | 3/2005 |
| WO | WO-2005/019206 A1 | 3/2005 |
| WO | WO-2007/019205 A2 | 2/2007 |
| WO | WO-2007/094513 A2 | 8/2007 |
| WO | WO-2009/038759 A2 | 3/2009 |
| WO | WO-2009/117269 A1 | 9/2009 |
| WO | WO-2010/120935 A1 | 10/2010 |
| WO | WO-2011/113707 A1 | 9/2011 |
| WO | WO-2012/052167 A1 | 4/2012 |
| WO | WO-2013/049255 A1 | 4/2013 |
| WO | WO-2014/125444 A1 | 8/2014 |
| WO | WO-2015/100322 A1 | 7/2015 |
| WO | WO-2016/017831 A1 | 2/2016 |
| WO | WO-2016/017980 A1 | 2/2016 |
| WO | WO-2016/027253 A1 | 2/2016 |
| WO | WO-2016/101885 A1 | 6/2016 |
| WO | WO-2016/185423 A1 | 11/2016 |
| WO | WO-2017/004500 A1 | 1/2017 |
| WO | WO-2017/069279 A1 | 4/2017 |
| WO | WO-2017/096301 A1 | 6/2017 |
| WO | WO-2017/109724 A1 | 6/2017 |
| WO | WO-2017/136727 A2 | 8/2017 |
| WO | WO-2018/058148 A1 | 3/2018 |
| WO | WO-2018/148626 A1 | 8/2018 |
| WO | WO-2019/02562 A1 | 1/2019 |
| WO | WO-2019/213447 A1 | 11/2019 |
| WO | WO-2020/149553 A1 | 7/2020 |
| WO | WO-2023/018643 A1 | 2/2023 |

OTHER PUBLICATIONS

International Search Report and Written Opinion for International Application No. PCT/US22/39689 dated Nov. 4, 2022.
Berge et al., "Pharmaceutical Salts," Journal of Pharmaceutical Sciences 66(1): pp. 1-19 (1977).
CAS Registry No. 2060781-34-0 ; STN Entry Date Jan. 29, 2017.
CAS Registry No. 2061618-31-1 ; STN Entry Date Jan. 30, 2017.
CAS Registry No. 2068885-45-8 ; STN Entry Date Feb. 10, 2017.
CAS Registry No. 2069213-06-3 ; STN Entry Date Feb. 10, 2017.
CAS Registry No. 2069238-03-3 ; STN Entry Date Feb. 10, 2017.
CAS Registry No. 2069428-45-9 ; STN Entry Date Feb. 12, 2017.
CAS Registry No. 2069471-29-8 ; STN Entry Date Feb. 12, 2017.
CAS Registry No. 2069767-25-3 ; STN Entry Date Feb. 13, 2017.
CAS Registry No. 2069803-76-3 ; STN Entry Date Feb. 13, 2017.
CAS Registry No. 2070869-45-1 ; STN Entry Date Feb. 14, 2017.

(Continued)

*Primary Examiner* — Deepak R Rao
(74) *Attorney, Agent, or Firm* — Foley Hoag LLP; Hathaway P. Russell; Laura A. Wzorek

(57) ABSTRACT

Provided herein are compounds of Formula (I) and pharmaceutically acceptable salts thereof, useful as RIPK1 inhibitors, and pharmaceutical compositions comprising same. Further provided are methods of use and preparation. Also provided are methods of treating Ulcerative Colitis using a compound of Formula (I).

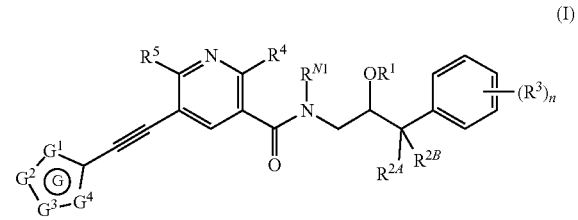

8 Claims, 3 Drawing Sheets

(56) References Cited

OTHER PUBLICATIONS

CAS Registry No. 2071826-53-2 ; STN Entry Date Feb. 17, 2017.
CAS Registry No. 2071984-97-7 ; STN Entry Date Feb. 17, 2017.
CAS Registry No. 2072208-99-0 ; STN Entry Date Feb. 19, 2017.
CAS Registry No. 2072345-45-8 ; STN Entry Date Feb. 19, 2017.
CAS Registry No. 2072658-66-1 ; STN Entry Date Feb. 20, 2017.
CAS Registry No. 2072840-17-4 ; STN Entry Date Feb. 20, 2017.
CAS Registry No. 2419717-96-5 ; STN Entry Date Jun. 5, 2020.
Haynes et al., "Occurrence of Pharmaceutically Acceptable Anions and Cations in the Cambridge Structural Database," Journal of Pharmaceutical Sciences 94(10): 9 pages (2005).
Najjar et al., "Structure guided design of potent and selective ponatinib-based hybrid inhibitors for RIPK1", *Cell reports* 10(11): 1850-1860 (2015).
Takahashi et al., "Structural Optimization of ghrelin receptor inverse agonists to improve lipophilicity and avoid mechanism-based CYP3A4 inactivation", *Chemical and Pharmaceutical Bulletin* 63(10): 825-832 (2015).
Wang et al., "Identification of nicotinamide aminonaphthyridine compounds as potent RET kinase inhibitors and antitumor activities against RET rearranged lung adenocarcinoma", Bioorganic chemistry 90: 103052 (2019).

NICOTINAMIDE RIPK1 INHIBITORS

RELATED APPLICATION

This application claims the benefit of priority to U.S. Provisional Patent Application No. 63/231,590, filed Aug. 10, 2021, the contents of which are hereby incorporated by reference.

BACKGROUND

Receptor-interacting protein kinase (RIPK1) is a key regulator of inflammation involved in the induction of necroptosis, apoptosis, and pro-inflammatory cytokine production. Necroptosis is a pro-inflammatory form of regulated cell death characterized by breakdown of the cellular membrane and the release of intracellular contents into the local cellular environment. The intracellular contents, known as damage associated molecular patterns (DAMPs), activate various immune cells leading to the onset of an inflammatory response and the production of inflammatory cytokines that contribute to additional cell death, thus driving a cycle of inflammation. The most studied pathway for induction of necroptosis by RIPK1 is the tumor necrosis factor (TNF) pathway, but RIPK1 is also involved in necroptosis induction by other TNF superfamily members (FAS/TRAIL) and Toll-like receptors (TLRs; TLR3/TLR4). Phosphorylation of RIPK1 leads to subsequent phosphorylation of RIPK3 and formation of an amyloid structure that subsequently recruits and activates the pseudokinase MLKL (mixed lineage kinase domain-like), a critical component of necroptotic cell death. Inhibition of RIPK1 is associated with inhibition of this necroptotic induced cascade of events and the ensuing inflammatory response. See, e.g., Li, et al., Necroptosis in inflammatory bowel disease and other intestinal diseases. *World J. Clin. Cases* (2018) 6(14):745-752. Accordingly, there exists a need to develop further inhibitors of RIPK1 useful for treating Ulcerative Colitis.

SUMMARY

Described herein are compounds of Formula (I), and pharmaceutically acceptable salts thereof:

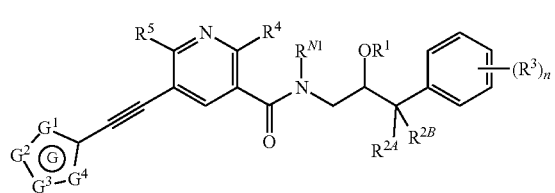

(I)

wherein:
$R^1$ is hydrogen, or
$R^1$ is $-P(=O)(OR^{P1})_2$, $-C(=O)CH_2OR^{P1}$, $-C(=O)CH_2N(R^{P1})_2$, or $-C(=O)R^{P2}$, wherein each instance of $R^{P1}$ is independently selected from the group consisting of hydrogen and substituted or unsubstituted $C_{1-4}$alkyl, and $R^{P2}$ is substituted or unsubstituted $C_{1-4}$alkyl;
$R^{2A}$ and $R^{2B}$ are each independently hydrogen or halo;
each $R^3$ is independently selected from the group consisting of halo and substituted or unsubstituted $C_{1-4}$alkyl, wherein n is 0, 1, or 2;
$R^{N1}$ is hydrogen or substituted or unsubstituted $C_{1-4}$alkyl;
$R^4$ is independently selected from the group consisting of hydrogen, $-OR^{4A}$, and substituted or unsubstituted $C_{1-4}$alkyl, wherein $R^{4A}$ is hydrogen or substituted or unsubstituted $C_{1-4}$alkyl;
$R^5$ is independently selected from the group consisting of hydrogen, $-OR^{5A}$, and substituted or unsubstituted $C_{1-4}$alkyl, wherein $R^{5A}$ is hydrogen or substituted or unsubstituted $C_{1-4}$alkyl;
Ring G is a 5-membered heteroaryl ring, wherein each $G^1$, $G^2$, $G^3$, and $G^4$ is, independently, CH, $CR^{G1}$, N, $NR^{N2}$, O, or S, provided at least one of $G^1$, $G^2$, $G^3$, and $G^4$ is N, $NR^{N2}$, O, or S, and wherein no more than two of $G^1$, $G^2$, $G^3$, and $G^4$ is O or S;
each instance of $R^{G1}$ is independently selected from the group consisting of halo, $-OR^{G2}$, $-NR^7$, substituted or unsubstituted $C_{1-4}$alkyl, substituted or unsubstituted 3-4-membered carbocyclyl, or substituted or unsubstituted 4-membered heterocyclyl, wherein $R^{G2}$ is hydrogen or substituted or unsubstituted $C_{1-4}$alkyl;
or two vicinal $R^{G1}$ groups, taken together with the atoms to which they are attached, form a fused substituted or unsubstituted 5-6 membered carbocyclyl or fused substituted or unsubstituted 5-6 membered heterocyclyl;
or a vicinal $R^{G1}$ group and $R^{N2}$ group, taken together with the atoms to which they are attached, form a fused substituted or unsubstituted 5-6 membered heterocyclyl;
each $R^{N2}$ is independently selected from the group consisting of hydrogen, substituted or unsubstituted $C_{1-4}$alkyl, substituted or unsubstituted 3-4-membered carbocyclyl, and substituted or unsubstituted 4-membered heterocyclyl;
each $R^7$ is independently selected from the group consisting of hydrogen, substituted or unsubstituted $C_{1-4}$alkyl, substituted or unsubstituted 3-4-membered carbocyclyl, and substituted or unsubstituted 4-membered heterocyclyl; and
each instance of substituted or unsubstituted is optionally and independently substituted by 0, 1, 2, or 3 substituents selected from the group consisting of halo, $-OH$, $-O(C_{1-4}$alkyl), and $-O(C_{1-4}$haloalkyl).

In certain embodiments, in Ring G, at least one of $G^1$, $G^2$, $G^3$, and $G^4$ is N or $NR^{N2}$.

In certain embodiments, in Ring G, at least one of $G^2$ or $G^3$ is N or $NR^{N2}$.

In certain embodiments, in Ring G, at least two of $G^1$, $G^2$, $G^3$, and $G^4$ are N or $NR^{N2}$.

In certain embodiments, Ring G is a diazole. In certain such embodiments, $G^2$ and $G^3$ are each independently N or $NR^{N2}$.

In further embodiments, Ring G is a triazole. In certain such embodiments, $G^2$, $G^3$, and $G^4$ are each independently N or $NR^{N2}$.

In certain embodiments, $R^{N2}$ is alkyl or haloalkyl.

In certain embodiments, one of $G^1$ and $G^2$ is $CR^{G1}$. In certain such embodiments, $R^{G1}$ is methyl or cyclopropyl.

In certain embodiments, $R^4$ is hydrogen.

In certain embodiments, $R^5$ is hydrogen, alkoxy, or haloalkyl.

In further embodiments, $R^5$ is hydrogen, methyl, methoxy, or difluoromethyl. In still further embodiments, $R^5$ is hydrogen.

In certain embodiments, $R^{N1}$ is hydrogen or methyl. For example, in some embodiments, $R^{N1}$ is hydrogen; alternatively, in some embodiments, $R^{N1}$ is methyl.

In certain embodiments, $R^{2A}$ and $R^{2B}$ are each hydrogen.

In certain embodiments, one of $R^{2A}$ and $R^{2B}$ is hydrogen and the other is fluoro.

In certain embodiments, n is 0 or 1.

In certain embodiments, n is 1. In certain such embodiments, $R^3$ is halo.

In alternative embodiments, n is 0.

In certain embodiments, $R^1$ is hydrogen.

In alternative embodiments, $R^1$ is —P(=O)(OR$^{P1}$)$_2$, —C(=O)CH$_2$N(R$^{P1}$)$_2$, or —C(=O)R$^{P2}$. For example, $R^1$ is —P(=O)(OR$^{P1}$)$_2$. In certain such embodiments, each $R^{P1}$ is independently selected from the group consisting of hydrogen and unsubstituted $C_{1-4}$alkyl. In further such embodiments, each $R^{P1}$ is hydrogen. Alternatively, each $R^{P1}$ can be unsubstituted $C_{1-4}$alkyl.

In certain embodiments, the compound is selected from the following table:

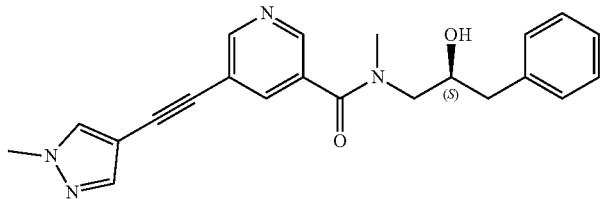

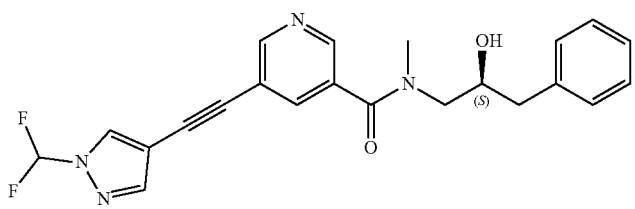

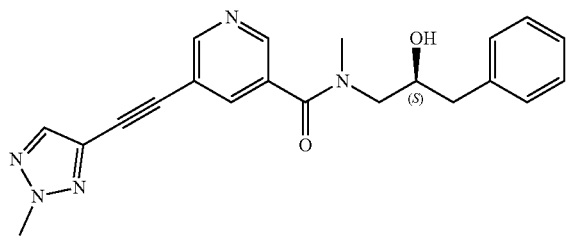

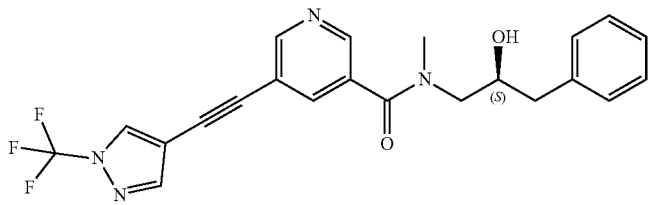

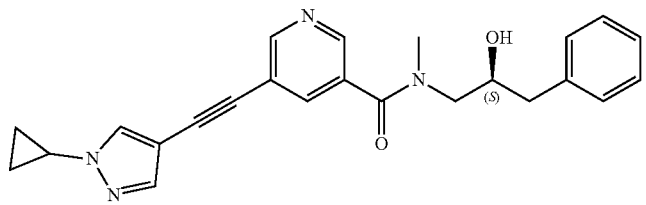

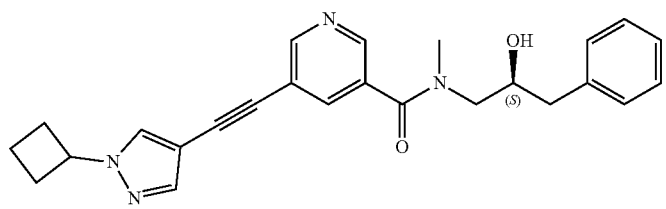

-continued
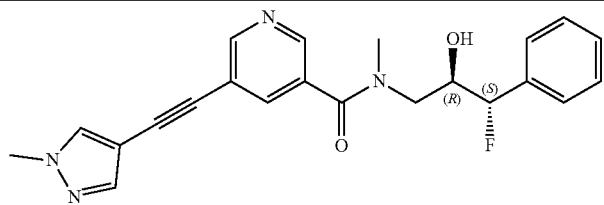
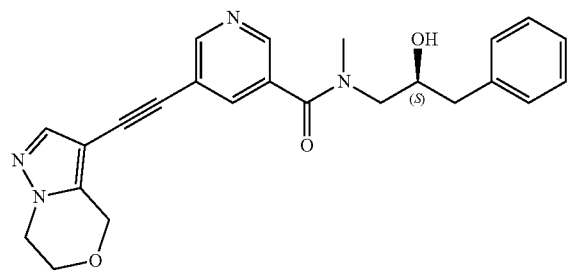
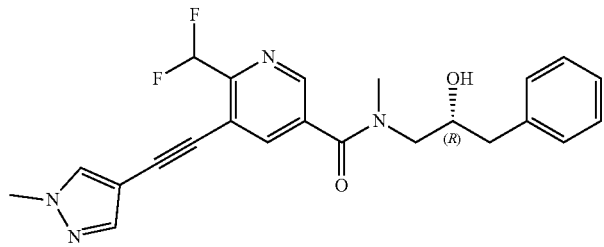
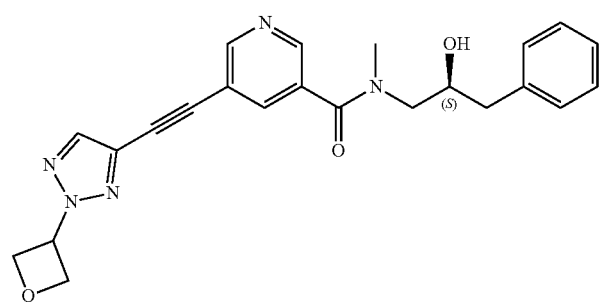
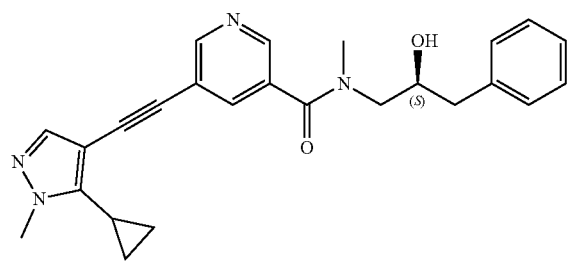
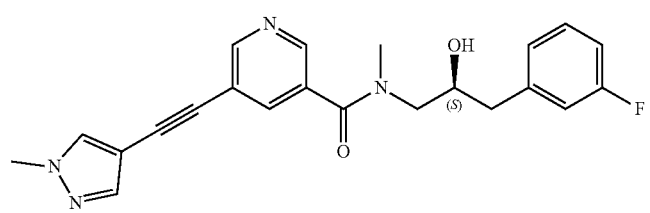

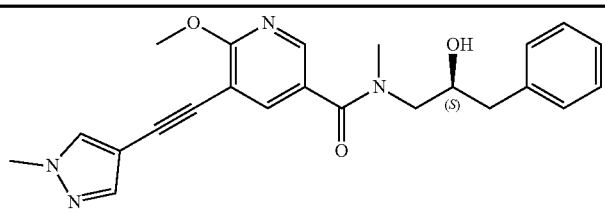
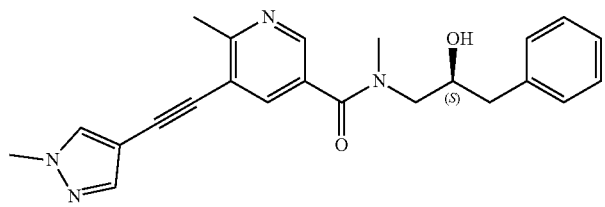
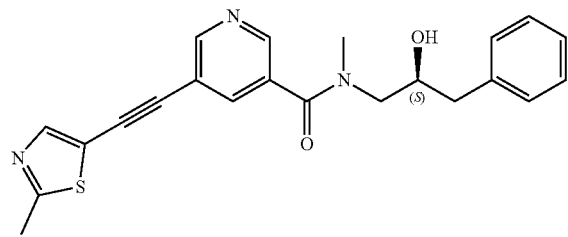
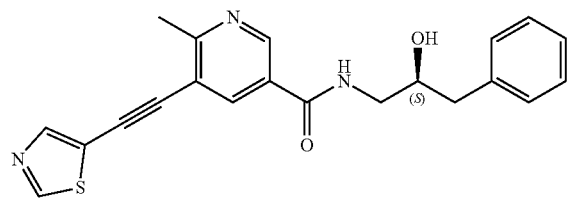
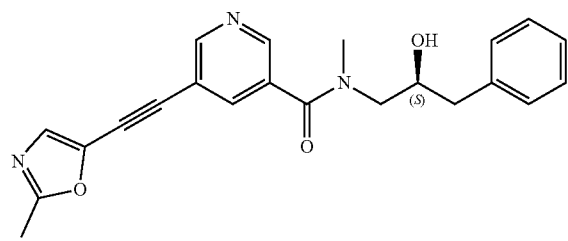
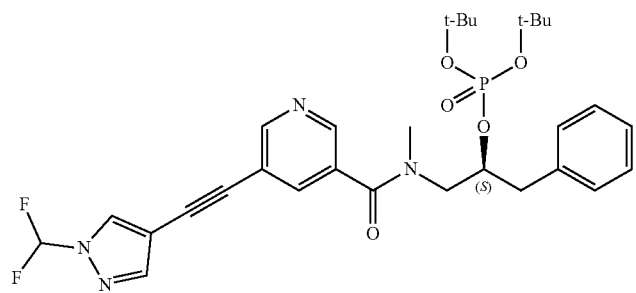

-continued
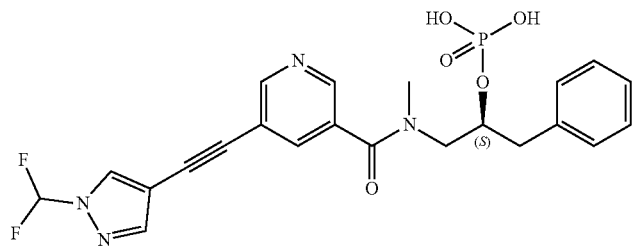
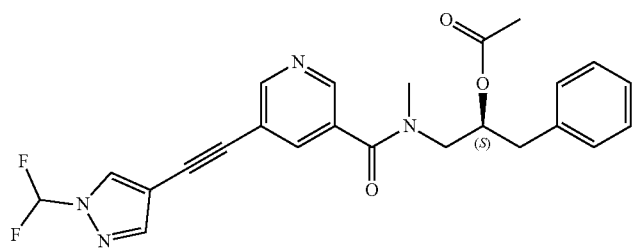
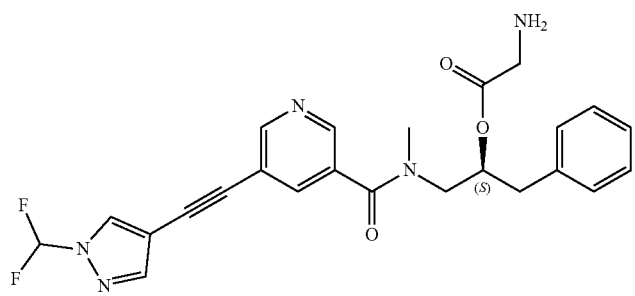
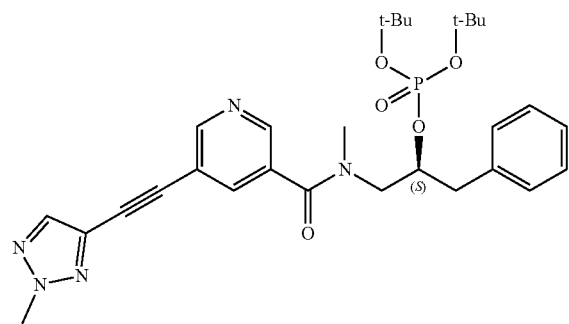
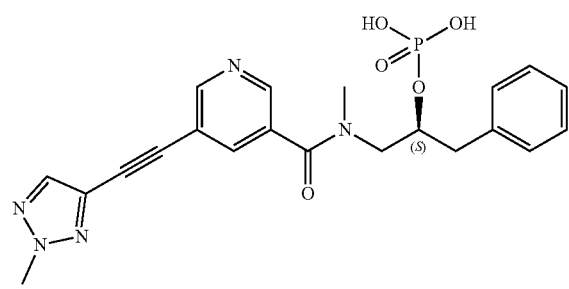

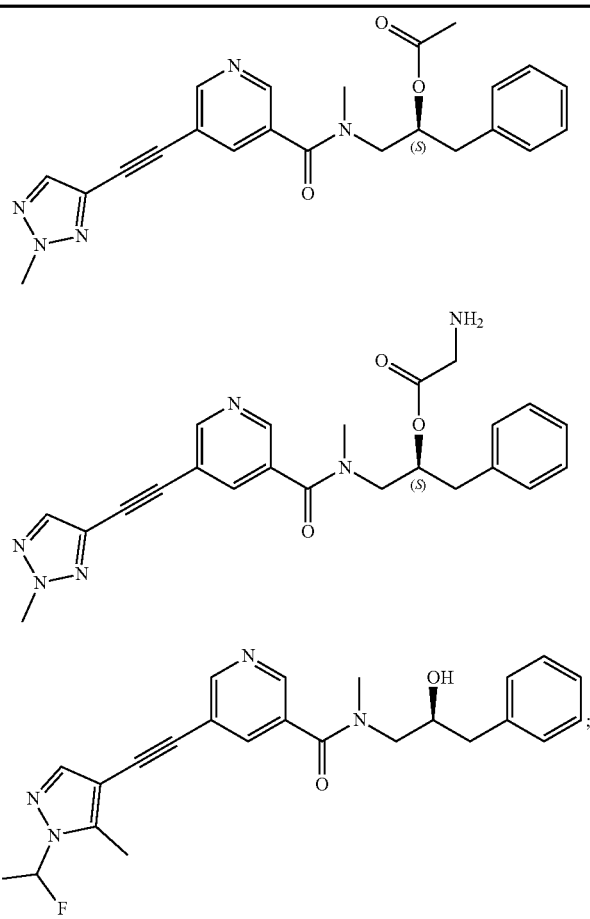

or a pharmaceutically acceptable salt thereof.

Also provided herein are pharmaceutical compositions comprising a compound of Formula (I).

Also provided herein are methods of treating Ulcerative Colitis in a human subject, comprising administering to a human subject having Ulcerative Colitis a compound of Formula (I), or a pharmaceutically acceptable salt thereof.

DEFINITIONS

Figure 1:
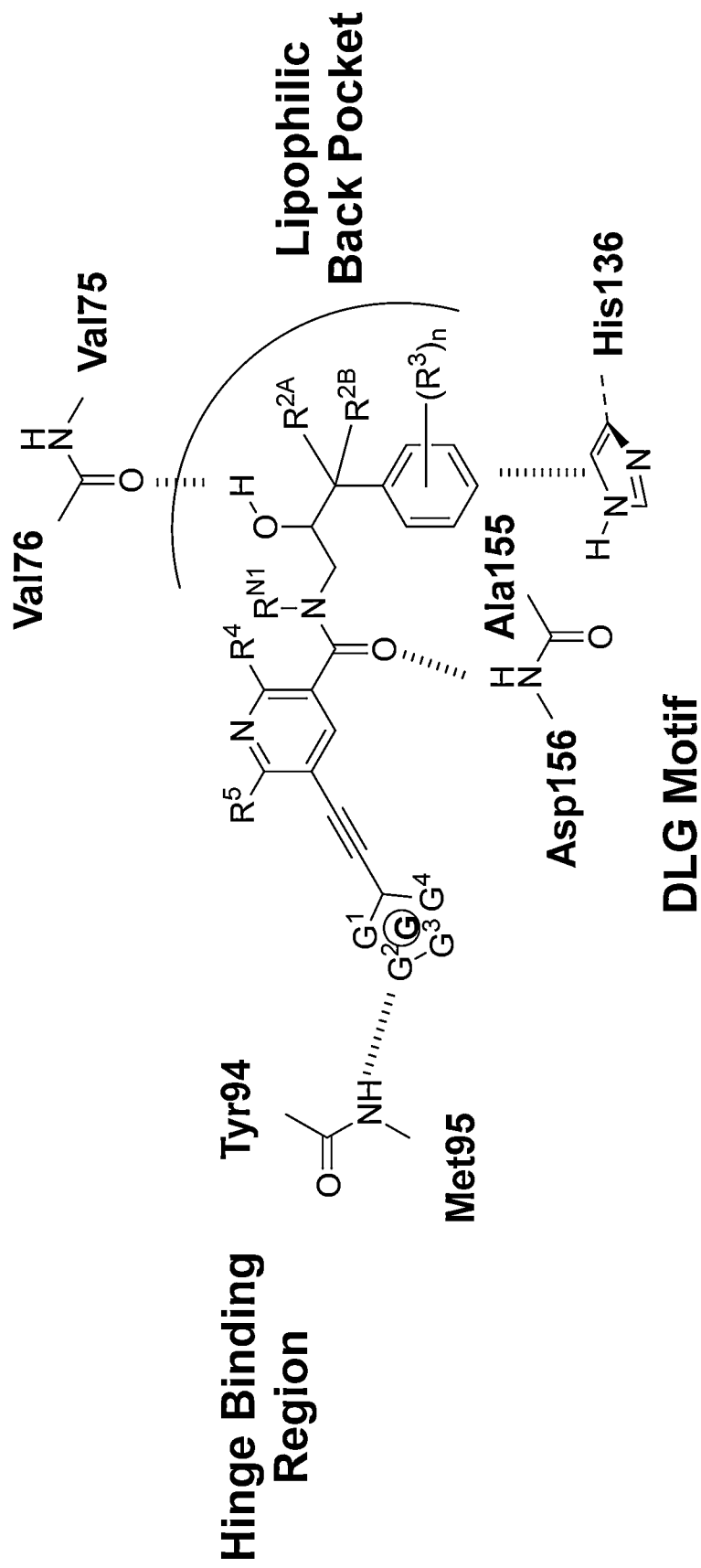
FIG. 1 depicts a modeled binding mode of a compound of Formula (I), wherein $R^1$ is hydrogen, in the ATP (adenoside triphosphate) binding pocket of RIPK1, providing a working hypothesis for the observed RIPK1 binding activity and selectivity over other kinases. In particular, and without wishing to be bound by any particular theory, it is believed several interactions serve as anchor points for binding, from right to left: (1) the terminal phenyl ring fills the volume in a lipophilic back pocket in addition to making an edge-to-face aromatic interaction with the side chain ring of His136; (2) the hydroxyl group makes a hydrogen bond interaction with the backbone carbonyl of the Val76 residue; (3) the carbonyl group makes a hydrogen bond interaction with the backbone Asp156 residue of the DLG motif (Asp156-Leu157-Gly158); and (4) an electron donating group of the heteroaryl ring (designated as "Ring G") makes an interaction with the backbone NH of the Met95 residue in the hinge region. While DLG motif is not unique to RIPK1, it is found in only a small subset of kinases; the majority of kinases instead comprise a DFG (Asp-Phe-Gly) motif. Without wishing to be bound by any particular theory, it further hypothesized that the shape of the lipophilic pocket and interaction with the His136 residue, in addition to the presence of the more accommodating DLG motif (which lacks the bulky phenylalanine ring), drive RIPK1 selectivity by contributing to and accommodating the overall curved binding conformation, thereby allowing for more specific RIPK1 contacts and binding.
Figure 2:
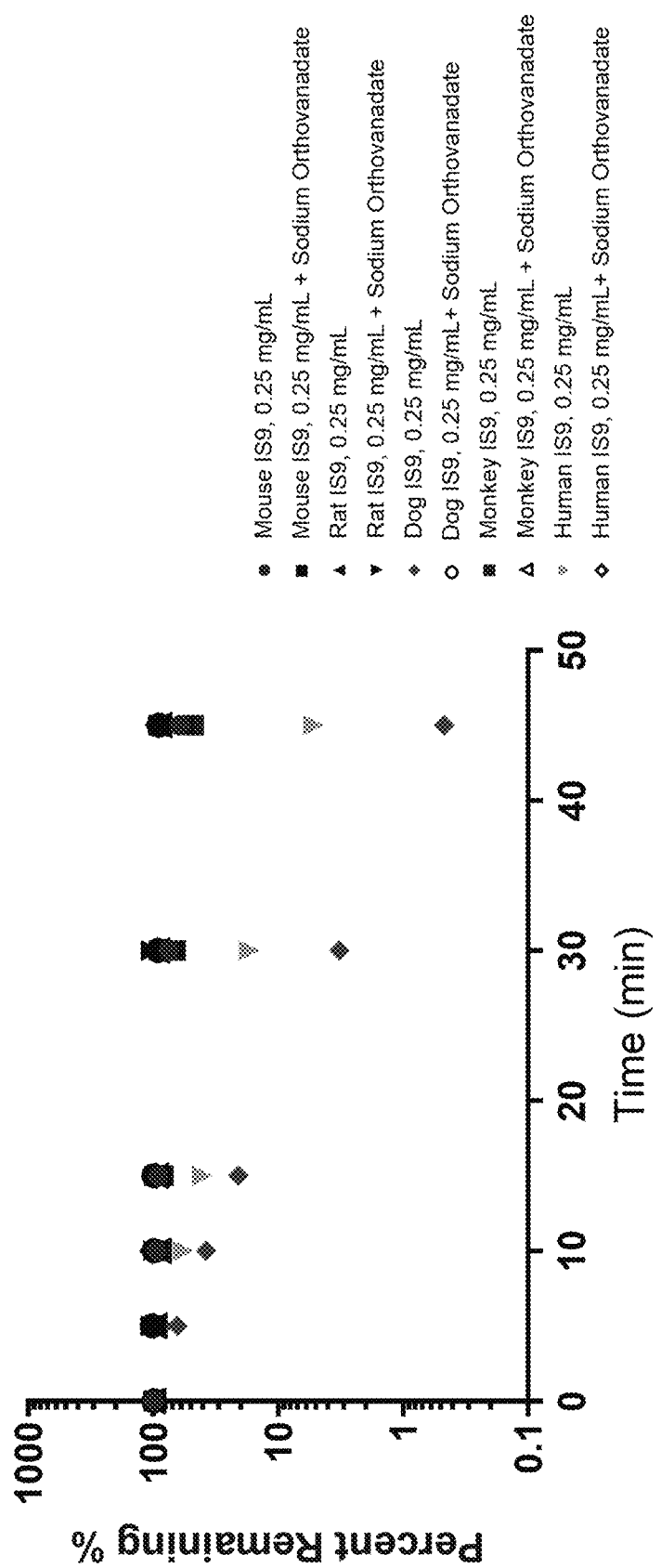
FIG. 2 contains a plot that shows prodrug loss, based on peak area ratios, for Example 19. The inhibition of phosphatase activity by 1 mM orthovanadate as demonstrated by effect on substrate depletion is also shown.
Figure 3:
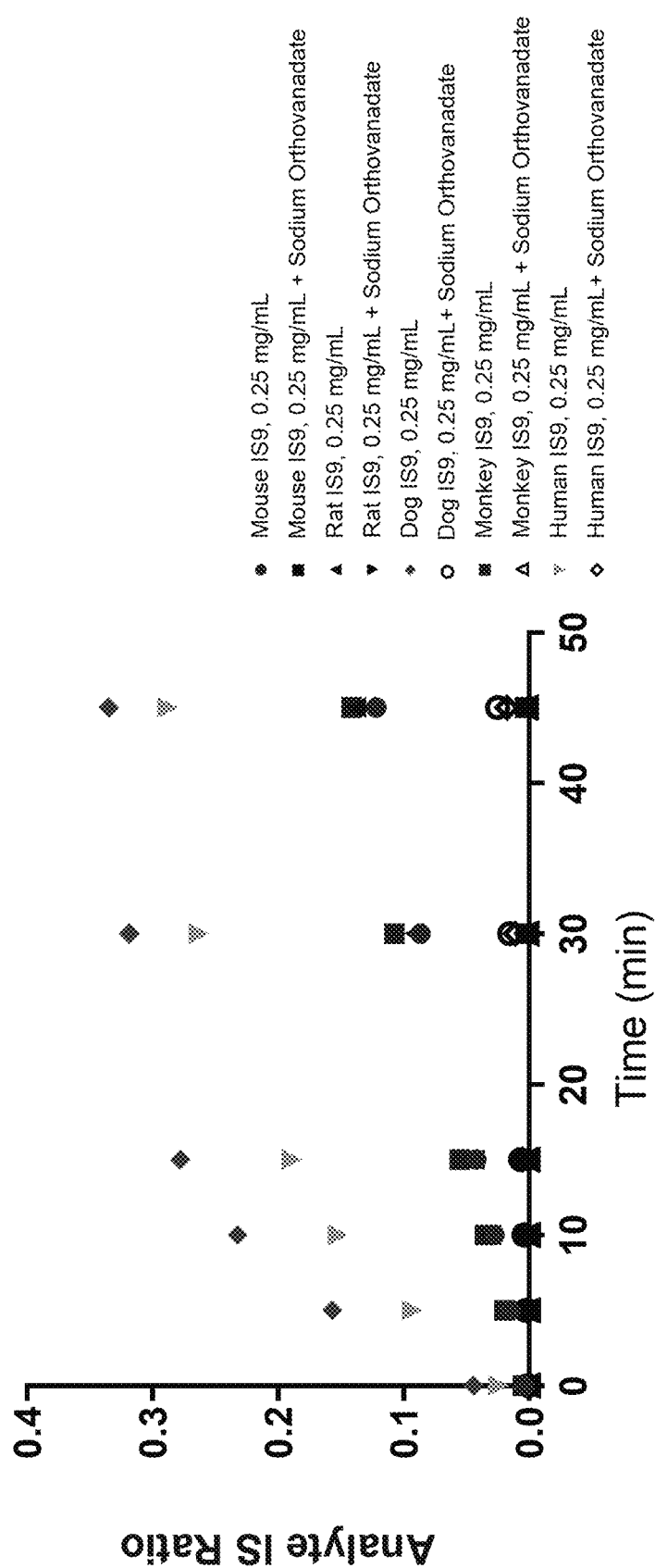
FIG. 3 contains a plot that shows parent formation, based on peak area ratios, for Example 19. The inhibition of phosphatase activity by 1 mM orthovanadate as demonstrated by effect on parent formation is also shown.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein may comprise one or more asymmetric centers, and thus may exist in various stereoisomeric forms, e.g., enantiomers and/or diastereomers and/or geometric (cis/trans or E/Z) isomers in a composition. For example, compositions may comprise a mixture of stereoisomers, including racemic (equal) mixtures, mixtures enriched in one or more stereoisomer, or may comprise an individual stereoisomer in substantially pure (>99%) form. As used herein, "enriched" refers to a composition which comprises greater than (>) 50% of one stereoisomer over the sum total of other stereoisomer(s) which may be present in the composition. In certain embodiments, a composition may comprise >60%, >65%, >70%, >75%, >80%, >85%, >90%, >91%, >92%, >93%, >94%, >95%, >96%, >97%, >98%, >99%, >99.5%, >99.9%, or even up to 100% of one stereoisomer over the sum total of other stereoisomer(s) which may be present in the composition; or may comprise 0% or less than (<) 0.1%, <0.5%, <1%, <2%, <3%, <4%, <5%, <6%, <7%, <8%, <9%, <10%, <15%, <20%, <25%, <30%, <35%, <40%, <45%, or <50% of one stereoisomer over the sum total of other stereoisomer(s) which may be present in the composition. For simplicity, calculating enriched amounts of any of the stereoisomer(s), if provided as pharmaceutically acceptable salt(s) in a composition, are based on the hypothetical amount of free base form. In certain embodiments, a composition is enriched in its (S)-enantiomer. In other embodiments, a composition is enriched in its (R)-enantiomer.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, replacement of a carbon by a $^{13}$C- or $^{14}$C-enriched carbon, and/or replacement of an oxygen atom with $^{18}$O, are within the scope of the disclosure.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a monovalent radical of a straight-chain or branched saturated hydrocarbon group having from 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-4}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), and iso-butyl ($C_4$) groups.

"Haloalkyl" is an alkyl group wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. Examples of haloalkyl groups include —$CF_3$, —$CHF_2$, —$CFH_2$, —$CF_2CF_3$, —$CH_2CF_3$, —$CF_2CF_2CF_3$, —$CCl_3$, —$CFCl_2$, and —$CF_2Cl$.

"Carbocyclyl" or "carbocyclic" refers to a monovalent radical of a monocyclic, non-aromatic, 3- to 6-membered ring system having from 3 to 6 ring carbon atoms ("$C_{3-6}$ carbocyclyl") and zero ring heteroatoms. In some embodiments, a carbocyclyl group has 3 to 4 ring carbon atoms ("$C_{3-4}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), and cyclohexadienyl ($C_6$).

"Heterocyclyl" or "heterocyclic" refers to a monovalent radical of a monocyclic, non-aromatic, 4- to 6-membered ring system having ring carbon atoms and 1 to 3 ring heteroatoms, wherein each heteroatom is independently selected from nitrogen, oxygen, and sulfur ("4- to 6-membered heterocyclyl"). Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, and dihydropyrrolyl. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl.

A "5-membered heteroaryl" refers to a radical of a 5 membered monocyclic 4n+2 aromatic ring system (e.g., having 6 pi electrons shared in a cyclic array) having ring carbon atoms and 1-3 ring heteroatoms provided in the aromatic ring system, wherein each heteroatom is independently selected from nitrogen, oxygen, and sulfur. In heteroaryl groups that contain one or more nitrogen atoms, the point of attachment can be a carbon or nitrogen atom, as valency permits. In some embodiments, the 5-membered heteroaryl has 1-3 ring heteroatoms selected from nitrogen, oxygen, and sulfur. In some embodiments, the 5-membered heteroaryl has 2 ring heteroatoms selected from nitrogen, oxygen, and sulfur. In some embodiments, the 5-membered heteroaryl has 1 ring heteroatom selected from nitrogen, oxygen, and sulfur. Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl.

"Halo" refers to fluorine (fluoro, —F), chlorine (chloro, —Cl), bromine (bromo, —Br), or iodine (iodo, —I).

"Substituted" means that the specified group or moiety bears one or more substituents. Where any group may carry multiple substituents, and a variety of possible substituents is provided, the substituents are independently selected, and need not to be the same. Exemplary substituents include, but are not limited to, hydroxyl, halo, cyano, nitro, thiol, alkyl, alkenyl, carbocyclyl, heterocyclyl, heteroaryl, aryl, heteroarylalkyl, arylalkyl, alkoxy, phosphate, phosponate, amino, amido, carboxylate, and ester.

"Unsubstituted" means that the specified group bears no substituents.

"Optionally and independently substituted" means that the specified group may or may not be further substituted by one or more substituents and that those substituents need not to be the same, if more than one substituent is present.

"Salt" refers to any and all salts, and is produced from the ionic complexation of a basic compound with an inorganic or organic acid, or an acidic compound with an inorganic or organic base, to provide a compound which is electronically neutral. "Pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. See also Berge et al., *J. Pharmaceutical Sciences* (1977) 66:1-19. A "free base" of a compound is the neutral and salt-free form of the compound. In certain embodiments, a compound of Formula (I) may be a salt (e.g., a pharmaceutically acceptable salt). In certain embodiments, e.g., in the absence of reference to a pharmaceutically acceptable salt, a compound of Formula (I) may be present as the free base form.

A "leaving group" refers to a molecular fragment that departs with a pair of electrons in heterolytic bond cleavage wherein the molecular fragment is an anion or neutral molecule. A "leaving group" also refers to a molecular fragment which departs via a cross-coupling reaction. Exemplary leaving groups which depart with a pair of electrons in heterolytic bond cleavage include, but are not limited to, halo (e.g., chloro, bromo, iodo) and activated hydroxyl groups, such as a trifluoromethanesulfonyl activated hydroxyl group (—OTf) 4-toluenesulfonyl activated hydroxyl group (—OTs), methanesulfonyl activated hydroxyl group (—OMs), benzenesulfonyl activated hydroxyl group (—OBs), or —OS(O)$_2$OCH$_3$. Exemplary leaving groups which depart via a cross-coupling reaction, include, but are not limited to, boronic acids or boronic esters (e.g., a dioxoborolane group, e.g., tetramethyl dioxoborolane), trialkyl stannanes (e.g., (R')$_3$Sn—, wherein R' is C$_{1-3}$alkyl), and halo (e.g., chloro, bromo, iodo).

Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999. Exemplary "hydroxyl protecting groups", as used herein, include but are not limited to, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 1-[(2-chloro-4-methyl)phenyl]-4-methoxypiperidin-4-yl (CTMP), allyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, diphenylmethyl, triphenylmethyl, trimethylsilyl (TMS), triethylsilyl (TES), triisopropylsilyl (TIPS), dimethylisopropylsilyl (IPDMS), diethylisopropylsilyl (DEIPS), dimethylhexylsilyl, t-butyldimethylsilyl (TBDMS), t-butyldiphenylsilyl (TBDPS), tribenzylsilyl, triphenylsilyl, diphenylmethylsilyl (DPMS), t-butylmethoxyphenylsilyl (TBMPS), acetate, chloroacetate, dichloroacetate, trichloroacetate, trifluoroacetate, methoxyacetate, triphenylmethoxyacetate, phenoxyacetate, p-chlorophenoxyacetate, methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, and p-nitrobenzyl carbonate.

A "subject" refers to a mammal, and includes, but is not limited to, humans (i.e., a male or female of any age group, e.g., a pediatric subject (e.g., infant, child, adolescent) or adult subject (e.g., young adult, middle-aged adult or senior adult)) and/or other non-human mammals, for example, primates (e.g., cynomolgus monkeys, rhesus monkeys), cats, and/or dogs.

"Treat," "treating" and "treatment" refers to an action that occurs while a subject is suffering from the disease, and which reduces the severity of the disease, or retards or slows the progression of the disease or associated symptoms.

An "effective amount" of a compound, or a pharmaceutically acceptable salt thereof, is an amount, alone or in combination with other therapies, which provides a therapeutic benefit in the treatment of a disease from which the subject suffers, or to delay or minimize one or more symptoms associated with the disease from which the subject suffers.

DETAILED DESCRIPTION OF THE INVENTION (i) Compounds

Described herein are compounds of Formula (I) and pharmaceutically acceptable salts thereof;

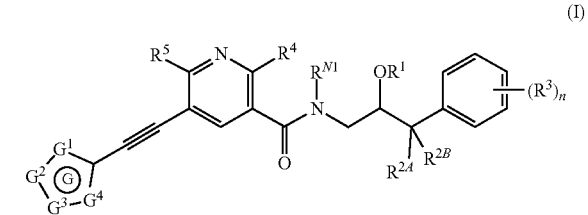

(I)

or a pharmaceutically acceptable salt thereof;
wherein:
R$^1$ is hydrogen, or
R$^1$ is —P(=O)(OR$^{P1}$)$_2$, —C(=O)CH$_2$OR$^{P1}$, —C(=O)CH$_2$N(R$^{P1}$)$_2$, or —C(=O)R$^{P2}$, wherein each instance of $R^{P1}$ is independently selected from the group consisting of hydrogen and substituted or unsubstituted $C_{1-4}$alkyl, and $R^{P2}$ is substituted or unsubstituted $C_{1-4}$alkyl;

$R^{2A}$ and $R^{2B}$ are each independently hydrogen or halo;

each $R^3$ is independently selected from the group consisting of halo and substituted or unsubstituted $C_{1-4}$alkyl, wherein n is 0, 1, or 2;

$R^{N1}$ is hydrogen or substituted or unsubstituted $C_{1-4}$alkyl;

$R^4$ is independently selected from the group consisting of hydrogen, —$OR^{4A}$, and substituted or unsubstituted $C_{1-4}$alkyl, wherein $R^{4A}$ is hydrogen or substituted or unsubstituted $C_{1-4}$alkyl;

$R^5$ is independently selected from the group consisting of hydrogen, —$OR^{5A}$, and substituted or unsubstituted $C_{1-4}$alkyl, wherein $R^{5A}$ is hydrogen or substituted or unsubstituted $C_{1-4}$alkyl;

Ring G is a 5-membered heteroaryl ring, wherein each $G^1$, $G^2$, $G^3$, and $G^4$ is, independently, CH, $CR^{G1}$, N, $NR^{N2}$, O, or S, provided at least one of $G^1$, $G^2$, $G^3$, and $G^4$ is N, $NR^{N2}$, O, or S, and wherein no more than two of $G^1$, $G^2$, $G^3$, and $G^4$ is O or S;

each instance of $R^{G1}$ is independently selected from the group consisting of halo, —$OR^{G2}$, —$NR^7$, substituted or unsubstituted $C_{1-4}$alkyl, substituted or unsubstituted 3-4-membered carbocyclyl, or substituted or unsubstituted 4-membered heterocyclyl, wherein $R^{G2}$ is hydrogen or substituted or unsubstituted $C_{1-4}$alkyl;

or two vicinal $R^{G1}$ groups, taken together with the atoms to which they are attached, form a fused substituted or unsubstituted 5-6 membered carbocyclyl or fused substituted or unsubstituted 5-6 membered heterocyclyl;

or a vicinal $R^{G1}$ group and $R^{N2}$ group, taken together with the atoms to which they are attached, form a fused substituted or unsubstituted 5-6 membered heterocyclyl;

each $R^{N2}$ is independently selected from the group consisting of hydrogen, substituted or unsubstituted $C_{1-4}$alkyl, substituted or unsubstituted 3-4-membered carbocyclyl, and substituted or unsubstituted 4-membered heterocyclyl;

each $R^7$ is independently selected from the group consisting of hydrogen, substituted or unsubstituted $C_{1-4}$alkyl, substituted or unsubstituted 3-4-membered carbocyclyl, and substituted or unsubstituted 4-membered heterocyclyl; and each instance of substituted or unsubstituted is optionally and independently substituted by 0, 1, 2, or 3 substituents selected from the group consisting of halo, —OH, —O($C_{1-4}$alkyl), and —O($C_{1-4}$haloalkyl).

Compounds of Formula (I) may selectively bind to and inhibit RIPK1 (see FIG. 1; RIPK1 Binding Assay in Assays and Activity Data). By inhibiting RIPK1, the compounds of the invention may prevent TNF-induced necroptosis (see U937 TNF/zVAD Cytotoxicity Cell Assay in Assays and Activity Data).

Compounds of Formula (I) may further comprise one or more stereocenters. In certain embodiments, the compound comprises a stereocenter on the carbon to which group $OR^1$ is attached. For example, in certain embodiments, the compound is a stereoisomer of Formula (I-a), or a pharmaceutically acceptable salt thereof. In certain embodiments, the compound is a stereoisomer of Formula (I-b), or a pharmaceutically acceptable salt thereof.

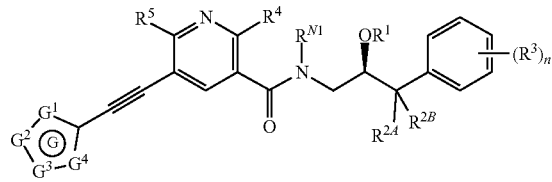

(I-a)

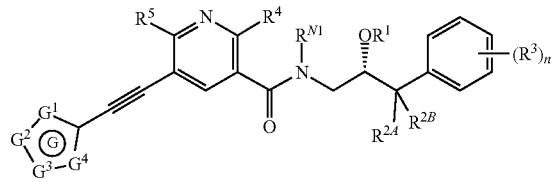

(I-b)

Ring G

In certain embodiments, in Ring G, at least one of $G^1$, $G^2$, $G^3$, and $G^4$ is N or $NR^{N2}$.

In certain embodiments, in Ring G, at least one of $G^2$ or $G^3$ is N or $NR^{N2}$.

In certain embodiments, in Ring G, at least two of $G^1$, $G^2$, $G^3$, and $G^4$ is N or $NR^{N2}$.

In certain such embodiments, Ring G is a diazole. In certain such embodiments, $G^2$ and $G^3$ are each independently N or $NR^{N2}$.

In further embodiments, Ring G is a triazole. In certain such embodiments, $G^2$, $G^3$, and $G^4$ are each independently N or $NR^{N2}$.

In certain embodiments, $R^{N2}$ is alkyl or haloalkyl.

In certain embodiments, e.g., in which at least one of $G^1$, $G^2$, $G^3$, and $G^4$ is N or $NR^{N2}$ or in which Ring G is a diazole, one of $G^1$ and $G^2$ is $CR^{G1}$. In certain such embodiments, $R^{G1}$ is methyl or cyclopropyl.

Exemplary groups of formula

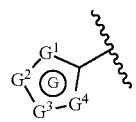

include, but are not limited to,

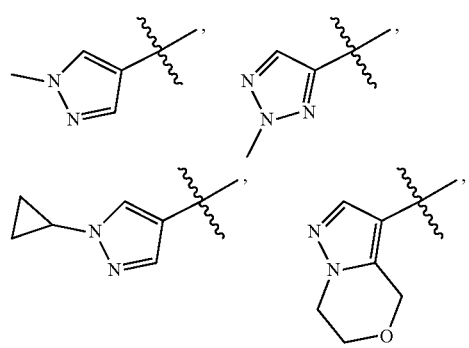

-continued

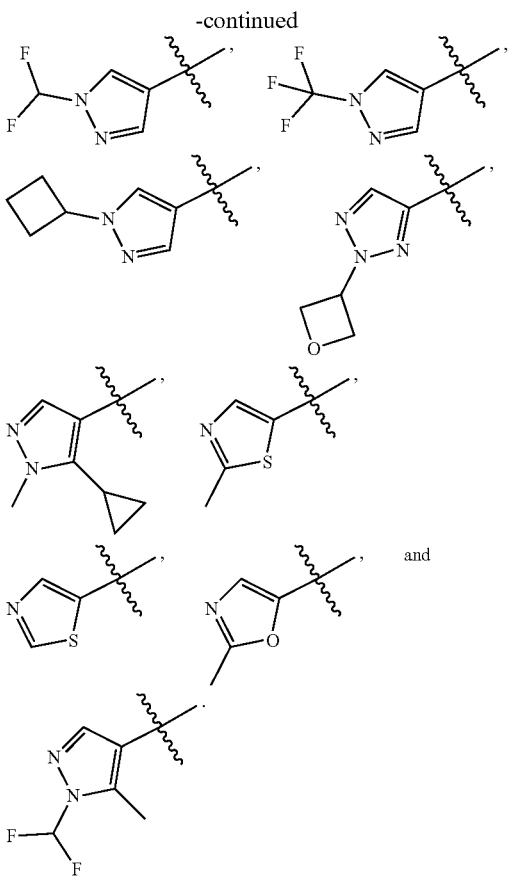

R⁴ and R⁵

In certain embodiments, $R^4$ is hydrogen.

In certain embodiments, $R^5$ is hydrogen, alkoxy, or haloalkyl.

In certain embodiments, $R^5$ is hydrogen, methyl, methoxy, or difluoromethyl. For example, $R^5$ may be hydrogen.

$R^{N1}$

In certain embodiments, $R^{N1}$ is hydrogen or methyl. For example, $R^{N1}$ may be hydrogen. Alternatively, $R^{N1}$ is methyl.

$R^{2A}$ and $R^{2B}$

In certain embodiments, $R^{2A}$ and $R^{2B}$ are each hydrogen. Alternatively, one of $R^{2A}$ and $R^{2B}$ is hydrogen and the other is fluoro.

$R^3$ and n

In certain embodiments, n is 0 or 1.

In some embodiments, n is 1. In certain such embodiments, $R^3$ is halo. Alternatively, n is 0.

$R^1$

In certain embodiments, $R^1$ is hydrogen.

Alternatively, $R^1$ may be —P(=O)(OR$^{P1}$)$_2$, —C(=O)CH$_2$N(R$^{P1}$)$_2$, or —C(=O)R$^{P2}$. For example, in some embodiments, $R^1$ is —P(=O)(OR$^{P1}$)$_2$. In certain such embodiments, each $R^{P1}$ is independently selected from the group consisting of hydrogen and unsubstituted C$_{1-4}$alkyl. For example, each $R^{P1}$ may be hydrogen. Alternatively, each $R^{P1}$ may be unsubstituted C$_{1-4}$alkyl.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is hydrogen.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted C$_{1-4}$alkyl. In certain preferred embodiments, each $R^{P1}$ is H.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0; and $R^1$ is hydrogen.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0; and $R^1$ is —P(=O)(OR$^{P1}$)$_2$. In certain such embodiments, each $R^{P1}$ is independently selected from the group consisting of hydrogen and unsubstituted C$_{1-4}$alkyl. In certain preferred embodiments, each $R^{P1}$ is H.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 1; $R^3$ is halo; and $R^1$ is hydrogen.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 1; $R^3$ is halo; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 1; $R^3$ is halo; and $R^1$ is —P(=O)(OR$^{P1}$)$_2$. In certain such embodiments, each $R^{P1}$ is independently selected from the group consisting of hydrogen and unsubstituted C$_{1-4}$alkyl. In certain preferred embodiments, each $R^{P1}$ is H.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; one of $R^{2A}$ and $R^{2B}$ is hydrogen and the other is fluoro; n is 0 or 1; and $R^1$ is hydrogen.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; one of $R^{2A}$ and $R^{2B}$ is hydrogen and the other is fluoro; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen or methyl; one of $R^{2A}$ and $R^{2B}$ is hydrogen and the other is fluoro; n is 0 or 1; and $R^1$ is —P(=O)(OR$^{P1}$)$_2$. In certain such embodiments, each $R^{P1}$ is independently selected from the group consisting of hydrogen and unsubstituted C$_{1-4}$alkyl. In certain preferred embodiments, each $R^{P1}$ is H.

In certain embodiments of Formula (I), at least one of G² or G³ is N or NR$^{N2}$; $R^4$ is hydrogen; $R^5$ is hydrogen, alkoxy, or haloalkyl; $R^{N1}$ is hydrogen; $R^{2A}$ and $R^{2B}$ are each hydrogen; n is 0 or 1; and $R^1$ is hydrogen.

In certain embodiments of Formula (I), at least one of $G^2$ or $G^3$ is N or $NR^{N2}$; $R^4$ is hydrogen; $R^5$ is hydrogen, alkoxy, or haloalkyl; $R^{N1}$ is hydrogen; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of $G^2$ or $G^3$ is N or $NR^{N2}$; $R^4$ is hydrogen; $R^5$ is hydrogen, alkoxy, or haloalkyl; $R^{N1}$ is hydrogen; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), at least one of $G^2$ or $G^3$ is N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is hydrogen.

In certain embodiments of Formula (I), at least one of $G^2$ or $G^3$ is N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of $G^2$ or $G^3$ is N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), at least one of $G^2$ or $G^3$ is N or $NR^{N2}$; $R^4$ is hydrogen; $R^5$ is hydrogen, methyl, methoxy, or difluoromethyl; $R^{N1}$ is methyl; $R^{2A}$ and $R^{2B}$ are each hydrogen; n is 0 or 1; and $R^1$ is hydrogen.

In certain embodiments of Formula (I), at least one of $G^2$ or $G^3$ is N or $NR^{N2}$; $R^4$ is hydrogen; $R^5$ is hydrogen, methyl, methoxy, or difluoromethyl; $R^{N1}$ is methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), at least one of $G^2$ or $G^3$ is N or $NR^{N2}$; $R^4$ is hydrogen; $R^5$ is hydrogen, methyl, methoxy, or difluoromethyl; $R^{N1}$ is methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is hydrogen.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), $G^2$ and $G^3$ are each independently N or $NR^{N2}$; $R^4$ is hydrogen; $R^5$ is hydrogen, methyl, methoxy; $R^{N1}$ is hydrogen or methyl; $R^{2A}$ and $R^{2B}$ are each hydrogen; n is 0 or 1; and $R^1$ is hydrogen.

In certain embodiments of Formula (I), $G^2$ and $G^3$ are each independently N or $NR^{N2}$; $R^4$ is hydrogen; $R^5$ is hydrogen, methyl, methoxy; $R^{N1}$ is hydrogen or methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), $G^2$ and $G^3$ are each independently N or $NR^{N2}$; $R^4$ is hydrogen; $R^5$ is hydrogen, methyl, methoxy; $R^{N1}$ is hydrogen or methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is hydrogen.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is —P(=O)(OR$^{P1}$)$_2$, —C(=O)CH$_2$N(R$^{P1}$)$_2$, or —C(=O)R$^{P2}$.

In certain embodiments of Formula (I), $G^2$ and $G^3$ are each independently N or $NR^{N2}$; $R^4$ is hydrogen; $R^5$ is hydrogen, alkoxy, or haloalkyl; $R^{N1}$ is methyl; $R^{2A}$ and $R^{2B}$ are each hydrogen; n is 0 or 1; and $R^1$ is —P(=O)(OR$^{P1}$)$_2$. In certain such embodiments, each $R^{P1}$ is independently selected from the group consisting of hydrogen and unsubstituted $C_{1-4}$alkyl. In certain preferred embodiments, each $R^{P1}$ is H.

In certain embodiments of Formula (I), at least one of $G^2$ or $G^3$ is N or $NR^{N2}$; $G^1$ is $CR^{G1}$; $R^{G1}$ is methyl or cyclopropyl; $R^4$ is hydrogen; $R^5$ is hydrogen, alkoxy, or haloalkyl; $R^{N1}$ is hydrogen or methyl; $R^{2A}$ and $R^{2B}$ are each hydrogen; n is 0 or 1; and $R^1$ is hydrogen.

In certain embodiments, the compound is selected from the group consisting of:

(S)-N-(2-hydroxy-3-phenylpropyl)-N-methyl-5-((1-methyl-1H-pyrazol-4-yl)ethynyl)nicotinamide;

(S)-5-((1-(difluoromethyl)-1H-pyrazol-4-yl)ethynyl)-N-(2-hydroxy-3-phenylpropyl)-N-methylnicotinamide;

(S)-N-(2-hydroxy-3-phenylpropyl)-N-methyl-5-((2-methyl-2H-1,2,3-triazol-4-yl)ethynyl)nicotinamide;

(S)-N-(2-hydroxy-3-phenylpropyl)-N-methyl-5-((1-(trifluoromethyl)-1H-pyrazol-4-yl)ethynyl)nicotinamide;

(S)-5-((1-cyclopropyl-1H-pyrazol-4-yl)ethynyl)-N-(2-hydroxy-3-phenylpropyl)-N-methylnicotinamide;

(S)-5-((1-cyclobutyl-1H-pyrazol-4-yl)ethynyl)-N-(2-hydroxy-3-phenylpropyl)-N-methylnicotinamide;

N-((2R,3S)-3-fluoro-2-hydroxy-3-phenylpropyl)-N-methyl-5-((1-methyl-1H-pyrazol-4-yl)ethynyl)nicotinamide;

(S)-5-((6,7-dihydro-4H-pyrazolo[5,1-c][1,4]oxazin-3-yl)ethynyl)-N-(2-hydroxy-3-phenylpropyl)-N-methylnicotinamide;

(R)-6-(difluoromethyl)-N-(2-hydroxy-3-phenylpropyl)-N-methyl-5-((1-methyl-1H-pyrazol-4-yl)ethynyl)nicotinamide;

(S)-N-(2-hydroxy-3-phenylpropyl)-N-methyl-5-((2-(oxetan-3-yl)-2H-1,2,3-triazol-4-yl)ethynyl)nicotinamide;

(S)-5-((5-cyclopropyl-1-methyl-1H-pyrazol-4-yl)ethynyl)-N-(2-hydroxy-3-phenylpropyl)-N-methylnicotinamide;

(S)-N-(3-(3-fluorophenyl)-2-hydroxypropyl)-N-methyl-5-((1-methyl-1H-pyrazol-4-yl)ethynyl)nicotinamide;

(S)-N-(2-hydroxy-3-phenylpropyl)-6-methoxy-N-methyl-5-((1-methyl-1H-pyrazol-4-yl)ethynyl)nicotinamide;

(S)-N-(2-hydroxy-3-phenylpropyl)-N,6-dimethyl-5-((1-methyl-1H-pyrazol-4-yl)ethynyl)nicotinamide;

(S)-N-(2-hydroxy-3-phenylpropyl)-N-methyl-5-((2-methylthiazol-5-yl)ethynyl)nicotinamide;

(S)-N-(2-hydroxy-3-phenylpropyl)-6-methyl-5-(thiazol-5-ylethynyl)nicotinamide;

(S)-N-(2-hydroxy-3-phenylpropyl)-N-methyl-5-((2-methyloxazol-5-yl)ethynyl)nicotinamide;

(S)-di-tert-butyl (1-(5-((1-(difluoromethyl)-1H-pyrazol-4-yl)ethynyl)-N-methylnicotinamido)-3-phenylpropan-2-yl) phosphate;

(S)-1-(5-((1-(difluoromethyl)-1H-pyrazol-4-yl)ethynyl)-N-methylnicotinamido)-3-phenylpropan-2-yl dihydrogen phosphate;

(S)-1-(5-((1-(difluoromethyl)-1H-pyrazol-4-yl)ethynyl)-N-methylnicotinamido)-3-phenylpropan-2-yl acetate;

(S)-1-(5-((1-(difluoromethyl)-1H-pyrazol-4-yl)ethynyl)-N-methylnicotinamido)-3-phenylpropan-2-yl glycinate;

(S)-di-tert-butyl (1-(N-methyl-5-((2-methyl-2H-1,2,3-triazol-4-yl)ethynyl)nicotinamido)-3-phenylpropan-2-yl) phosphate;

(S)-1-(N-methyl-5-((2-methyl-2H-1,2,3-triazol-4-yl)ethynyl)nicotinamido)-3-phenylpropan-2-yl dihydrogen phosphate;

(S)-1-(N-methyl-5-((2-methyl-2H-1,2,3-triazol-4-yl)ethynyl)nicotinamido)-3-phenylpropan-2-yl acetate;

(S)-1-(N-methyl-5-((2-methyl-2H-1,2,3-triazol-4-yl)ethynyl)nicotinamido)-3-phenylpropan-2-yl glycinate; and (S)-5-((1-(difluoromethyl)-5-methyl-1H-pyrazol-4-yl)ethynyl)-N-(2-hydroxy-3-phenylpropyl)-N-methylnicotinamide.

The compound names listed above were generated from the structures by PerkinElmer ChemDraw Version 19.1.1.21 or 21.0.0.28.

In certain embodiments, a compound of Formula (I) is selected from the group consisting of:

(1)

(2)

(3)

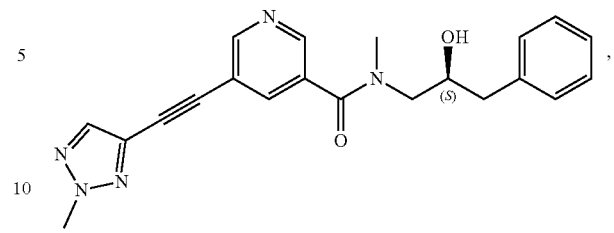

(4)

(5)

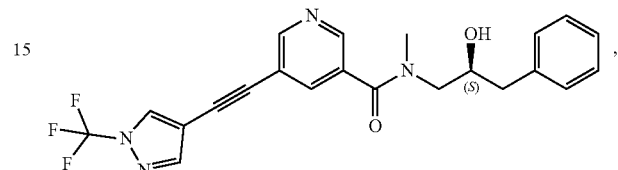

(6)

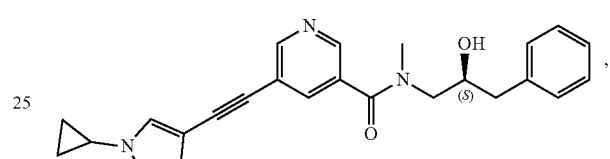

(7)

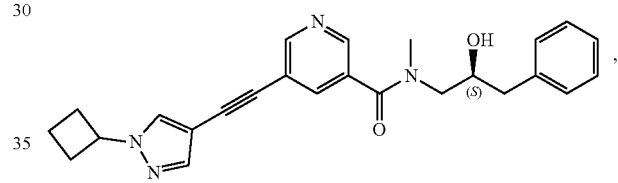

(8)

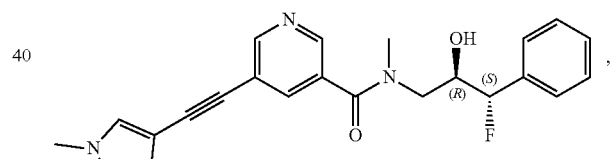

(9)

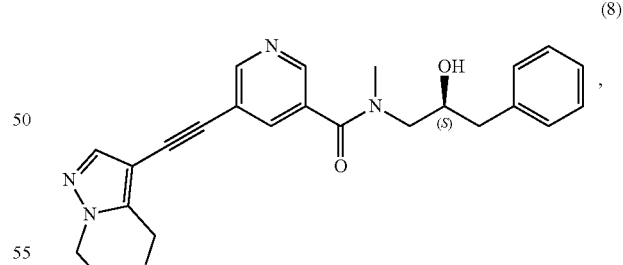

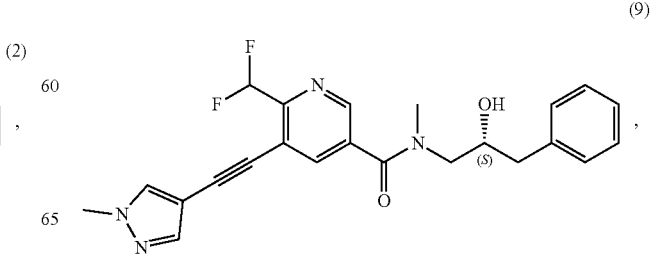

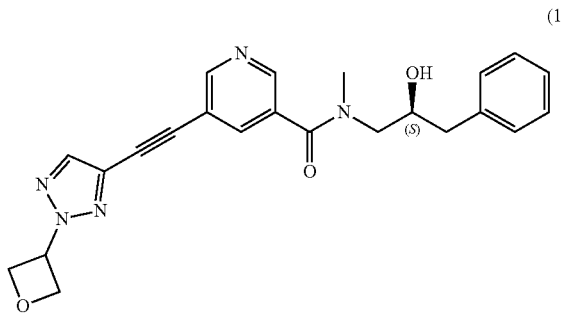
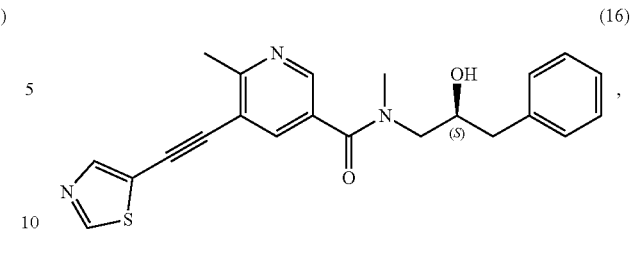

-continued

(22)
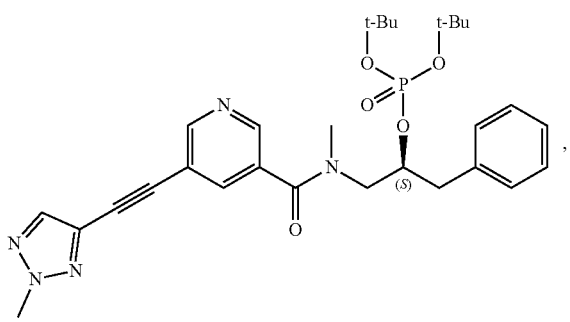

(23)
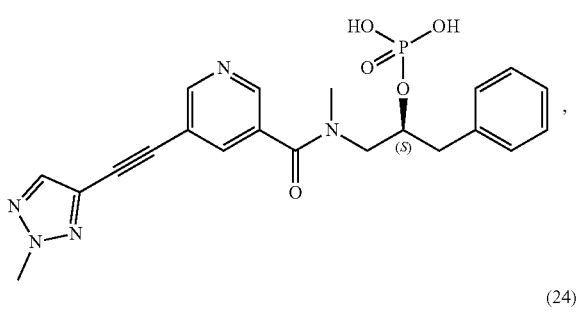

(24)
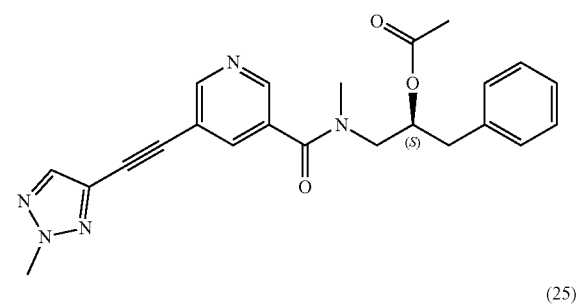

(25)
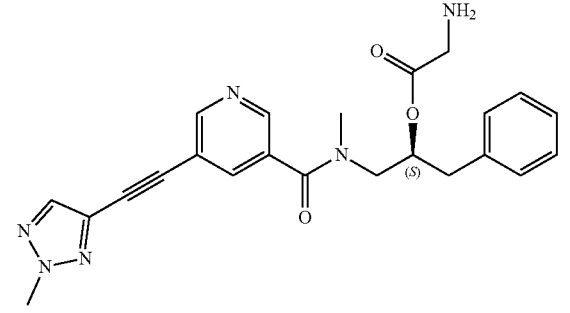

(26)
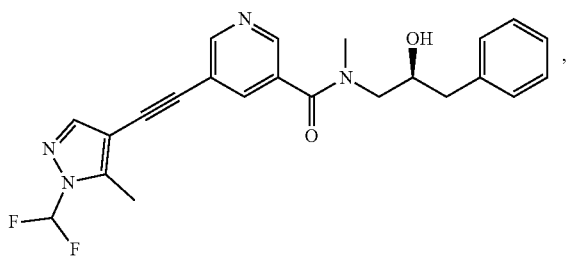

and pharmaceutically acceptable salts thereof.

(ii) Pharmaceutical Compositions and Methods of Use

In another aspect, the invention relates to pharmaceutical compositions comprising a therapeutically effective amount of a compound of formula (I), or a pharmaceutically acceptable salt thereof, in combination with a pharmaceutically acceptable carrier.

Compounds of Formula (I), their pharmaceutically acceptable salts, and pharmaceutical compositions comprising same, may be useful in the treatment of subjects suffering from various diseases and conditions, e.g., such as those associated with inhibition of RIPK1 activity. For example, in some embodiments, the compounds of the invention are useful for treating Ulcerative Colitis. Further provided are compounds of Formula (I), or pharmaceutically acceptable salts thereof, or compositions comprising same, for use in a medicament, e.g., for use in treating Ulcerative Colitis.

(iii) Preparative Methods

Further provided herein are exemplary methods of preparing compounds of Formula (I), and salts thereof. See, e.g., Schemes 1-4 below, and the Examples.

In certain aspects, compounds of Formula (I), wherein $R^1$ is H, and salts thereof, may be made via a cross-coupling reaction between a heteroaryl group and a terminal alkyne (see, e.g., Schemes 1 and 2).

Scheme 1 depicts a method of making a compound of Formula (I), wherein $R^1$ is H, or a salt thereof, by coupling a compound of formula (A), which comprises a terminal alkyne group, to a compound of Formula (B), which comprises a pyridinyl group substituted by a leaving group $LG^1$ under coupling conditions sufficient to generate a compound of Formula (I). In certain embodiments, the leaving group $LG^1$ is a halo (e.g., chloro, bromo, iodo) or an activated hydroxyl group (e.g., —OTf, —OTs, —OMs, or —OBs). In certain embodiments, the coupling conditions comprise a Pd(II) catalyst, optionally a ligand, and a base. For example, the Pd(II) catalyst may be bis(acetonitrile)dichloropalladium (II) (Pd(MeCN)$_2$Cl$_2$), Chloro(2-dicyclohexylphosphino-2',4',6'-triisopropyl-1,1'-biphenyl)[2-(2'-amino-1,1'-biphenyl)]palladium(II) (XPhos Pd G$^2$), the ligand may be 2-dicyclohexylphosphino-2',4',6'-triisopropylbiphenyl (X-Phos), and the base may be Cs$_2$CO$_3$. In other embodiments, the coupling conditions comprise a Pd(0) catalyst, optionally a ligand, and a base. For example, the Pd(0) catalyst may be bis(tri-tert-butylphosphine)palladium(0) and the base may be potassium phosphate. In certain embodiments, the coupling conditions further comprise a copper salt, e.g., CuI.

Scheme 2 depicts a method of making a compound of Formula (I), wherein $R^1$ is H, or a salt thereof, by coupling a compound of formula (C), which comprises a leaving group $LG^2$, to a compound of Formula (D), which comprises a pyridinyl group substituted by a terminal alkyne group under coupling conditions sufficient to generate a compound of Formula (I). In certain embodiments, the leaving group $LG^2$ is a halo (e.g., chloro, bromo, iodo) or an activated hydroxyl group (e.g., —OTf, —OTs, —OMs, or —OBs). In certain embodiments, the coupling conditions comprise a Pd(II) catalyst, optionally a ligand, and a base. For example, the Pd(II) catalyst may be bis(acetonitrile)dichloropalladium (II) (Pd(MeCN)$_2$Cl$_2$), Chloro(2-dicyclohexylphosphino-2',4',6'-triisopropyl-1,1'-biphenyl)[2-(2'-amino-1,1'-biphenyl)]palladium(II) (XPhos Pd G$^2$), the ligand may be 2-dicyclohexylphosphino-2',4',6'-triisopropylbiphenyl (X-Phos), and the base may be Cs$_2$CO$_3$. In other embodiments, the coupling conditions comprise a Pd(0) catalyst, optionally a ligand, and a base. For example, the Pd(0) catalyst may be bis(tri-tert-butylphosphine)palladium(0) and the base may be potassium phosphate. In certain embodiments, the coupling conditions further comprise a copper salt, e.g., CuI.

In certain aspects, compounds of Formula (I), and salts thereof, may be made via an amide coupling reaction (see, e.g., Scheme 3).

Scheme 3 depicts a method of making a compound of Formula (I), wherein $R^1$ is H, or a salt thereof, by coupling a compound of formula (E), which comprises a leaving group $LG^3$ bound to a carbonyl group, to a compound of Formula (F), which comprises an amino group —$NHR^{N1}$ under coupling conditions sufficient to generate a compound of Formula (I). In certain embodiments, the leaving group $LG^3$ is a halo (e.g., chloro, bromo, iodo), a hydroxyl group, or an activated hydroxyl group (e.g., —OTf, —OTs, —OMs, or —OBs). In certain embodiments, the coupling conditions comprise an amide-coupling reagent and a base. In certain embodiments, the amide coupling reagent is 1-[Bis(dimethylamino)methylene]-1H-1,2,3-triazolo[4,5-b]pyridinium 3-oxid hexafluorophosphate (HATU), N,N'-carbonyldiimidazole (CDI), 2-(1H-Benzotriazole-1-yl)-1,1,3,3-tetramethylaminium tetrafluoroborate (TBTU), In certain embodiments, the base is N,N-Diisopropylethylamine (DIEA) or trimethylamine (TEA).

In certain embodiments, compounds of Formula (I) wherein $R^1$ is not H may be made by a reaction in which the —$OR^1$ hydroxyl group is substituted, e.g., by a phosphate group.

Scheme 4 depicts a method of making a compound of Formula (I) wherein $R^1$ is —$P(=O)(OR^P)_2$, or a salt thereof, by reacting the hydroxyl group with a phosphorus-containing agent under conditions sufficient to yield the compound wherein $R^1$ is —$P(=O)(OR^P)_2$. In some embodiments, the phosphorus-containing agent is a phosphoramidite (e.g., di-tert-butyl diethylphosphoramidite).

Scheme 1

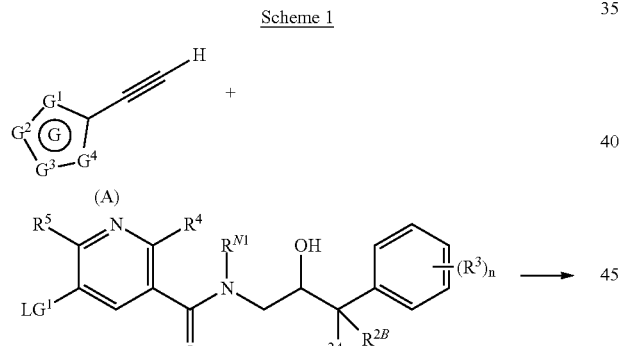

Scheme 2

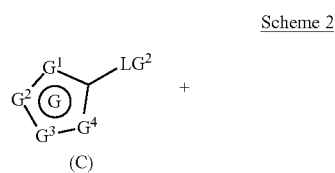

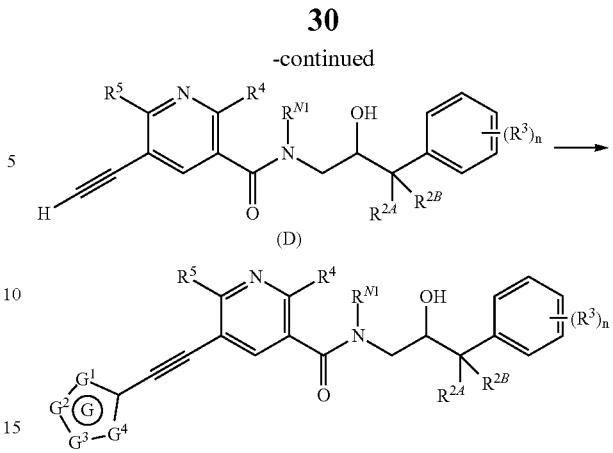

Scheme 3

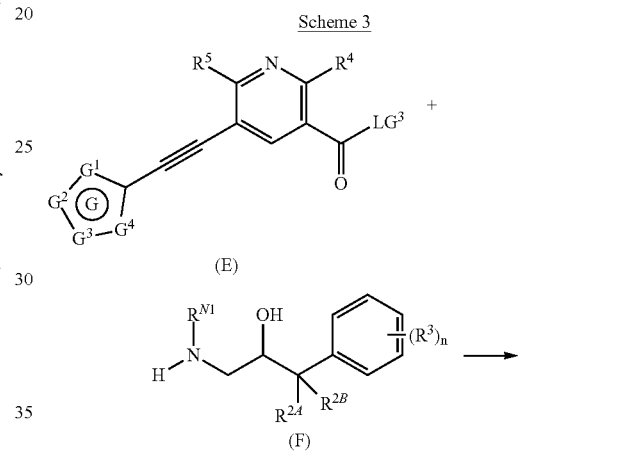

Scheme 4

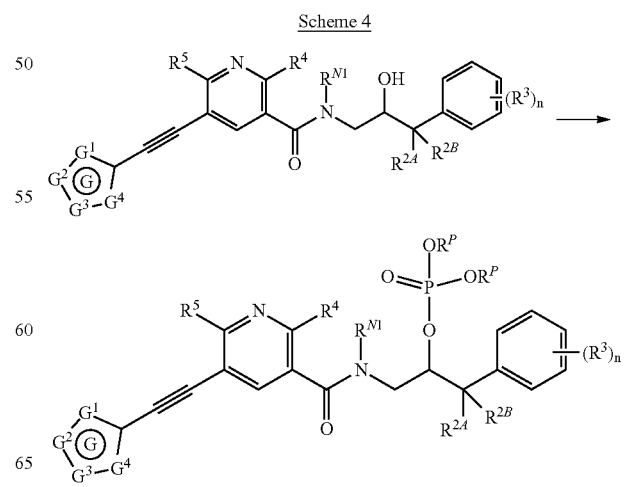

EXEMPLIFICATION

In order that this disclosure may be more fully understood, the following Examples are set forth. It should be understood that these Examples are for illustrative purposes only and are not to be construed as limiting this disclosure in any manner.

Common abbreviations well known to those skilled in the art which are used throughout include those in Table A.

TABLE A

Abbreviations

| Abbreviation | Definition |
| --- | --- |
| NMR | nuclear magnetic resonance |
| s | singlet |
| br s | broad singlet |
| d | doublet |
| br d | broad doublet |
| t | triplet |
| br t | broad triplet |
| q | quartet |
| m | multiplet |
| br m | broad multiplet |
| dd | doublet of doublet |
| br dd | broad doublet of doublet |
| ddd | doublet of doublet of doublet |
| dt | doublet of triplet |
| dtd | doublet of triplet of doublet |
| tt | triplet of triplet |
| min | minute |
| h | hour |
| mL | milliliter |
| μl | microliter |
| L | liter |
| g | gram |
| mg | milligram |
| mmol | millimoles |
| M | molarity (moles/liter) |
| μM | micromolar |
| nM | nanomolar |
| ppm | parts per million |
| HPLC | high pressure liquid chromatography |
| UPLC ® or UHPLC | ultra high performance liquid chromatography |
| LC/MS or LCMS | liquid chromatography-mass spectrometry |
| MS | mass spectrometry |
| ATP | adenosine triphosphate |
| BSA | bovine serum albumin |
| EDTA | ethylenediaminetetraacetic acid |
| DTT | dithiothreitol |
| FRET | fluorescence energy transfer |
| HEPES | (4-(2-hydroxyethyl)-1-piperazineethanesulfonic acid) |
| $IC_{50}$ | half maximal inhibitory concentration |
| Boc | tert-butoxycarboxyl |
| MOM | methoxymethyl |
| PMBM | para-methoxybenzylmethyl |
| THP | tetrahydropyranyl |
| XPhos | 2-dicyclohexylphosphino-2,4,6-triisopropylbiphenyl |
| XPhos Pd G2 | chloro(2-dicyclohexylphosphino-2',4',6'-triisopropyl-1,1'-biphenyl)[2-(2'-amino-1,1'-biphenyl)]palladium(II) |
| $R_t$ | Retention time |

Analytical Methods

Unless otherwise stated, all $^1$H NMR data were collected on a Varian 400 MHz Mercury Plus, Inova, or 400-MR instrument and chemical shifts are quoted in parts per million (ppm). HPLC (High pressure Liquid Chromatography), UPLC (ultra performance liquid chromatography, and LC/mass spectrometry (LC/MS) conditions are referenced using the Method letter as provided in Table B.

TABLE B

| Method | Conditions |
|---|---|
| aa | LC/MS: The gradient was 5-60% mobile phase B in 1.6 minute then 60-95% mobile phase B to 2.2 minutes with a hold at 95% mobile phase B for 0.1 minute (1.0 mL/minute flow rate). Mobile phase A was 10 mM ammonium acetate (NH$_4$OAc), mobile phase B was HPLC grade acetonitrile (MeCN). The column used for the chromatography is a 2.1 × 30 mm Waters Cortecs C18 column (1.6 µm particles). Detection methods are diode array (DAD) and evaporative light scattering (ELSD) detection as well as positive/negative electrospray ionization in Mass Spectrometry. |
| bb | LC/MS: The gradient was 5-95% mobile phase B over 15 minutes (1.0 mL/minute flow rate). Mobile phase A was 0.1% formic acid in water, mobile phase B was HPLC grade acetonitrile (MeCN). The column used for the chromatography was 2.1 × 30 mm Waters X-Select UPLC C18 (1.7 µm particles). Detection methods were diode array (DAD) and evaporative light scattering (ELSD) detection as well as positive/negative electrospray ionization. |
| cc | LC/MS: The gradient was 5-95% mobile phase B over 4 minute (1.0 mL/minute flow rate). Mobile phase A was 0.1% formic acid in water, mobile phase B was HPLC grade acetonitrile (MeCN). The column used for the chromatography was 4.6 × 30 mm Waters X-Select UPLC C18 (2.5 µm particles). Detection methods were diode array (DAD) and evaporative light scattering (ELSD) detection as well as positive/negative electrospray ionization. |
| dd | LC/MS: The gradient was 5-95% mobile phase B for 3 minutes (2.5 mL/minute flow rate). Mobile phase A was 0.1% ammonium in water, mobile phase B was HPLC grade acetonitrile (MeCN). The column used for the chromatography is a 4.6 × 30 mm Waters X-Bridge BEH C18 (2.5 um particles). Detection method is UV (254 nm) as well as positive/negative electrospray ionization. |
| ee | LC/MS: The gradient was 5-95% mobile phase B for 3 minutes (2.5 mL/minute flow rate). Mobile phase A was 0.1% formic acid, mobile phase B was HPLC grade acetonitrile (MeCN) with 0.1% formic acid. The column used for the chromatography is a 4.6 × 30 mm X-Select CSH C18 XP (2.5 um particles). Detection method is UV (254 nm) as well as positive/negative electrospray ionization. |
| ff | LC/MS (The gradient was 5% mobile phase B in 0.40 minutes and 5-95% mobile phase B at 0.40-3.00 minutes, hold on 95% mobile phase B for 1.00 minutes, and then 95-5% mobile phase B in 0.01 minute, the flow rate was 1.0 mL/minute. Mobile phase A was 0.037% Trifluoroacetic Acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000. |
| a | UPLC: The gradient was 5-95% mobile phase B over 3 minutes (0.77 mL/minute flow rate). Mobile phase A was 0.1% ammonium in water, mobile phase B was HPLC grade acetonitrile (MeCN). The column used for chromatography is a 2.1 × 30 mm Waters Acquity BEH C18. Detection methods are diode array (DAD) and evaporative light scattering (ELSD) as well as positive/negative electrospray ionization. |
| b | UPLC: The gradient was 5-95% mobile phase B over 3 minutes (0.77 mL/minute flow rate). Mobile phase A was 0.1% formic acid in water, mobile phase B was HPLC grade acetonitrile (MeCN) with 0.1% formic acid. The column used for chromatography is a 2.1 × 30 mm Waters Acquity CSH C18. Detection methods are diode array (DAD) and evaporative light scattering (ELSD) as well as positive/negative electrospray ionization. |
| c | HPLC: The gradient was 5% mobile phase B in 0.40 minutes and 5-95% mobile phase B at 0.40-3.00 minutes, hold on 95% mobile phase B for 1 minute, and then 95-5% mobile phase B in 0.01 minutes; the flow rate was 1.0 mL/minute. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000. |
| d | Reverse phase HPLC: The column used for chromatography was a Luna-C18 2.0*30 mm, (3 um particles). Detection methods are diode array (DAD). MS mode was positive electrospray ionization. MS range was 100-1000. Mobile phase A was 0.037% trifluoroacetic acid (TFA) in water, and mobile phase B was 0.018% TFA in HPLC grade acetonitrile. The gradient was 5-95% mobile phase B in 2 minutes 0.5% mobile phase B in 0.01 minutes, 5-95% mobile phase B (0.01-1.00 minutes), 95-100% mobile phase B (1.00-1.80 minutes), 5% mobile phase B in 1.81 minutes with a hold at 5% mobile phase B for 0.19 minutes. The flow rate was 1.0 mL/minutes (0.00-1.80 minutes) and 1.2 mL/minutes (1.81-2.00 minutes). |

Synthetic Intermediates

Preparation #1: (S)-1-Amino-3-phenylpropan-2-ol

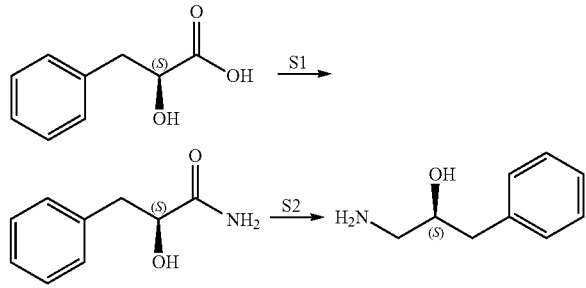

Step 1: (S)-2-Hydroxy-3-phenylpropanamide

Thionyl chloride (397 g, 3340 mmol) was added dropwise to methanol (1.50 L) cooled to about −20° C. (S)-2-hydroxy-3-phenylpropanoic acid (150 g, 903 mmol) was added, and the mixture was stirred at room temperature for about 2 hours. The mixture was concentrated in vacuo and the resulting crude acid chloride was added to a 7 N solution of ammonia in methanol (1.50 L, 903 mmol). The mixture was stirred at room temperature for about 12 hours, after which the mixture was concentrated in vacuo to provide the title product (140 g, 93% yield); $^1$H NMR (400 MHz, chloroform-d) δ 2.44 (br d, J=3.55 Hz, 1H), 2.85 (dd, J=13.94, 8.68 Hz, 1H), 3.18 (dd, J=13.94, 4.16 Hz, 1H), 4.20-4.32 (m, 1H), 5.46 (br s, 1H), 6.31 (br s, 1H), 7.15-7.34 (m, 5H).

Step 2: (S)-1-Amino-3-phenylpropan-2-ol

To a solution of (S)-2-hydroxy-3-phenylpropanamide (140 g, 848 mmol) in tetrahydrofuran (THF) (1.40 L) was added borane-dimethyl sulfide complex (424 mL, 4470 mmol) dropwise at room temperature. Once the addition was complete, the mixture was stirred at about 70° C. for about 12 hours. The mixture was then cooled to room temperature, carefully quenched with methanol (20 mL), and concentrated in vacuo to provide the title compound (105 g, 81% yield); $^1$H NMR (400 MHz, chloroform-d) δ 2.61 (dd, J=12.72, 8.07 Hz, 1H), 2.75-2.79 (m, 2H), 2.87 (dd, J=12.72, 3.42 Hz, 1H), 3.73-3.82 (m, 1H), 7.18-7.40 (m, 5H).

Preparation #2: (S)-1-(Methylamino)-3-phenylpropan-2-ol

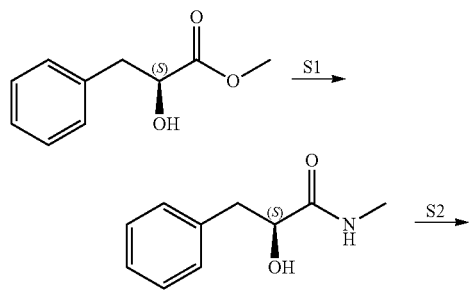

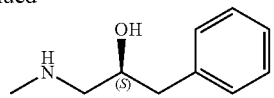

Step 1: (S)-2-Hydroxy-3-phenylpropanamide

To a solution of (S)-methyl 2-hydroxy-3-phenylpropanoate (110 g, 549 mmol) in methanol (1.00 L) at room temperature was added methylamine (1373 mL, 2747 mmol) dropwise. Once the addition was complete, the mixture was stirred at room temperature for about 8 hours. The mixture was concentrated under reduced pressure to give a crude oil which was then triturated with a mixture of petroleum ether/ethyl acetate (10:1; 800 mL) for about 4 hours. The resulting product was recovered by vacuum filtration and dried under vacuum to provide the title compound (80 g, 73%); $^1$H NMR (400 MHz, chloroform-d) δ 2.81 (d, J=5.01 Hz, 3H), 2.83-2.91 (m, 1H), 3.24 (dd, J=13.69, 3.91 Hz, 1H), 4.29 (dd, J=8.56, 3.91 Hz, 1H), 6.58 (br s, 1H), 7.23-7.30 (m, 3H), 7.31-7.37 (m, 2H).

Step 2: (S)-1-(Methylamino)-3-phenylpropan-2-ol

To a solution of (S)-2-hydroxy-N-methyl-3-phenylpropanamide (70 g, 391 mmol) in tetrahydrofuran (THF) (700 mL) was added borane-dimethyl sulfide complex (117 mL, 1172 mmol) dropwise at about 5° C. Once the addition was complete, the mixture was stirred at room temperature for about 1 hour, and then it was heated to about 70° C. and stirred for about 12 hours. The mixture was then cooled to about 10° C., and methanol (500 mL) was added dropwise while maintaining an internal temperature between about 10 to 30° C. Then a solution of HCl in methanol (4M, 2 L) was added dropwise and the resulting mixture was stirred at room temperature for about 12 hours. The mixture was concentrated, and the residue was partitioned between water (400 mL) and dichloromethane (DCM) (400 mL). The aqueous phase was washed with dichloromethane (DCM) (400 mL) and then neutralized to about pH=12 by slow addition of 6 N Aq (aqueous) NaOH. The aqueous solution was extracted with 2-methyl tetrahydrofuran (2-MeTHF) (3×400 mL). The combined organic phases were dried over Na$_2$SO$_4$, filtered and concentrated to give a residue, which was triturated with petroleum ether (120 mL) for 4 hours. The product was collected by filtration and concentrated to provide the title compound (54.9 g, 85%); $^1$H NMR (400 MHz, methanol-d$_4$) δ 2.35 (s, 3H), 2.47-2.60 (m, 2H), 2.71-2.76 (m, 2H), 3.90 (dtd, J=8.54, 6.64, 3.53 Hz, 1H), 7.10-7.32 (m, 5H).

Preparation #3: (1S,2R)-3-amino-1-fluoro-1-phenylpropan-2-ol

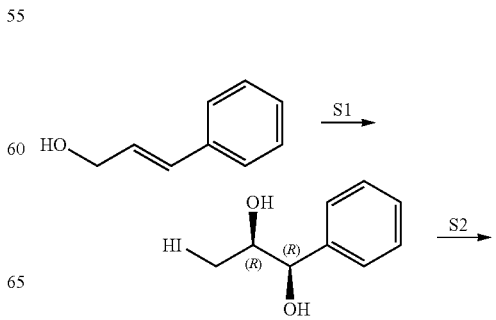

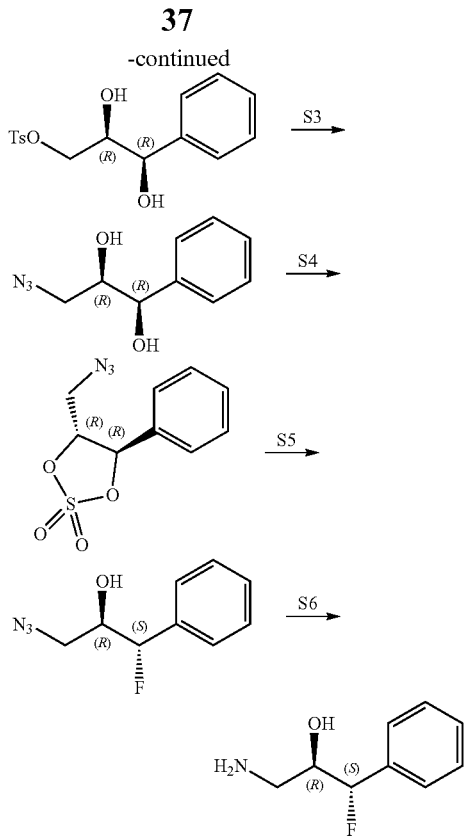

Step 1: (1R,2R)-1-phenylpropane-1,2,3-triol

To a mixture of cinnamyl alcohol (5.58 mL, 43.2 mmol), water (94 mL), tert-butanol (94 mL) cooled to about 0° C. was added Sharpless Asymmetric Dihydroxylation AD-MIX-BETA (62.5 g, 43.2 mmol) and methanesulfonamide (6.17 g, 64.8 mmol) and the mixture was stirred for about 16 hours. Added 10% aq. sodium thiosulfate (150 mL) and ethyl acetate (EtOAc) (125 mL) and stirred for about 30 min. The aqueous phase was extracted with EtOAc (2×125 mL). The combined organic phases were washed with brine, dried over $Na_2SO_4$, filtered, and concentrated under reduced pressure. The crude material was purified by flash column chromatography on silica gel eluting with 0-100% EtOAc/heptane to provide the title compound (4.5 g, 26.8 mmol, 61.9% yield); $^1H$ NMR (400 MHz, chloroform-d) δ ppm 3.21-3.30 (m, 1H) 3.37-3.55 (m, 2H) 3.69-3.77 (m, 1H) 3.79-4.05 (m, 2H) 4.61 (dd, J=6.79, 3.36 Hz, 1H) 7.27 (br s, 5H).

Step 2: (2R,3R)-2,3-dihydroxy-3-phenylpropyl 4-methylbenzenesulfonate

To a mixture of (1R,2R)-1-phenylpropane-1,2,3-triol (4.5 g, 26.8 mmol), in toluene (80 mL) was added dibutyltin oxide (0.133 g, 0.535 mmol). The mixture was heated to reflux for 20 minutes and the mixture was cooled to room temperature. Upon cooling, the mixture was concentrated under reduced pressure. Dry dichloromethane (DCM) (53.5 mL), p-toluenesulfonyl chloride (5.10 g, 26.8 mmol) and triethylamine (TEA) (3.73 mL, 26.8 mmol) were added and reaction was stirred at room temperature under N2 for about 16 hours. The mixture was quenched by adding water and the solution was extracted with DCM (3×75 mL). The combined organic phase was washed with water, dried ($Na_2SO_4$) and concentrated. The crude material was purified by flash column chromatography on silica gel eluting with 0-50% ethyl acetate (EtOAc)/heptane to provide the title compound (5.5 g, 17.06 mmol, 63.8% yield). $^1H$ NMR (400 MHz, chloroform-d) δ 3.81-3.98 (m, 2H), 4.00-4.10 (m, 1H), 4.03-4.09 (m, 1H), 4.10-4.17 (m, 1H), 4.67 (br d, J=5.07 Hz, 1H), 7.16-7.35 (m, 8H), 7.76 (d, J=7.94 Hz, 2H)

Step 3: (1R,2R)-3-azido-1-phenylpropane-1,2-diol

A mixture of (2R,3R)-2,3-dihydroxy-3-phenylpropyl 4-methylbenzenesulfonate (5.5 g, 17.06 mmol) and sodium azide (2.218 g, 34.1 mmol) in N,N-dimethylformamide (DMF) (85 mL) was heated at about 80° C. for about 3 hours. The reaction mixture was cooled and then partitioned between EtOAc (250 mL) and water (200 mL). After separating the layers, the aqueous phase was extracted with EtOAc (2×100 mL). The combined organic phases were washed with brine, dried over $Na_2SO_4$, filtered, and concentrated under reduced pressure. The crude material purified by flash column chromatography on silica gel eluted with 0%-100% EtOAc/heptane to provide the title compound (2.98 g, 90%); $^1H$ NMR (400 MHz, dimethylsulfoxide-$d_6$) δ 7.37-7.21 (m, 5H), 5.37 (dd, J=4.7, 0.9 Hz, 1H), 5.23 (d, J=5.6 Hz, 1H), 4.50 (t, J=5.0 Hz, 1H), 3.77-3.67 (m, 1H), 3.12 (dd, J=12.7, 3.3 Hz, 1H), 2.98 (dd, J=12.7, 7.8 Hz, 1H).

Step 4: (4S,5S)-4-(azidomethyl)-5-phenyl-1,3,2-dioxathiolane 2,2-dioxide

Thionyl chloride (2.252 mL, 30.8 mmol) was added to a solution of (1R,2R)-3-azido-1-phenylpropane-1,2-diol (2.98 g, 15.42 mmol) and pyridine (3.74 mL, 46.3 mmol) in dichloromethane (DCM) (154 mL) at about 0° C., and the mixture was stirred at about 0° C. for 1 hour. Saturated aqueous $CuSO_4$ (75 mL) was added, and the mixture was extracted with DCM (3×75 mL). The combined organic layers were washed with brine, dried ($Na_2SO_4$), filtered and concentrated. The resulting material was dissolved in acetonitrile (MeCN) (100 mL) and DCM (100 mL) and the solution was cooled to 0° C. Sodium periodate (6.53 g, 30.5 mmol), ruthenium(III) chloride hydrate (0.069 g, 0.305 mmol) and water (150 mL) were added, and the mixture was stirred at 0° C. for 2 hours. Diethyl ether (120 mL) was added, and the mixture was washed with water (50 mL), saturated aqueous $NaHCO_3$ (2×50 mL) and brine (2×50 mL). The organic layer was dried ($MgSO_4$) and concentrated to provide the title compound (3.5 g, 90%); $^1H$ NMR (400 MHz, chloroform-d) δ 7.52-7.42 (m, 5H), 5.76 (d, J=8.9 Hz, 1H), 4.91 (ddd, J=8.7, 4.4, 3.4 Hz, 1H), 3.79 (dd, J=14.3, 3.3 Hz, 1H), 3.54 (dd, J=14.3, 4.4 Hz, 1H).

Step 5: (1S,2R)-3-azido-1-fluoro-1-phenylpropan-2-ol

A mixture of tetra-N-butylammonium fluoride (TBAF) (78 mL, 78 mmol) and acetonitrile (MeCN), (100 mL) that had been dried over 4 Å molecular sieves was added to a solution of (4S,5S)-4-(azidomethyl)-5-phenyl-1,3,2-dioxathiolane 2,2-dioxide (10 g, 39.2 mmol) in MeCN (100 mL) at about 0° C. The resulting mixture was stirred at 0° C. for 1 hour. The reaction mixture was concentrated, and the resulting crude product was dissolved in tetrahydrofuran (THF) (100 mL). $H_2O$ (0.776 mL, 43.1 mmol) and $H_2SO_4$ (2.297 mL, 43.1 mmol) at 0° C. The resulting mixture was stirred at room temperature for about 12 hours. The resulting mixture was extracted with ethyl acetate (EtOAc) (150 mL×2). The organic phase was washed with brine (75 mL), dried over Na$_2$SO$_4$ and concentrated. The crude material was purified by flash column chromatography on silica gel eluted with 0-100% EtOAc/petroleum ether to provide the title compound (50 g, 35%). $^1$H NMR (400 MHz, chloroform-d) δ ppm: 2.00 (d, J=5.14 Hz, 1H) 3.53 (dd, J=5.01, 1.22 Hz, 2H) 4.02-4.11 (m, 1H) 5.27-5.52 (m, 1H) 7.37-7.46 (m, 5H).

Step 6: (1S,2R)-3-amino-1-fluoro-1-phenylpropan-2-ol

A 100 mL round-bottomed flask equipped with 3-way gas-tight stopcock was charged with (1S,2R)-3-azido-1-fluoro-1-phenylpropan-2-ol (0.684 g, 3.50 mmol) and Lindlar Catalyst (palladium, 5 wt % on calcium carbonate, poisoned with lead) (0.373 g, 0.175 mmol) in methanol (20 mL)). The resulting suspension was stirred under an atmosphere of hydrogen (balloon) at room temperature overnight. The suspension was filtered through a pad of Celite with methanol rinses and the filtrate was concentrated under reduced pressure to provide the title compound (0.55 g, 3.25 mmol, 93% yield). $^1$H NMR (400 MHz, chloroform-d) δ 7.46-7.26 (m, 5H), 5.40 (dd, J=46.8, 5.6 Hz, 1H), 3.88-3.76 (m, 1H), 2.99-2.81 (m, 2H), 1.78 (br s, 3H).

Preparation #4: (S)-1-(3-fluorophenyl)-3-(methylamino)propan-2-ol

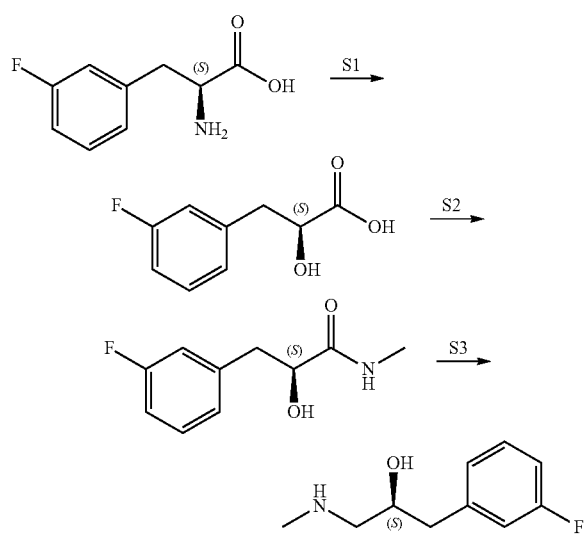

Step 1: (S)-3-(3-fluorophenyl)-2-hydroxypropanoic acid

A solution of NaNO$_2$ (2.26 g, 32.8 mmol) in H$_2$O (21.6 mL) was added dropwise to a stirred solution of (S)-2-amino-3-(3-fluorophenyl)propanoic acid (2.0 g, 10.92 mmol) in H$_2$O (50 mL) and acetic acid (AcOH) (15 mL) at about 0° C. The mixture was warmed to room temperature and stirred for about 20 hours. Methylamine (2 M in tetrahydrofuran (THF), 22 mL, 43.7 mmol) was added dropwise and the mixture was stirred at room temperature for about 1 hour. The mixture was then concentrated in vacuo to remove the THF and the resulting aq mixture was extracted into ethyl acetate (EtOAc) (3×30 mL). The combined organic layers were washed with saturated aq NaCl (30 mL), dried over MgSO$_4$ and concentrated in vacuo to provide the title compound (20.11 g, 100% yield); $^1$H NMR (500 MHz, chloroform-d) δ 7.32-7.26 (m, 1H), 7.09-6.95 (m, 3H), 4.53 (dd, J=7.1, 4.2 Hz, 1H), 3.21 (dd, J=14.1, 4.2 Hz, 1H), 3.01 (dd, J=14.1, 7.0 Hz, 1H).

Step 2: (S)-3-(3-fluorophenyl)-2-hydroxy-N-methylpropanamide

Thionyl chloride (2.87 mL, 39.3 mmol) was added dropwise to methanol (10 mL) at about −20° C. and a solution of (S)-3-(3-fluorophenyl)-2-hydroxypropanoic acid (2.01 g, 10.91 mmol) in methanol (5.00 mL) was added. The mixture was stirred at room temperature for about 2 hours. The mixture was concentrated in vacuo and the residue was taken up in methylamine (33% in ethanol, 14 mL, 109 mmol) and stirred at room temperature for about 2 hours. The solvent was removed in vacuo and the residue was purified by flash chromatography on silica gel (0-10% methanol/DCM) to provide the title compound (1.67 g, 70% yield); LC/MS (Table B, Method ee) R$_t$=1.15 min; MS m/z 198 (M+H)$^+$.

Step 3: (S)-1-(3-fluorophenyl)-3-(methylamino)propan-2-ol

A solution of (S)-3-(3-fluorophenyl)-2-hydroxy-N-methylpropanamide (1.67 g, 8.47 mmol) in tetrahydrofuran (THF) (45 mL) was heated to about 65° C. and borane dimethyl sulfide complex (BH$_3$·SMe$_2$) (2.4 mL, 25.4 mmol) was added. The resulting mixture was stirred for about 3 hours. The reaction mixture was cooled to room temperature and quenched via the dropwise addition of methanol (15 mL) and the solvents were removed in vacuo. The residue was loaded onto a column of Strong Cation Exchange (SCX) and washed with methanol (100 mL). The product was eluted with 0.7 M NH$_3$ in methanol (100 mL) and the solvent was removed in vacuo to provide the title compound (999 mg, 61%); LC/MS (Table B, Method ee) R$_t$=0.32 min; MS m/z 184 (M+H)$^+$.

Preparation #5: 3-bromo-6,7-dihydro-4H-pyrazolo[5,1-c][1,4]oxazine

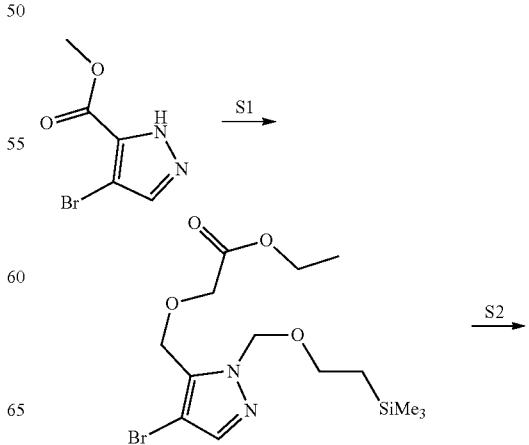

41

-continued

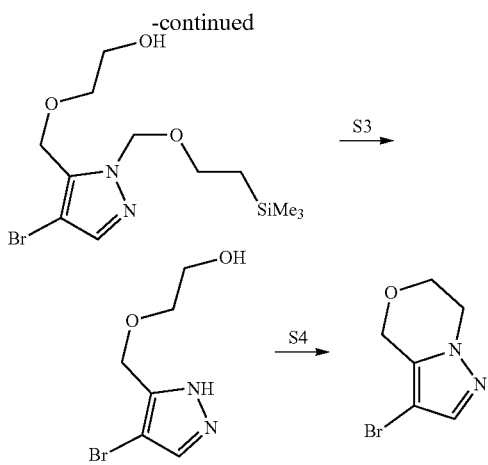

Step 1: ethyl 2-((4-bromo-1-((2-(trimethylsilyl)ethoxy)methyl)-1H-pyrazol-3-yl)methoxy)acetate Methyl 4-bromo-1H-pyrazole-5-carboxylate (10.0 g, 48.8 mmol) was added in portions to a suspension of sodium hydride (60% in mineral oil) (2.05 g, 51.2 mmol) in N,N-dimethylformamide (DMF) (200 mL) stirring at about 0° C. The resulting suspension was stirred at about 0° C. for about 15 minutes, at which point 2-(trimethylsilyl)ethoxymethyl chloride (10.4 mL, 58.5 mmol) was added dropwise (Me=methyl). The resulting solution was stirred at about 0° C. for about 1 hour. The reaction was quenched with ice water (250 mL) and extracted with ethyl acetate (EtOAc) (3×100 mL). The combined organic phases were washed with brine (250 mL), dried over Na$_2$SO$_4$, filtered, and concentrated under reduced pressure. The resulting product mixture was dissolved in tetrahydrofuran (THF) (50.0 mL) and added dropwise to a stirred mixture of lithium aluminum hydride (LAH) (1.37 g, 36.1 mmol) in THF (150 mL) cooled at about 0° C. The resulting suspension was stirred at about 0° C. for about 2 h. The reaction mixture was quenched at 0° C. by careful addition of water (1.5 mL), followed by 5 N aq. NaOH (1.5 mL) and more water (3 mL). The mixture was diluted with diethyl ether (100 mL), MgSO$_4$ (about 25 g) was added and the suspension was stirred for about 30 minutes. The reaction mixture was filtered through a pad of Celite, rinsed with EtOAc. The filtrate was concentrated, and the residue was purified by flash column chromatography on silica gel eluted with 0-50% EtOAc/heptane to give a mixture of products (10.7 g). The mixture was dissolved in in THF (174 mL), ethyl bromoacetate (6.11 g, 36.6 mmol) was added and the solution was cooled to about 0° C. Sodium hydride (60% in mineral oil) (1.46 g, 36.6 mmol) was added and the resulting suspension was stirred at about 0° C. for about 3 hours. Stirring was continued for about 16 hours at room temperature, after which the reaction was cooled to about 0° C. and quenched with water (about 50 mL). The mixture was extracted with EtOAc (3×75 mL) and the combined organic phases were washed with brine, dried over Na$_2$SO$_4$, filtered, and concentrated under reduced pressure. The crude material was purified by flash column chromatography on silica gel eluted with 0-50% EtOAc/heptane to provide the title compound (7.76 g, 56.7% yield); $^1$H NMR (400 MHz, chloroform-d) δ 7.48 (s, 1H), 5.51-5.66 (m, 2H), 4.76 (s, 2H), 4.23 (q, J=7.21 Hz, 2H), 4.03-4.12 (m, 2H), 3.51-3.64 (m, 2H), 1.30 (t, J=7.09 Hz, 3H), 0.82-0.96 (m, 2H), 0.02 (s, 9H).

42

Step 2: 2-((4-bromo-1-((2-(trimethylsilyl)ethoxy)methyl)-1H-pyrazol-3-yl)methoxy)ethanol To a suspension of lithium aluminum hydride (LAH) (0.562 g, 14.8 mmol) in tetrahydrofuran (THF) (80 mL) cooled in ice bath was added a solution of ethyl 2-((4-bromo-1-((2-(trimethylsilyl)ethoxy)methyl)-1H-pyrazol-3-yl)methoxy)acetate (7.76 g, 19.73 mmol) in THF (20 mL) and the resulting solution was stirred for about 20 minutes. Water (about 0.5 mL) was added, followed by 5 N aq. NaOH (0.5 mL), additional water (about 1 mL) and diethyl ether (50 mL). The mixture was stirred for about 10 minutes; MgSO$_4$ (about 20 g) was added and the suspension stirred for 30 minutes. The suspension was filtered through a pad of Celite which was washed with ethyl acetate (EtOAc). The combined filtrate was concentrated under reduced pressure to provide the title compound (6.83 g, 99% yield); $^1$H NMR (400 MHz, chloroform-d) δ 7.59 (s, 1H), 5.37 (s, 2H), 4.60 (s, 2H), 3.71-3.77 (m, 2H), 3.63-3.67 (m, 2H), 3.52-3.60 (m, 2H), 2.37 (br t, J=6.11 Hz, 1H), 0.85-0.97 (m, 2H), 0.03-0.01 (m, 9H).

Step 3: 2-((4-bromo-1H-pyrazol-3-yl)methoxy)ethanol

A solution of 2-((4-bromo-1-((2-(trimethylsilyl)ethoxy)methyl)-1H-pyrazol-3-yl)methoxy)ethanol (6.83 g, 19.4 mmol) in ethanol (100 mL) was treated with concentrated aq HCl (39 mL, 78 mmol) and the solution was heated at about 60° C. After about 20 hours, the reaction was cooled to room temperature and was then concentrated under reduced pressure. Saturated aq NaHCO$_3$ solution (75 mL) was added and the mixture was stirred for about 20 minutes. The mixture was extracted with ethyl acetate (EtOAc) (3×50 mL) and the combined organic phases were washed with brine, dried over Na$_2$SO$_4$, filtered, and concentrated under reduced pressure to provide the title compound (3.87 g, 90% yield). $^1$H NMR (400 MHz, chloroform-d) δ 7.52 (s, 1H), 4.62 (s, 2H), 3.77-3.81 (m, 2H), 3.65-3.68 (m, 2H).

Step 4: 3-bromo-6,7-dihydro-4H-pyrazolo[5,1-c][1,4]oxazine

A solution of 2-((4-bromo-1H-pyrazol-3-yl)methoxy)ethanol (0.250 g, 1.13 mmol) and tri-N-butylphosphine (0.558 mL, 2.26 mmol) in toluene (12 mL) at about 50° C. was treated with N,N,N',N'-tetramethylazodicarboxamide (0.389 g, 2.26 mmol) added dropwise via syringe. The resulting solution was stirred at room temperature for about 20 minutes, after which the reaction was quenched with water (1 mL). The reaction mixture was concentrated under reduced pressure and the residue was purified by flash column chromatography on silica gel eluted with 0-100% ethyl acetate (EtOAc)/heptane to provide the title compound (0.103 g, 45% yield); $^1$H NMR (400 MHz, chloroform-d) δ 7.46 (s, 1H), 4.76 (s, 2H), 4.14-4.20 (m, 2H), 4.07-4.13 (m, 2H).

Preparation #6: (S)-5-chloro-6-(difluoromethyl)-N-(2-hydroxy-3-phenylpropyl)-N-methylnicotinamide

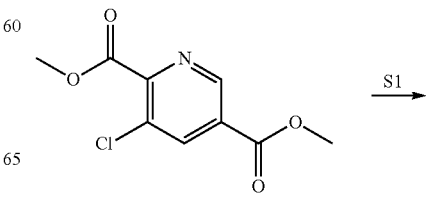

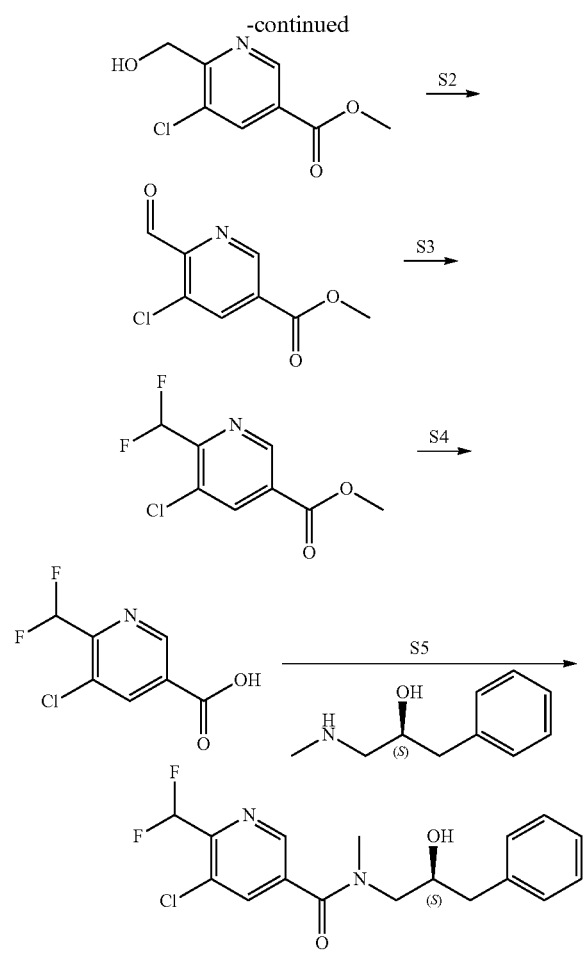

Step 1: methyl 5-chloro-6-(hydroxymethyl)nicotinate

Dimethyl 3-chloropyridine-2,5-dicarboxylate (2.0 g, 8.71 mmol) was dissolved in tetrahydrofuran (THF)/methanol (1:2, 60 mL) and cooled to about 0° C. CaCl$_2$) (7.8 g, 70 mmol) was added and the reaction mixture was stirred for about 30 minutes. Sodium borohydride (NaBH$_4$) (0.832 g, 22 mmol) was added portion wise and the reaction was stirred at about 0° C. for about 3 hours. The reaction was diluted with dichloromethane (DCM) (50 mL) and poured into ice cold H$_2$O (100 mL). Layers were separated and the aq layer was extracted into DCM (2×25 mL). The combined organic phase was washed with saturated aq NaCl (2×25 mL), dried over MgSO$_4$ and the solvents were removed in vacuo to provide the title compound (1.0 g, 54% yield). $^1$H NMR (500 MHz, dimethylsulfoxide-d$_6$) δ 9.00 (d, J=1.8 Hz, 1H), 8.29 (d, J=1.8 Hz, 1H), 5.42 (t, J=6.0 Hz, 1H), 4.71 (d, J=6.1 Hz, 2H), 3.91 (s, 3H).

Step 2: Methyl 5-bromo-6-formylnicotinate

To a solution of methyl 5-bromo-6-(hydroxymethyl)nicotinate (0.723 g, 2.94 mmol) in dichloromethane (DCM) (10 mL) was added Dess-Martin periodinane (1.87 g, 4.41 mmol) and the reaction mixture stirred for about 18 hours at room temperature. To this was added a mixture of saturated aq NaHCO$_3$/1M aq Na$_2$S2O3 (1:1, 50 mL) and the biphasic mixture was stirred until clear. The phases were separated, and the aq phase was washed with dichloromethane (DCM) (2×50 mL). The combined organic phase was dried over MgSO$_4$ and the solvents were removed in vacuo to provide the title compound (0.623 g, 83% yield). $^1$H NMR (500 MHz, dimethylsulfoxide-d$_6$) δ 10.16 (s, 1H), 9.18 (d, J=1.8 Hz, 1H), 8.48 (d, J=1.5 Hz 1H), 3.95 (s, 3H).

Step 3: Methyl 5-chloro-6-(difluoromethyl)nicotinate

To a stirred solution of methyl 5-chloro-6-formylnicotinate (0.623 mg, 3.12 mmol) in chloroform (30 mL) was added Deoxo-Fluor® (50% in toluene, 2.9 mL, 7.80 mmol) and the mixture stirred at about 45° C. for about 24 hours. The reaction was quenched via the addition of saturated aq NaHCO$_3$ (10 mL), diluted with H$_2$O (10 mL) and extracted into dichloromethane (DCM) (3×10 mL). The combined organic layer was dried over MgSO$_4$, filtered and the solvents were removed in vacuo. The residue was purified via flash column chromatography on silica gel eluting with 0-60% ethyl acetate (EtOAc)/isohexane to provide the title compound (0.433 g, 60% yield). $^1$H NMR (500 MHz, dimethylsulfoxide-d$_6$) δ 9.10 (d, J=1.8 Hz, 1H), 8.50 (d t, J=1.7, 0.8 Hz, 1H), 7.28 (t, J=52.9 Hz, 1H), 3.94 (s, 3H).

Step 4: 5-chloro-6-(difluoromethyl)nicotinic acid

Methyl 5-chloro-6-(difluoromethyl) nicotinate (0.200 g, 0.71 mmol) was suspended in methanol (2 mL) and 2M aq NaOH (1 mL, 2.00 mmol) was added. The reaction mixture was stirred at room temperature for about 3 hours. Aq 1M HCl was added dropwise until pH 2 and the mixture was extracted into ethyl acetate (EtOAc) (3×5 mL). The combined organic phase was dried over MgSO$_4$ and the solvents were removed in vacuo to provide the title compound (0.141 g, 91% yield). $^1$H NMR (500 MHz, dimethylsulfoxide-d$_6$) δ 14.03 (s, 1H), 9.08 (d, J=1.7 Hz, 1H), 8.46 (d, J=1.8 Hz, 1H), 7.27 (t, J=53.0 Hz, 1H).

Step 5: (S)-5-chloro-6-(difluoromethyl)-N-(2-hydroxy-3-phenylpropyl)-N-methylnicotinamide A mixture of 5-chloro-6-(difluoromethyl)nicotinic acid (0.141 g, 0.68 mmol), (S)-1-(methylamino)-3-phenylpropan-2-ol (0.123 mg, 0.75 mmol) (Preparation #2), 4-methylmorpholine (0.187 mL, 1.70 mmol), 1-(3-dimethylaminopropyl)-3-ethylcarbodiimide hydrochloride (EDC.HCl) (195 mg, 1.02 mmol) and 1-hydroxybenzotriazole (HOBt) hydrate (156 mg, 1.02 mmol) were dissolved in N,N-dimethylformamide (DMF) (5 mL) and stirred at room temperature for about 18 hours. The reaction mixture was diluted with ethyl acetate (EtOAc) (10 mL) and washed sequentially with saturated aq NH$_4$Cl (10 mL), saturated aq NaHCO$_3$ (10 mL) and saturated aq NaCl (3×10 mL). The organic phase was dried over MgSO$_4$ and the solvents were removed in vacuo. The crude residue was used without further purification. LC/MS (Table B, Method dd) R$_t$=1.89 min; MS m/z: 355 (M+H)$^+$.

Preparation #7: 4-Bromo-2-(oxetan-3-yl)-2H-1,2,3-triazole

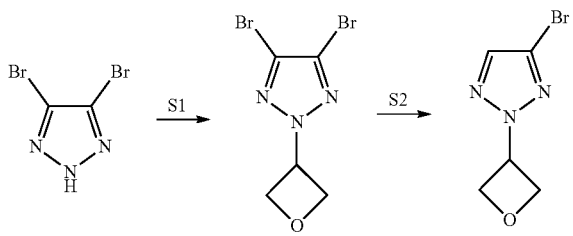

Step 1: 4,5-Dibromo-2-(oxetan-3-yl)-2H-1,2,3-triazole

To a mixture of 4,5-dibromo-2H-1,2,3-triazole (500 mg, 2.20 mmol) and 3-iodooxetane (0.213 mL, 2.42 mmol) in N,N-dimethylformamide (DMF) (20 mL) was added Cs$_2$CO$_3$ (2.1 g, 6.45 mmol). The mixture was stirred at about 120° C. for about 18 hours. The mixture was cooled to room temperature, diluted with ethyl acetate (EtOAc) (200 mL) and washed with H$_2$O (3×100 mL), saturated aq NaCl (2×200 mL), dried over MgSO$_4$, filtered and concentrated in vacuo. The material was purified by flash chromatography on silica gel (0-100% EtOAc/isohexane) to provide the title compound (529 mg, 81% yield); $^1$H NMR (500 MHz, dimethylsulfoxide-d$_6$) δ 5.90-5.81 (m, 1H), 4.97 (t, J=7.4 Hz, 2H), 4.88 (t, J=6.5 Hz, 2H).

Step 2: 4-Bromo-2-(oxetan-3-yl)-2H-1,2,3-triazole

To a vial was added 4,5-dibromo-2-(oxetan-3-yl)-2H-1,2,3-triazole (250 mg, 0.88 mmol) and tetrahydrofuran (THF) (4 mL). The mixture was cooled to about −30° C. Isopropylmagnesium chloride (iPrMgCl) (2M in THF, 1.3 mL, 2.65 mmol) was added dropwise, and the mixture warmed to room temperature over about 3 hours. The mixture was quenched with saturated aq NH$_4$Cl (20 mL) and the aq layer was extracted into ethyl acetate (EtOAc) (3×20 mL). The organic layer was washed with saturated aq NaCl (2×50 mL), dried over MgSO$_4$, filtered and the solvents were evaporated in vacuo to provide the title compound (125 mg, 56% yield); $^1$H NMR (500 MHz, dimethylsulfoxide-d$_6$) δ 8.11 (s, 1H), 5.90-5.82 (m, 1H), 5.01-4.95 (m, 2H), 4.91-4.86 (m, 2H).

Preparation #8: (S)-5-bromo-N-(2-hydroxy-3-phenylpropyl)-N-methylnicotinamide

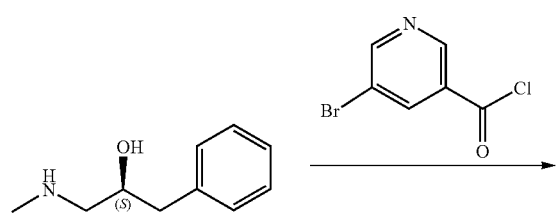

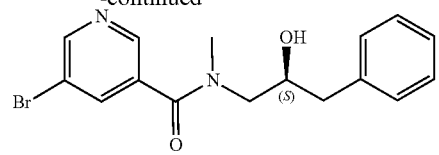

To a stirred suspension of 5-bromonicotinic acid (7.52 g, 37.2 mmol) in dichloromethane (DCM) (130 mL) and N,N-dimethylformamide (DMF) (200 µL) was added a solution of oxalyl chloride in dichloromethane (DCM) (2M; 37.2 mL, 74.5 mmol). The mixture was stirred at room temperature for about 2 hours, after which it was concentrated under vacuum. The residue was dissolved in tetrahydrofuran (THF) (150 mL) and the resulting mixture was cooled in an ice bath before adding a mixture of (S)-1-(methylamino)-3-phenylpropan-2-ol (Preparation #2) (6.15 g, 37.2 mmol) and N,N-Diisopropylethylamine (DIEA) (19.5 mL, 112 mmol) in THF (20 mL). The reaction mixture was stirred at room temperature for about 1 hour, after which ethyl acetate (EtOAc) (50 mL), methyl tert-butyl ether (MTBE) (50 mL) and NaHCO$_3$ (100 mL) were added. The layers were separated, and the organics were concentrated under vacuum. The resulting crude material was purified by flash column chromatography on silica gel eluting with a gradient of 0-100% EtOAc/heptane to provide the title compound (11 g, 85% yield); $^1$H NMR at 90° C. (500 MHz, dimethylsulfoxide-d$_6$) δ 8.70 (d, J=2.3 Hz, 1H), 8.54 (d, J=1.9 Hz, 1H), 8.01 (t, J=2.0 Hz, 1H), 7.21 (d t, J=31.1, 7.5 Hz, 5H), 4.76 (s, 1H), 4.02 (s, 1H), 3.27 (d, J=21.5 Hz, 2H), 3.00 (s, 3H), 2.65 (s, 2H).

Preparation #9: (S)-5-ethynyl-N-(2-hydroxy-3-phenylpropyl)-N-methylnicotinamide

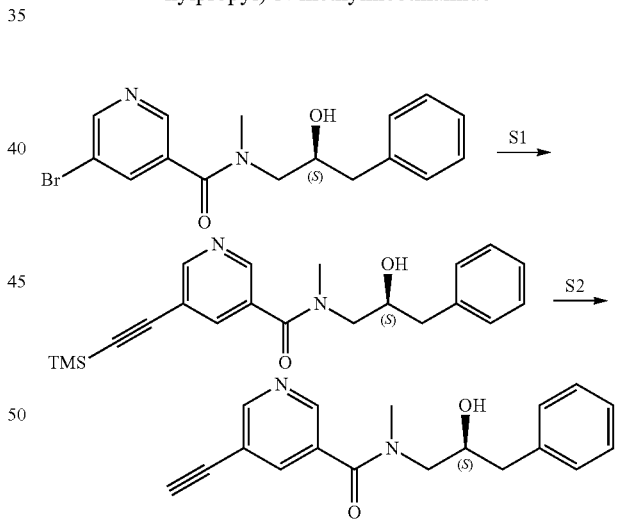

Step 1: (S)-N-(2-hydroxy-3-phenylpropyl)-N-methyl-5-((trimethylsilyl)ethynyl) nicotinamide A mixture of (S)-5-bromo-N-(2-hydroxy-3-phenylpropyl)-N-methylnicotinamide (4.0 g, 8.93 mmol) (Preparation #8), ethynyltrimethylsilane (2.5 mL, 17.87 mmol), bis(triphenyl-phosphine)-palladium (II) dichloride (Pd(PPh$_3$)$_2$Cl$_2$) (0.753 g, 1.07 mmol), CuI (0.340 g, 1.79 mmol) and Et$_3$N (8.7 mL, 62.5 mmol) in N,N-dimethylformamide (DMF) (60 mL) were sparged with N2 then heated to about 90° C. for about 2 hours. The mixture was cooled to room temperature, filtered through Celite and washed with ethyl acetate (EtOAc) (200 mL). The filtrate was diluted with EtOAc (200 mL) and H₂O (600 mL) and the layers were separated. The aq layer was extracted into EtOAc (2×300 mL) and the combined organic layer was washed with saturated aq NaCl (2×300 mL), dried over MgSO₄, filtered, and concentrated in vacuo. The resulting material was purified by flash chromatography on silica gel (0-100% EtOAc/isohexane) to provide the title compound (3.3 g, 91% yield); LC/MS (Table B, Method ee) $R_t$=2.35 min; MS m/z 367 (M+H)⁺.

Step 2: (S)-5-ethynyl-N-(2-hydroxy-3-phenylpropyl)-N-methylnicotinamide

To a stirred solution of (S)-N-(2-hydroxy-3-phenylpropyl)-N-methyl-5-((trimethylsilyl)ethynyl)nicotinamide (3.3 g, 9.00 mmol) in tetrahydrofuran (THF) (30 mL) was added tetra-N-butylammonium fluoride (TBAF) (1 M in THF) (11.70 mL, 11.70 mmol) and the mixture was stirred at room temperature for about 1 hour. The mixture was taken up in ethyl acetate (EtOAc) (150 mL) and washed with H₂O (150 mL) and saturated aq NaCl (150 mL), dried over MgSO₄, filtered and concentrated in vacuo to give a brown oil which was purified by flash chromatography on silica gel (0-100% EtOAc/isohexane) to provide the title compound (2.3 g, 76% yield); LC/MS (Table B, Method ee) $R_t$=1.65 min; MS m/z 295 (M+H)⁺.

Preparation #10: 4-ethynyl-1-methyl-1H-pyrazole

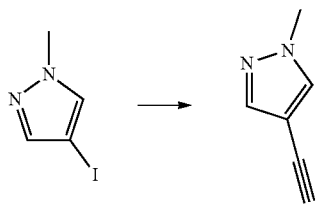

To a solution of 4-iodo-1-methyl-1H-pyrazole (20 g, 96 mmol) in N,N-dimethylformamide (DMF) (120 mL) was added ethynyltrimethylsilane (13.2 g, 135 mmol), copper(I) iodide (1.282 g, 6.73 mmol), triphenylphosphine (PPh₃) (5.04 g, 19.23 mmol), diisopropylamine (12.6 g, 125 mmol) and Palladium(II) acetate (Pd(OAc)₂) (1.30 g, 5.77 mmol). The mixture was stirred under N2 at about 60° C. for about 1 hour. After cooling to room temperature, the mixture was poured into water (200 mL) and extracted with ethyl acetate (EtOAc) (3×200 mL). The organic layer was combined and washed with brine (200 mL), dried over Na₂SO₄, filtered and concentrated under reduced pressure. The residue was triturated with methyl tert-butyl ether (MTBE) and the resulting suspension was filtered to remove solids. The solids were rinsed with methyl tert-butyl ether (MTBE) and the combined filtrate was concentrated under vacuum. The resulting crude product was dissolved in methanol (200 mL), K₂CO₃ (1.55 g, 11.2 mmol) was added and the mixture was stirred at room temperature for about 1 hour. This mixture was poured into water (200 mL) and extracted with EtOAc (3×100 mL). The organic layer was combined and washed with brine (100 mL), dried over Na₂SO₄, filtered and concentrated under reduced pressure. The resulting crude material was purified by column chromatography on silica gel eluting with 0-25% EtOAc/petroleum ether to provide the title compound (5.0 g, 42% yield). ¹H NMR (400 MHz, chloroform-d) δ 3.00 (s, 1H), 3.89 (s, 3H), 7.49-7.54 (m, 1H), 7.60 (s, 1H).

Preparation #11: 6-methyl-5-((1-methyl-1H-pyrazol-4-yl)ethynyl)nicotinic acid

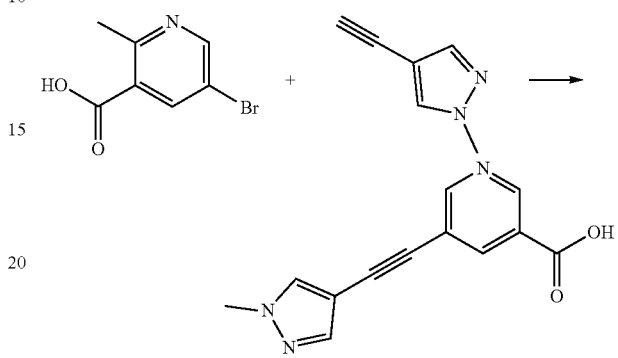

A mixture of 4-ethynyl-1-methyl-1H-pyrazole (Preparation #10) (1.175 g, 9.96 mmol), 5-bromo-6-methylnicotinic acid (2.080 g, 9.63 mmol), methanesulfonato(2-dicyclohexylphosphino-2',4',6'-tri-i-propyl-1,1'-biphenyl)(2'-amino-1,1'-biphenyl-2-yl)palladium(II) (XPhos Pd G³) (0.060 g, 0.071 mmol) and Cs₂CO₃ (3.760 g, 11.54 mmol) in N,N-dimethylformamide (DMF) (20 mL) was sparged with N2 for about 5 minutes. The reaction mixture was stirred under N2 at about 70° C. for about 3 hours. The reaction mixture was cooled to room temperature, water (40 mL) was added, and the mixture was acidified to pH~2 with 1 M HCl (aq) (~20 mL). The precipitate was filtered, and the solids were then washed with water (30 mL) and dried in a vacuum oven to provide the title compound (2.18 g, 89% yield). ¹H NMR (500 MHz, dimethylsulfoxide-d₆) δ 13.45 (s, 1H), 8.87 (d, J=2.1 Hz, 1H), 8.17 (d, J=2.2 Hz, 1H), 8.15 (s, 1H), 7.75 (d, J=0.7 Hz, 1H), 3.87 (s, 3H), 2.68 (s, 3H).

Preparation #12: 5-((1-Methyl-1H-pyrazol-4-yl)ethynyl)nicotinic acid

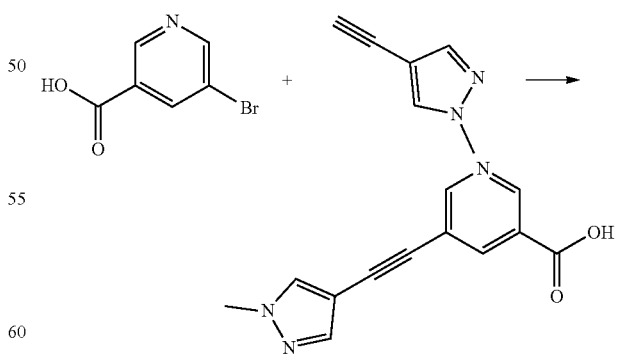

5-Bromonicotinic acid (1.59 g, 7.87 mmol), 2-dicyclohexylphosphino-2',4',6'-triisopropylbiphenyl (X-Phos) (0.375 g, 0.79 mmol), bis(acetonitrile)dichloropalladium (II) (Pd(MeCN)₂Cl₂) (0.102 g, 0.39 mmol) and Cs₂CO₃ (3.1 g, 9.45 mmol) were added to a flask and taken up in N,N- dimethylformamide (DMF) (30 mL). 4-Ethynyl-1-methyl-1H-pyrazole (Preparation #10) (1.0 g, 9.45 mmol) in DMF (5 mL) was added and the reaction mixture was stirred for about 3 hours at about 70° C. The mixture was cooled to room temperature and the solvent removed in vacuo. The residue was diluted with H$_2$O (60 mL) and ethyl acetate (EtOAc) (60 mL). Layers were separated and the aq phase was acidified to pH 2 with 1M aq HCl. The resulting solid was filtered and dried to provide the title compound (1.66 g, 90% yield); LC/MS (Table B, Method ee) R$_t$=1.42 min; MS m/z 228 (M+H)$^+$.

Preparation #13: 5-((1-(difluoromethyl)-1H-pyrazol-4-yl)ethynyl)nicotinic acid

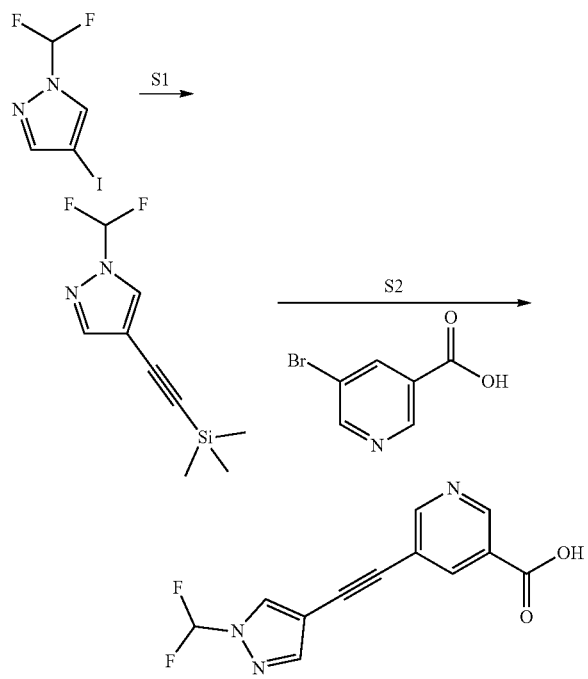

Step 1: 1-(difluoromethyl)-4-((trimethylsilyl)ethynyl)-1H-pyrazole

A suspension of 1-(difluoromethyl)-4-iodo-1H-pyrazole (10.0 g, 41.0 mmol), ethynyltrimethylsilane (6.04 g, 61.5 mmol) and methanesulfonato(2-dicyclohexylphosphino-2',4',6'-tri-i-propyl-1,1'-biphenyl)(2'-amino-1,1'-biphenyl-2-yl)palladium(II) (XPhos Pd G$^3$) (0.173 g, 0.205 mmol) in tetrahydrofuran (THF) (100 mL) was sparged with N2 for about 15 min. Diisopropylamine (11.68 mL, 82 mmol) and copper (I) iodide (0.020 g, 0.10 mmol) were added. The resulting mixture was stirred for about 12 h at about 65° C. The mixture was diluted with methyl tert-butyl ether (MTBE)/Ethyl acetate (EtOAc) (1:1; 50 mL) and washed with water (100 mL) and sat. NaCl (100 mL). The organic layer was dried over Na$_2$SO$_4$, filtered and concentrated. The crude material was distilled by vacuum distillation at about 160° C. to provide the title compound (4.0 g, 44% yield); $^1$H NMR (400 MHz, chloroform-d) δ 0.21-0.28 (m, 9H), 6.94-7.36 (m, 1H), 7.69-7.77 (m, 1H), 7.95 (s, 1H).

Step 2: 5-((1-(difluoromethyl)-1H-pyrazol-4-yl)ethynyl)nicotinic acid

A mixture of 1-(difluoromethyl)-4-((trimethylsilyl)ethynyl)-1H-pyrazole (73.8 g, 317 mmol), 5-bromonicotinic acid (40 g, 198 mmol), Cs$_2$CO$_3$ (77 g, 238 mmol) and methanesulfonato(2-dicyclohexylphosphino-2',4',6'-tri-i-propyl-1,1'-biphenyl)(2'-amino-1,1'-biphenyl-2-yl)palladium(II) (XPhos Pd G3) (1.676 g, 1.980 mmol) in N,N-dimethylformamide (DMF) (500 mL) were stirred under a N$_2$ sparge for about 10 min., after which tetrabutylammonium fluoride (218 mL, 218 mmol) was added and the mixture was stirred under N$_2$ at about 60° C. for about 12 h. The mixture was concentrated under reduced pressure and diluted with water (500 mL). The aqueous phase was extracted with methyl tertiary butyl ether (3×250 mL), and then the aqueous layer was adjusted to a pH of about 3 with 5N aq HCl. The resulting solids were collected via vacuum filtration and dried under vacuum to provide the title compound (47.5 g, 91% yield); $^1$H NMR (400 MHz, dimethylsulfoxide-d$_6$) δ=14.40-12.47 (m, 1H), 9.04 (d, J=2.0 Hz, 1H), 8.92 (d, J=2.5 Hz, 1H), 8.73 (s, 1H), 8.31 (t, J=2.3 Hz, 1H), 8.12 (s, 1H), 8.02-7.70 (m, 1H).

Preparation #14: 5-((2-methyl-2H-1,2,3-triazol-4-yl)ethynyl)nicotinic acid

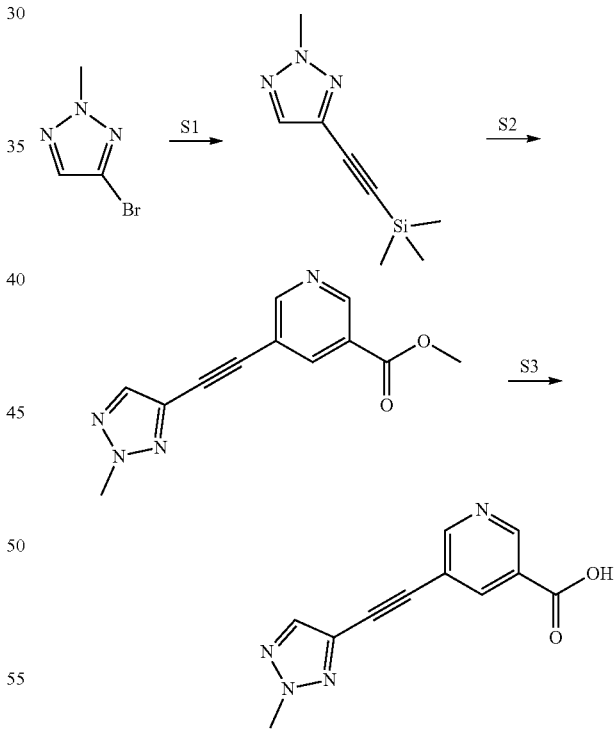

Step 1: 2-methyl-4-((trimethylsilyl)ethynyl)-2H-1,2,3-triazole

A mixture of 4-bromo-2-methyl-2H-1,2,3-triazole (500 mg, 3.09 mmol), ethynyltrimethylsilane (1.283 mL, 9.26 mmol), triethylamine (TEA) (0.860 mL, 6.17 mmol), Copper (I) iodide (29.4 mg, 0.154 mmol) and tetrakis(triphenylphosphine)palladium(0) (Pd(PPh$_3$)$_4$) (178 mg, 0.154 mmol) in N,N-dimethylformamide (DMF) (6 mL) was degassed with $N_2$ for 5 minutes, then heated to about 100° C. for about 1 hour. The mixture was concentrated in vacuo and purified by flash column chromatography on silica gel eluting with 0-50% yield ethyl acetate (EtOAc)/iso-hexane to provide the title compound (438 mg, 63% yield); $^1$H NMR (500 MHz, chloroform-d) δ 7.63 (s, 1H), 4.17 (s, 3H), 0.25 (s, 9H).

Step 2: methyl 5-((2-methyl-2H-1,2,3-triazol-4-yl)ethynyl)nicotinate

To a vial containing methyl 5-bromonicotinate (1.142 g, 5.29 mmol), 2-methyl-4-((trimethylsilyl)ethynyl)-2H-1,2,3-triazole (1.517 g, 6.35 mmol), triethylamine (TEA) (5.16 mL, 37.0 mmol), Copper (I) iodide (0.101 g, 0.529 mmol) and bis(triphenylphosphine)palladium (II) dichloride (Pd(PPh$_3$)$_2$Cl$_2$) (0.371 g, 0.529 mmol) was added N,N-dimethylformamide (DMF) (15 mL) and the mixture degassed with nitrogen for 5 minutes, then tetra-N-butylammonium fluoride (TBAF) 1 M in tetrahydrofuran (THF) (7.93 mL, 7.93 mmol) was added and the mixture degassed for 30 seconds then heated to 100° C. for 1 hour. The mixture was concentrated, then taken into ethyl acetate (EtOAc) (100 mL) and washed with saturated sodium bicarbonate (aq) (100 mL). The aqueous layer was further extracted with EtOAc (2×50 mL), and the combined organic layers washed with water (100 mL). The organic layer was dried using Na$_2$SO$_4$, filtered and concentrated to give a brown oil, which was purified by flash column chromatography on silica gel eluting with 0-60% EtOAc/Isohexane to provide the title compound (0.978 g, 69% yield); $^1$H NMR (500 MHz, chloroform-d) δ 9.17 (d, J=2.1 Hz, 1H), 8.92 (d, J=2.1 Hz, 1H), 8.43 (t, J=2.1 Hz, 1H), 7.76 (s, 1H), 4.24 (s, 3H), 3.98 (s, 3H).

Step 3: 5-((2-methyl-2H-1,2,3-triazol-4-yl)ethynyl)nicotinic acid

To a flask containing methyl 5-((2-methyl-2H-1,2,3-triazol-4-yl)ethynyl)nicotinate (54 g, 223 mmol) in tetrahydrofuran (THF) (540 mL) and water (90 mL) was added NaOH (13.37 g, 334 mmol) and the mixture stirred at room temperature for 3 hours. The mixture was concentrated acidified to pH 2 with 1 M HCl (aq) (~10 mL). The resulting precipitate was filtered and dried overnight in the vacuum oven to provide the title compound (49 g, 91% yield); $^1$H NMR (500 MHz, dimethylsulfoxide-d$_6$) δ 9.14 (s, 1H), 9.06 (s, 1H), 8.37 (s, 1H), 8.15 (s, 1H), 4.70 br (s, 1H), 4.21 (s, 3H).

Preparation #15: 5-((1-(trifluoromethyl)-1H-pyrazol-4-yl)ethynyl)nicotinic acid

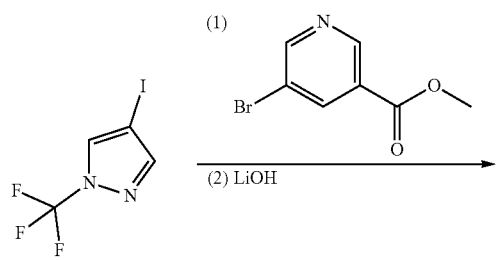

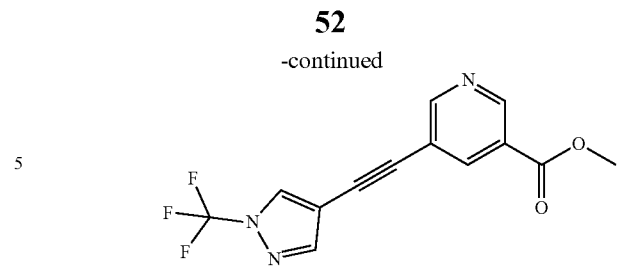

A mixture of triethylamine (TEA) (0.745 mL, 5.34 mmol), copper (I) iodide (0.051 g, 0.267 mmol), tetrakis(triphenylphosphine)palladium(0) (Pd(PPh$_3$)$_4$) (0.309 g, 0.267 mmol), 4-iodo-1-(trifluoromethyl)-1H-pyrazole (1 g, 2.67 mmol) and ethynyltrimethylsilane (1.110 mL, 8.02 mmol) in N,N-dimethylformamide (DMF) (8 mL) was sparged with $N_2$ for 5 minutes and then heated to about 100° C. for about 3 hours. The mixture was cooled to room temperature, concentrated in vacuo and filtered through a plug of silica gel using rinses of 50% ethyl acetate (EtOAc)/Isohexane. The filtrate was concentrated and the residue was taken up in acetonitrile (MeCN) (30 mL), and CsF (0.848 g, 5.58 mmol), methyl 5-bromonicotinate (1.005 g, 4.65 mmol), dicyclohexyl(2',4',6'-triisopropyl-[1,1'-biphenyl]-2-yl)phosphine (0.222 g, 0.465 mmol), bis(acetonitrile)dichloropalladium (II) (Pd(MeCN)$_2$Cl$_2$) (0.060 g, 0.233 mmol) and Cs$_2$CO$_3$ (2.275 g, 6.98 mmol) were added. The mixture was sparged with $N_2$ and stirred under $N_2$ at about 70° C. for about 16 h. The reaction was to cooled to room temperature and the mixture was adsorbed onto Celite (~25 g) under reduced pressure prior to purification by flash column chromatography on silica gel eluting with 10-20% EtOAc/hexanes to obtain methyl 5-((1-(trifluoromethyl)-1H-pyrazol-4-yl)ethynyl)nicotinate (530 mg). This material was dissolved in tetrahydrofuran (THF) (8.0 mL) to which a solution of LiOH (43 mg, 1.8 mmol) in water (2.0 mL) was added and the mixture was stirred at room temperature for about 16 hours. The reaction mixture was concentrated under reduced pressure and the remaining solution was acidified with 1 M hydrochloric acid. The resulting precipitate was collected by filtration and washed with water (5 mL) and hexanes (10 mL), and then dried under vacuum to obtain the title compound (479 mg, 94% yield). $^1$H NMR (500 MHz, dimethylsulfoxide-d$_6$) δ 9.02 (s, 1H), 8.94 (d, J=1.9 Hz, 1H), 8.61 (d, J=2.2 Hz, 1H), 8.28 (t, J=0.9 Hz, 1H), 8.20 (t, J=2.1 Hz, 1H).

Preparation #16: 5-((1-cyclopropyl-1H-pyrazol-4-yl)ethynyl)nicotinic acid

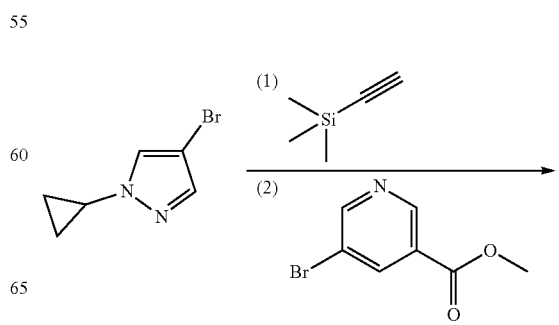

-continued

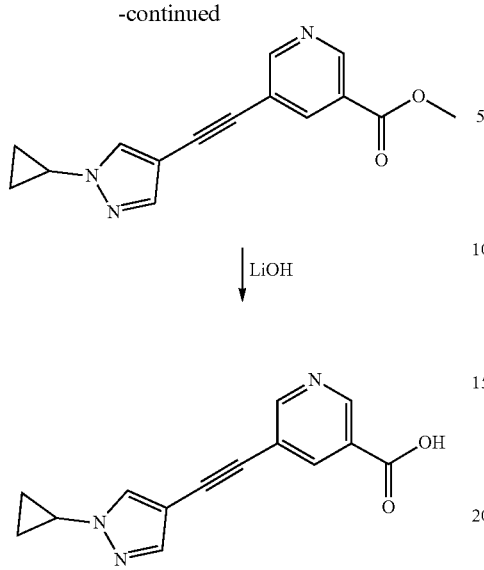

A solution of 4-bromo-1-cyclopropyl-1H-pyrazole (660 mg, 3.53 mmol) and ethynyltrimethylsilane (1.8 mL, 12.99 mmol) in acetonitrile (MeCN) (4 mL) was added to a $N_2$ sparged solution of copper(I) iodide (16 mg, 0.084 mmol), 2-dicyclohexylphosphino-2',4',6'-triisopropylbiphenyl (X-Phos) (205 mg, 0.430 mmol), $PdCl_2(MeCN)_2$ (60 mg, 0.231 mmol) and N,N-Diisopropylethylamine (DIEA) (1.5 mL, 8.59 mmol) in acetonitrile (MeCN) (8 mL) and heated to 70° C. After about 2 hours, a mixture of dicyclohexyl(2',4',6'-triisopropyl-[1,1'-biphenyl]-2-yl)phosphine (XPhos) (205 mg, 0.430 mmol), $PdCl_2(MeCN)_2$ (60 mg, 0.231 mmol) and $Cs_2CO_3$ (1150 mg, 3.53 mmol) in acetonitrile (MeCN) (3 mL) degassed by $N_2$ sparge was added followed by ethynyltrimethylsilane (1.8 mL, 12.99 mmol) and the mixture was heated at about 70° C. for about 16 h. The solution was cooled to room temperature and filtered through silica gel with washes of 1:1 hexanes/Ethyl acetate (EtOAc) (20 mL), and the filtrate was concentrated under reduced pressure. The crude material was dissolved in acetonitrile (MeCN) (12.5 mL) and CsF (536 mg, 3.53 mmol), methyl 5-bromonicotinate (635 mg, 2.94 mmol), X-Phos (140 mg, 0.294 mmol), $PdCl_2(MeCN)_2$ (38.1 mg, 0.147 mmol) and $Cs_2CO_3$ (1437 mg, 4.41 mmol) were added. The reaction mixture was degassed with $N_2$ sparge and then heated at about 70° C. for about 4 hours. The reaction was concentrated under reduced pressure onto Celite (~15 mL) and purified by flash column chromatography on silica gel eluting with 20-70% EtOAc/hexanes to obtain the desired methyl ester (564 mg). LiOH (76 mg, 3.17 mmol) in water (4 mL) was added to a solution of the crude methyl ester (564 mg, 2.110 mmol) in tetrahydrofuran (THF) (12 mL) and allowed to stir at room temperature for 2 hours, then concentrated under reduced pressure to obtain the title compound (545 mg, 70% yield); $^1H$ NMR (500 MHz, dimethylsulfoxide-$d_6$) δ 8.87 (d, J=1.9 Hz, 1H), 8.53 (d, J=2.2 Hz, 1H), 8.22 (s, 1H), 8.12 (t, J=2.0 Hz, 1H), 7.72 (s, 1H), 3.77 (t t, J=7.4, 3.9 Hz, 1H), 1.08 (t, J=3.6 Hz, 2H), 0.98 (dd, J=7.4, 2.5 Hz, 2H). Acid proton not observed.

Preparation #17: 5-bromo-N-((2R,3S)-3-fluoro-2-hydroxy-3-phenylpropyl)-N-methylnicotinamide

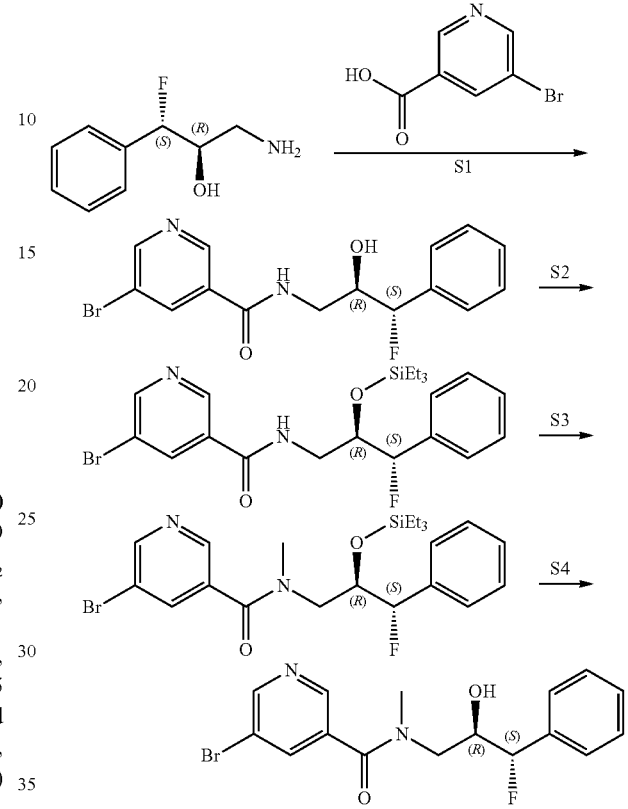

Step 1: 5-bromo-N-((2R,3S)-3-fluoro-2-hydroxy-3-phenylpropyl)nicotinamide

A 50 mL round-bottomed flask equipped with rubber septum and nitrogen inlet needle was charged with 5-bromonicotinic acid (0.322 g, 1.60 mmol), (1S,2R)-3-amino-1-fluoro-1-phenylpropan-2-ol (Preparation #3) (0.270 g, 1.60 mmol) (Preparation #5), 1-(3-dimethylaminopropyl)-3-ethylcarbodiimide hydrochloride (EDC.HCl) (0.459 g, 2.39 mmol), 1-hydroxybenzotriazole (HOBt) hydrate (0.367 g, 2.39 mmol), N,N-diisopropylethylamine (DIEA) (0.836 mL, 4.79 mmol) and N,N-dimethylformamide (DMF) (15 mL). The resulting solution was stirred at room temperature for about 16 hours. The reaction mixture was partitioned between ethyl acetate (50 mL) and sat $NaHCO_3$ (50 mL). After separating the layers, the aq layer was extracted with ethyl acetate (EtOAc) (2×25 mL). The combined organic layers were washed with brine, dried over $Na_2SO_4$, filtered, and concentrated in vacuo. The crude residue was purified by flash chromatography on silica gel eluting with 0-100% EtOAc/heptane to provide the title compound (0.44 g, 78% yield); LC/MS (Table B, Method aa) $R_t$=1.02 min; MS m/z: 353 and 355 (M+H)$^+$.

Step 2: 5-bromo-N-((2R,3S)-3-fluoro-3-phenyl-2-((triethylsilyl)oxy)propyl)-nicotinamide A round-bottomed flask was charged with 5-bromo-N-((2R,3S)-3-fluoro-2-hydroxy-3-phenylpropyl)nicotinamide (0.44 g, 1.25 mmol), 4-dimethylaminopyridine (DMAP) (0.076 g, 0.623 mmol), triethylamine (TEA) (1.04 mL, 7.47 mmol), triethylchlorosilane (SiEt$_3$-Cl) (0.316 mL, 1.87 mmol) and dichloromethane (DCM) (10 mL). The reaction was stirred at 0° C. for about 3 hours. The reaction was partitioned with saturated aq NaHCO$_3$ (10 mL) and water (10 mL) and ethyl acetate (EtOAc) (50 mL). The organic layer was separated and the aq layer was extracted with EtOAc (20 mL). The combined organic layers were washed with brine (20 mL), dried over sodium sulfate, filtered and concentrated in vacuo to provide the title compound (0.63 g, 100% yield); LC/MS (Table B, Method aa) R$_t$=2.04 min; MS m/z: 467 and 469 (M+H)$^+$.

Step 3: 5-bromo-N-((2R,3S)-3-fluoro-3-phenyl-2-((triethylsilyl)oxy)propyl)-N-methylnicotinamide A solution of 5-bromo-N-((2R,3S)-3-fluoro-3-phenyl-2-((triethylsilyl)oxy)-propyl)nicotinamide (0.410 g, 0.807 mmol) and methyl iodide (MeI) (0.101 mL, 1.61 mmol) in N,N-dimethylformamide (DMF) (10 mL) at 0° C. was treated with 60% sodium hydride in mineral oil (0.032 g, 0.807 mmol). The resulting suspension was stirred at 0° C. for about 1 hour. The reaction was quenched with saturated NH$_4$Cl (20 mL), diluted with water and extracted with ethyl acetate (EtOAc) (3×30 mL). The organic layer was dried over sodium sulfate, filtered and concentrated in vacuo. The crude residue was purified by flash chromatography on silica gel eluting with 0-100% EtOAc/heptane to provide the title compound (0.32 g, 82% yield); LC/MS (Table B, Method aa) R$_t$=2.05 min; MS m/z: 481 and 483 (M+H)$^+$.

Step 4: 5-bromo-N-((2R,3S)-3-fluoro-2-hydroxy-3-phenylpropyl)-N-methylnicotin-amide A solution of 5-bromo-N-((2R,3S)-3-fluoro-3-phenyl-2-((triethylsilyl)oxy)-propyl)-N-methyl-nicotinamide (0.32 g, 0.66 mmol) and tetrahydrofuran (THF) (10 mL) at 0° C. was treated with 1 M tetra-N-butylammonium fluoride in THF (0.73 mL, 0.73 mmol). The reaction was stirred at 0° C. for about 2 hours. The reaction was quenched at 0° C. by the addition of sat NH$_4$Cl (20 mL). The mixture was extracted with ethyl acetate (EtOAc) (3×20 mL). The combined organic layers were washed with brine (75 mL), dried over Na$_2$SO$_4$, filtered, and concentrated in vacuo. The crude residue was purified by flash chromatography on silica gel eluting with 0-100% EtOAc/heptane to provide the title compound (0.29 g, 95% yield); LC/MS (Table B, Method aa) R$_t$=1.07 min; MS m/z: 367 and 369 (M+H)$^+$.

Preparation #18: (S)-5-bromo-N-(2-hydroxy-3-phenylpropyl)-6-methoxy-N-methylnicotinamide

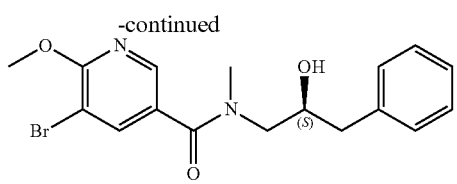

To a stirred solution of 5-bromo-6-methoxynicotinic acid (0.300 g, 1.29 mmol) and (S)-1-(methylamino)-3-phenylpropan-2-ol (Preparation #2) (0.214 g, 1.29 mmol) in dichloromethane (DCM) (13 mL) was added N,N-Diisopropylethylamine (DIEA) (0.677 mL, 3.88 mmol) followed by 1-[Bis(dimethylamino)methylene]-1H-1,2,3-triazolo[4,5-b]pyridinium 3-oxid hexafluorophosphate (HATU) (0.737 g, 1.94 mmol) and the mixture stirred at room temperature for about 18 hours. The mixture was concentrated and purified by flash chromatography on silica gel (0-100% Ethyl acetate (EtOAc)/Isohexane) to provide the title compound (0.66 g, 94% yield); LC/MS (Table B, Method b) R$_t$=1.99 min; MS m/z 379 and 381 (M+H)$^+$.

Preparation #19: (S)-5-bromo-N-(2-hydroxy-3-phenylpropyl)-N,6-dimethylnicotinamide

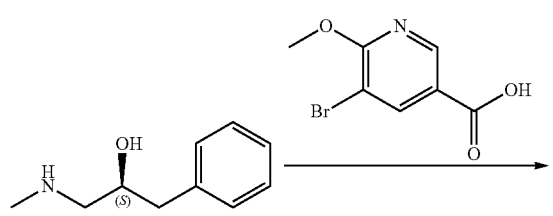

To a solution of 5-bromo-6-methylnicotinic acid (1.0 g, 4.66 mmol), 1-hydroxybenzotriazole (HOBt) hydrate (324 mg, 2.12 mmol) and 1-(3-dimethylaminopropyl)-3-ethylcarbodiimide hydrochloride (EDC.HCl) (1.0 g, 5.51 mmol) in N,N-dimethylformamide (DMF) (10 mL) was added N,N-Diisopropylethylamine (DIEA) (0.740 mL, 4.24 mmol), the solution was stirred for about 5 minutes and then (S)-1-(methylamino)-3-phenylpropan-2-ol (Preparation #2) (700 mg, 4.24 mmol) was added. The reaction was stirred at room temperature for about 20 hours and the solvents were concentrated in vacuo. The residue was partitioned between ethyl acetate (EtOAc) (50 mL) and H$_2$O (50 mL), layers were separated, and the aq phase was extracted into EtOAc (2×50 mL). The combined organics were then washed with saturated aq NaCl (2×50 mL), dried over MgSO$_4$ and concentrated in vacuo. The crude was purified by flash chromatography on silica gel (0-100% Ethyl acetate (EtOAc)/isohexane) to provide the title compound (411 mg, 24% yield); LC/MS (Table B, Method a) R$_t$=1.79 min; MS m/z 364 and 366 (M+H)$^+$.

Preparation #20: (S)-5-bromo-N-(2-hydroxy-3-phenylpropyl)-6-methylnicotinamide

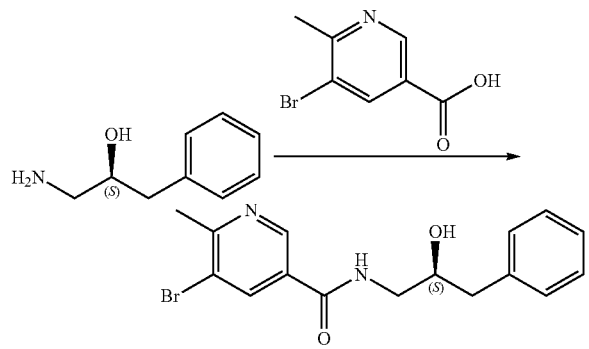

A mixture of 5-bromo-6-methylnicotinic acid (2.7 g, 13.2 mmol), (S)-1-amino-3-phenylpropan-2-ol (2 g, 13 mmol), 1-(3-dimethylaminopropyl)-3-ethylcarbodiimide hydrochloride (EDC.HCl) (3.3 g, 17.2 mmol), and 1-hydroxybenzotriazole (HOBt) hydrate (2.6 g, 17.2 mmol) was dissolved in N,N-dimethylformamide (DMF). N,N-Diisopropylethylamine (DIEA) (5.8 mL, 33.1 mmol) was added in one portion. The resulting solution was allowed to stir at room temperature for about 16 hours. Saturated aqueous NaHCO$_3$ (150 mL) and ethyl acetate (EtOAc) (150 mL) were added, and the phases were separated. The aqueous phase was extracted with EtOAc (3×25 mL). The combined organic phases were washed with brine (2×100 mL), dried over Na$_2$SO$_4$, filtered, and concentrated under reduced pressure. The residue was purified by column chromatography on silica gel eluting with 0-100% EtOAc/heptane to provide the title compound (2.3 g, 49% yield). $^1$H NMR (400 MHz, chloroform-d) δ 2.55 (s, 3H), 2.62-2.70 (m, 1H), 2.72-2.80 (m, 1H), 3.25 (ddd, J=13.63, 8.07, 5.20 Hz, 1H), 3.45 (br s, 1H), 3.62 (ddd, J=13.82, 6.36, 3.18 Hz, 1H), 3.93-4.00 (m, 1H), 7.02-7.12 (m, 3H), 7.16-7.23 (m, 2H), 8.08 (d, J=1.83 Hz, 1H), 8.62 (d, J=1.71 Hz, 1H).

Preparation #21: 5-Ethynyl-2-methyloxazole

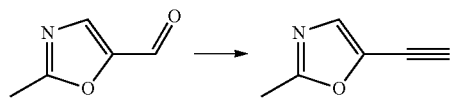

To a stirred solution of 2-methyloxazole-5-carbaldehyde (0.10 g, 0.94 mmol) and K$_2$CO$_3$ (0.26 g, 1.87 mmol) in methanol (MeOH) (3 mL) was added dimethyl(1-diazo-2-oxopropyl)phosphonate (0.21 g, 0.94 mmol) in MeOH (1 mL). The mixture was stirred for about 18 hours at room temperature and then filtered through celite rinsing with MeOH (10 mL). The solution was concentrated carefully in vacuo and the residue was purified by flash chromatography on silica gel (0-50% EtOAc/Isohexane) to give the title compound (0.17 g, 52% yield); $^1$H NMR (500 MHz, chloroform-d) δ 7.17 (s, 1H), 3.56 (s, 1H), 2.47 (s, 3H).

Synthetic Examples

Example #1: (S)-N-(2-hydroxy-3-phenylpropyl)-N-methyl-5-((1-methyl-1H-pyrazol-4-yl)ethynyl)nicotinamide

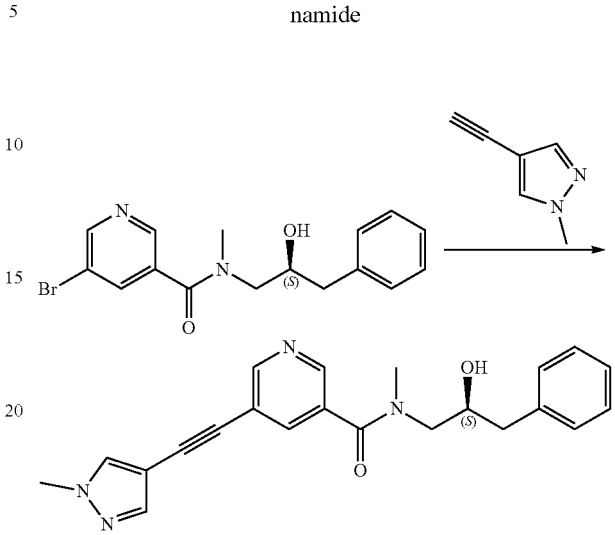

(S)-5-bromo-N-(2-hydroxy-3-phenylpropyl)-N-methylnicotinamide (0.45 g, 1.29 mmol) (Preparation #8), 4-ethynyl-1-methyl-1H-pyrazole (Preparation #10) (0.31 g, 2.92 mmol), 2-dicyclohexylphosphino-2',4',6'-triisopropylbiphenyl (X-Phos) (60 mg, 0.13 mmol), bis(acetonitrile)-dichloropalladium (II) (Pd(MeCN)$_2$Cl$_2$) (20 mg, 0.08 mmol) and Cs$_2$CO$_3$ (0.51 g, 1.57 mmol) were taken up in acetonitrile (MeCN) (21 mL) and the mixture was sparged with N$_2$ for 10 minutes. The resulting mixture was then stirred at about 70° C. for about 3 hours. The mixture was cooled and filtered through Celite rinsing through with ethyl acetate (EtOAc) (60 mL). The solvents were removed in vacuo and the residue purified by flash chromatography on silica gel (0-10% methanol/EtOAc) to provide the title compound (0.25 g, 49% yield). LC/MS (Table B, Method ee) R$_t$=1.77 min; MS m/z 375 (M+H)$^+$; $^1$H NMR (500 MHz, dimethylsulfoxide-d$_6$ at 90° C.) δ 8.65 (d, J=2.0 Hz, 1H), 8.50 (d, J=2.0 Hz, 1H), 8.04 (s, 1H), 7.82 (s, 1H), 7.68 (s, 1H), 7.29-7.12 (m, 5H), 4.75 (br s, 1H), 4.02 (br s, 1H), 3.88 (s, 3H), 3.36-3.26 (m, 2H), 3.00 (s, 3H), 2.70-2.61 (m, 2H).

Example #2: (S)-5-((1-(difluoromethyl)-1H-pyrazol-4-yl)ethynyl)-N-(2-hydroxy-3-phenylpropyl)-N-methylnicotinamide

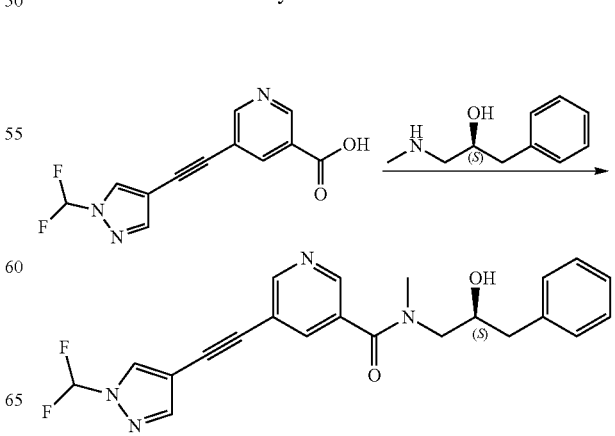

A mixture of 5-((1-(difluoromethyl)-1H-pyrazol-4-yl) ethynyl)nicotinic acid (Preparation #13) (95 g, 361 mmol), N,N-Diisopropylethylamine (DIEA) (189 mL, 1083 mmol) and 1-[Bis(dimethylamino)methylene]-1H-1,2,3-triazolo[4,5-b]pyridinium 3-oxid hexafluorophosphate (HATU) (151 g, 397 mmol) in N,N-dimethylformamide (DMF) (1.00 L) was stirred at room temperature for about 0.5 h. Then (S)-1-(methylamino)-3-phenylpropan-2-ol (Preparation #2) (59.6 g, 361 mmol) was added and the mixture was stirred at room temperature for about 12 hours. The mixture was poured into water (2.00 L) and extracted with ethyl acetate (EtOAc) (3×800 mL). The organic phase was washed with brine (1.50 L), dried over Na$_2$SO$_4$ and concentrated under reduced pressure. The resulting material was purified by flash column chromatography on silica gel eluted with 0-100% EtOAc/petroleum ether to provide the title compound (98 g, 66% yield); LC/MS (Table B, Method aa) R$_t$=1.21 min; MS m/z: 411 (M+H)$^+$; $^1$H NMR (400 MHz, dimethylsulfoxide-d$_6$) δ=8.78-8.66 (m, 2H), 8.62-8.50 (m, 1H), 8.12 (d, J=6.4 Hz, 1H), 8.03-7.69 (m, 2H), 7.30-7.07 (m, 5H), 5.17-4.95 (m, 1H), 4.06 (br d, J=2.9 Hz, 1H), 3.89 (br d, J=5.4 Hz, 1H), 3.58 (br dd, J=3.9, 13.2 Hz, 1H), 3.41-3.35 (m, 1H), 3.20-3.11 (m, 1H), 2.98 (br d, J=14.7 Hz, 3H), 2.81-2.72 (m, 1H), 2.71-2.63 (m, 1H).

Example #3: (S)-N-(2-hydroxy-3-phenylpropyl)-N-methyl-5-((2-methyl-2H-1,2,3-triazol-4-yl)ethynyl) nicotinamide

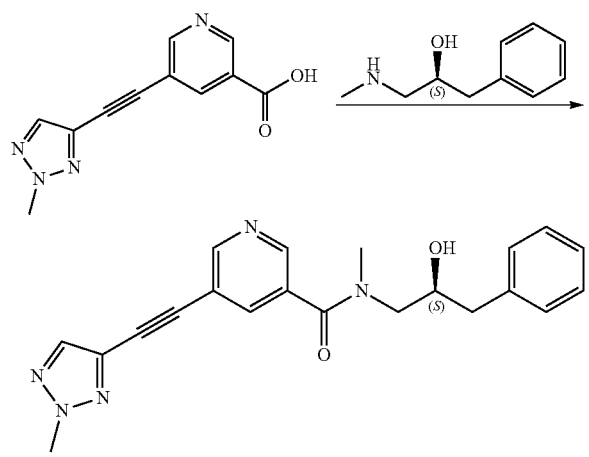

To a flask containing 5-((2-methyl-2H-1,2,3-triazol-4-yl) ethynyl)nicotinic acid (Preparation #14) (23 g, 101 mmol) in tetrahydrofuran (THF) (115 mL) was added N,N'-carbonyldiimidazole (CDI) (24.51 g, 151 mmol) and the mixture stirred at room temperature for about 5 hours. The reaction was added to a solution of (S)-1-(methylamino)-3-phenylpropan-2-ol (Preparation #2) (27.8 g, 151 mmol) and triethylamine (TEA) (28.1 mL, 202 mmol) in tetrahydrofuran (THF) (115 mL). The reaction was stirred at 25° C. for 2 hours. The reaction was completed by LC/MS. The reaction was diluted with water (50 mL) and extracted with ethyl acetate (EtOAc) (300 mL). The organic layer was washed with 15% citric acid (300 mL), brine (500 mL), dried, filtered and concentrated to give a residue which was purified by flash chromatography on silica gel petroleum ether:EtOAc=100:1~0:1 to give the title compound (70 g, 183 mmol, 91% yield yield). (Table B, Method bb) R$_t$=4.24 min; MS m/z: 376 (M+H)$^+$; $^1$H NMR (500 MHz dimethylsulfoxide-d$_6$ at 90° C.) δ 8.75 (s, 1H), 8.58 (s, 1H), 8.03 (s, 1H), 7.94 (s, 1H), 7.33-7.09 (m, 5H), 4.84-4.68 (broad m, 1H), 4.21 (s, 3H), 4.10-3.96 (broad m, 1H), 3.53-3.19 (broad m, 2H), 3.01 (s, 3H), 2.75-2.59 (broad m, 2H).

Example #4: (S)-N-(2-hydroxy-3-phenylpropyl)-N-methyl-5-((1-(trifluoromethyl)-1H-pyrazol-4-yl) ethynyl)nicotinamide

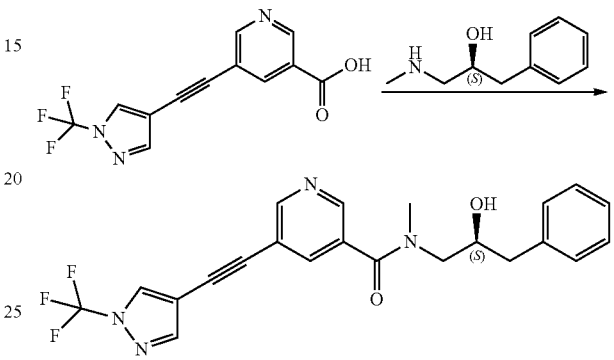

2-(3H-[1,2,3]triazolo[4,5-b]pyridin-3-yl)-1,1,3,3-tetramethylisouronium tetrafluoroborate (TBTU) (859 mg, 2.67 mmol) was added to a solution of (S)-1-(methylamino)-3-phenylpropan-2-ol (Preparation #2) (441 mg, 2.67 mmol), 5-((1-(trifluoromethyl)-1H-pyrazol-4-yl)ethynyl)nicotinic acid (Preparation #15) (500 mg, 1.778 mmol) and N,N-Diisopropylethylamine (DIEA) (0.932 mL, 5.33 mmol) in N,N-dimethylformamide (DMF) (12.4 mL) was stirred at room temperature for about 36 h. Ethyl acetate (EtOAc) (10 mL) was added and the mixture was washed with water (2×10 mL) and brine (10 mL), dried over magnesium sulfate and then concentrated under reduced pressure. The crude product was purified by flash column chromatography on silica gel eluting with 50-100% Ethyl acetate (EtOAc)/hexanes to provide the title compound (655 mg, 78% yield); (Table B, Method aa) R$_t$=1.38 min; MS m/z: 429 (M+H)$^+$; $^1$H NMR (500 MHz, dimethylsulfoxide-d$_6$) δ 9.05 (d, J=9.7 Hz, 1H), 8.87-8.50 (m, 2H), 8.30 (d, J=8.0 Hz, 1H), 8.05-7.81 (m, 2H), 7.39-7.01 (m, 5H), 5.07 (dd, J=76.1, 5.6 Hz, 1H), 4.07 (d, J=8.9 Hz, 0.5H), 3.90 (d, J=8.8 Hz, 0.5H), 3.58 (dd, J=13.3, 4.1 Hz, 0.5H), 3.42-3.33 (m, 0.5H), 3.16 (dd, J=6.3, 3.6 Hz, 1H), 2.99 (d, J=18.2 Hz, 3H), 2.74 (s, 0.5H), 2.72-2.61 (m, 0.5H).

Example #5: (S)-N-(2-hydroxy-3-phenylpropyl)-N-methyl-5-((1-(trifluoromethyl)-1H-pyrazol-4-yl) ethynyl)nicotinamide

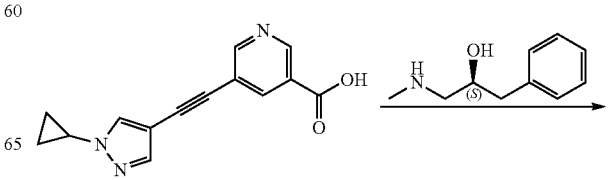

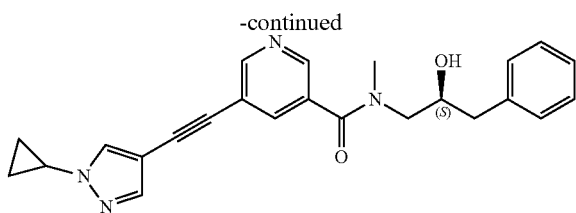

A solution of 1-[Bis(dimethylamino)methylene]-1H-1,2,3-triazolo[4,5-b]pyridinium 3-oxid hexafluorophosphate (HATU) (882 mg, 2.319 mmol), 5-((1-cyclopropyl-1H-pyrazol-4-yl)ethynyl)nicotinic acid (Preparation #16) (534 mg, 2.109 mmol), (S)-1-(methylamino)-3-phenylpropan-2-ol (Preparation #2) (383 mg, 2.319 mmol) and N,N-Diisopropylethylamine (DIEA) (1.105 mL, 6.33 mmol) in dichloromethane (DCM) (20 mL) and tetrahydrofuran (THF) (10 mL) and was stirred at room temperature for about 16 hours. Then, additional N,N-Diisopropylethylamine (DIEA) (1.105 mL, 6.33 mmol), (S)-1-(methylamino)-3-phenylpropan-2-ol (160 mg, 0.968 mmol) and HATU (882 mg, 2.319 mmol) were added and the mixture was stirred at room temperature for 2 hours. The reaction mixture was then diluted with DCM (50 mL) washed with saturated aq ammonium chloride (2×50 mL). The organic portion was dried over magnesium sulfate, filtered and concentrated under reduced pressure. The resulting crude material was purified by flash column chromatography on a silica gel eluting with 0-6% methanol/dichloromethane (DCM) to obtain the title compound (460 mg, 52% yield). (Table B, Method cc) $R_t$=1.89 min; MS m/z: 401 (M+H)$^+$; $^1$H NMR (500 MHz, dimethylsulfoxide-d$_6$) δ 8.67 (dd, J=31.1, 2.0 Hz, 1H), 8.53 (dd, J=33.8, 2.0 Hz, 1H), 8.25 (d, J=8.5 Hz, 1H), 7.88 (dt, J=53.3, 2.1 Hz, 1H), 7.74 (d, J=7.5 Hz, 1H), 7.29 (d, J=4.5 Hz, 2H), 7.23-7.08 (m, 2H), 5.06 (dd, J=70.9, 5.6 Hz, 1H), 4.10-3.84 (m, 1H), 3.78 (dh, J=6.9, 3.3 Hz, 1H), 3.69-3.51 (m, 1H), 3.43-3.33 (m, 1H), 3.21-3.09 (m, 2H), 2.98 (d, J=18.2 Hz, 3H), 2.80-2.62 (m, 1H), 1.13-1.04 (m, 2H), 1.04-0.96 (m, 2H).

Example #6. (S)-5-((1-cyclobutyl-1H-pyrazol-4-yl)ethynyl)-N-(2-hydroxy-3-phenylpropyl)-N-methylnicotinamide

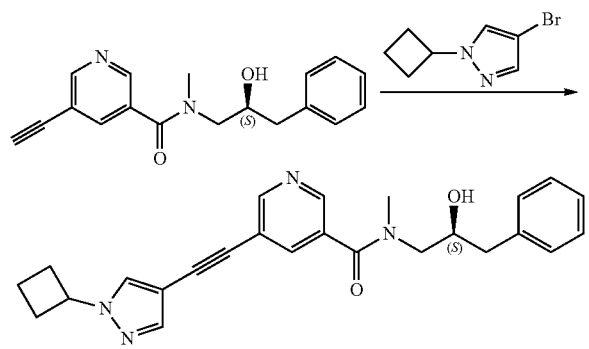

A 7 mL reaction vial equipped with septa cap outfitted with nitrogen inlet needle was charged with (S)-5-ethynyl-N-(2-hydroxy-3-phenylpropyl)-N-methylnicotinamide (Preparation #9) (0.140 g, 0.476 mmol), 4-bromo-1-cyclobutyl-1H-pyrazole (0.096 g, 0.476 mmol), potassium phosphate (0.121 g, 0.571 mmol), and bis(tri-tert-butylphosphine)palladium(0) (0.012 g, 0.024 mmol) in tetrahydrofuran (THF) (2 mL). The reaction mixture was sparged with nitrogen for about 20 minutes and then heated at about 50° C. for about 10 hours. The reaction was cooled to room temperature. The reaction was filtered through a pad of Celite then the filter cake was rinsed with ethyl acetate (EtOAc). The filtrate was concentrated in vacuo. The crude residue was purified by flash chromatography on silica gel eluting with 0-100% EtOAc/heptane followed by 0-5% methanol/EtOAc. The eluent was concentrated in vacuo to provide the title compound (0.056 g, 28% yield); LC/MS (Table B, Method aa) $R_t$=1.33 min; MS m/z: 415 (M+H)$^+$; $^1$H NMR (400 MHz, dimethylsulfoxide-d$_6$) δ 8.67 (d, J=24.6 Hz, 1H), 8.52 (d, J=26.4 Hz, 1H), 8.27 (d, J=6.6 Hz, 1H), 7.96-7.71 (m, 2H), 7.34-7.05 (m, 5H), 5.16-4.92 (m, 1H), 4.11-3.83 (m, 1H), 3.23-3.07 (m, 1H), 2.98 (d, J=14.1 Hz, 3H), 2.79-2.62 (m, 1H), 2.48-2.43 (m, 7H), 1.88-1.71 (m, 2H).

Example #7: N-((2R,3S)-3-fluoro-2-hydroxy-3-phenylpropyl)-N-methyl-5-((1-methyl-1H-pyrazol-4-yl)ethynyl)nicotinamide

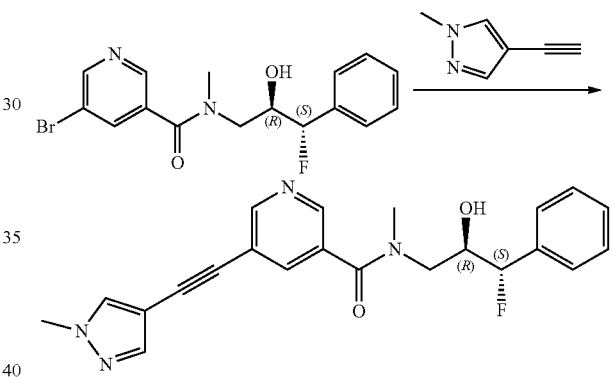

A 20 mL reaction vial equipped with septa cap and outfitted with nitrogen inlet needle was charged with 4-ethynyl-1-methyl-1H-pyrazole (Preparation #10) (0.105 g, 0.987 mmol), 5-bromo-N-((2R,3S)-3-fluoro-2-hydroxy-3-phenylpropyl)-N-methylnicotinamide (Preparation #17) (0.29 g, 0.79 mmol), Chloro(2-dicyclohexylphosphino-2′,4′,6′-triisopropyl-1,1′-biphenyl)[2-(2′-amino-1,1′-biphenyl)]palladium(II) (XPhos Pd G2) (0.031 g, 0.039 mmol) and cesium carbonate (0.322 g, 0.987 mmol). The reaction was flushed with nitrogen. Acetonitrile (MeCN) (3.95 mL) was added and the mixture was sparged with nitrogen. The reaction mixture was heated at about 65° C. for about 3 hours. The reaction was cooled to room temperature. The reaction was filtered through a pad of Celite then the filter cake was rinsed with ethyl acetate (EtOAc). The filtrate was concentrated in vacuo. The crude residue was purified by flash chromatography on silica gel eluting with 0-100% EtOAc/heptane. The material was dried under vacuum to provide the title compound (0.139 g, 45% yield); LC/MS (Table B, Method aa) $R_t$=1.04 min; MS m/z: 393 (M+H)$^+$; $^1$H NMR (400 MHz, dimethylsulfoxide-d$_6$) δ 8.66 (d, J=35.0 Hz, 1H), 8.49 (d, J=30.1 Hz, 1H), 8.13 (d, J=5.5 Hz, 1H), 7.84 (d, J=39.3 Hz, 1H), 7.73 (s, 1H), 7.48-7.23 (m, 5H), 5.67-5.16 (m, 2H), 4.31-4.00 (m, 1H), 3.87 (s, 3H), 3.39-3.19 (m, 2H), 2.98 (d, J=20.7 Hz, 3H).

Example #8: (S)-5-((6,7-Dihydro-4H-pyrazolo[5,1-c][1,4]oxazin-3-yl)ethynyl)-N-(2-hydroxy-3-phenylpropyl)-N-methylnicotinamide

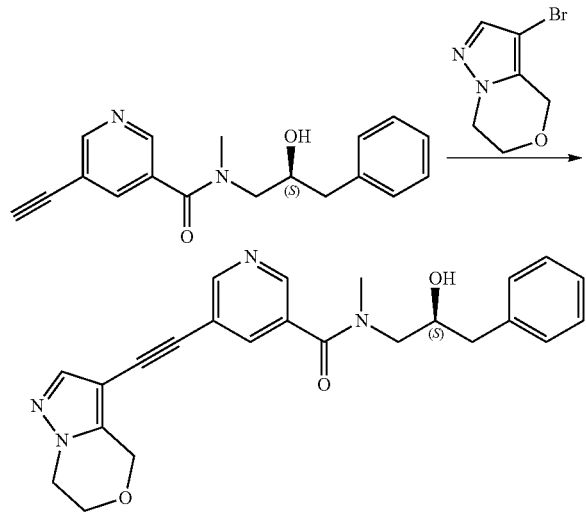

A reaction vial was charged with (S)-5-ethynyl-N-(2-hydroxy-3-phenylpropyl)-N-methylnicotinamide (Preparation #9) (0.192 g, 0.652 mmol), 3-bromo-6,7-dihydro-4H-pyrazolo[5,1-c][1,4]oxazine (Preparation #5) (0.301 g, 0.652 mmol), $K_3PO_4$ (0.166 g, 0.783 mmol), bis(tri-tert-butylphosphine) palladium (0) (Pd(P-tBu$_3$)$_2$) (0.017 g, 0.033 mmol) and tetrahydrofuran (THF) (2.2 mL). The reaction mixture was sparged with $N_2$ for about 20 minutes then heated to about 50° C. for about 20 hours. The reaction mixture was cooled to room temperature and filtered through a pad of Celite. The filter cake was rinsed with ethyl acetate (EtOAc), and the combined filtrate was concentrated in vacuo. The crude isolate was purified via flash chromatography (0%-100% Ethyl acetate (EtOAc) in heptane, then 0 to 5% methanol in EtOAc to furnish the title product (0.12 g, 44% yield). LC/MS (Table B, Method aa) R$_t$=1.04 min; MS m/z: 417 (M+H)$^+$. $^1$H NMR (400 MHz, dimethylsulfoxide-d$_6$) (rotamers present) δ: 8.74-8.61 (m, 1H), 8.60-8.46 (m, 1H), 7.97-7.81 (m, 1H), 7.81-7.73 (m, 1H), 7.33-7.25 (m, 2H), 7.25-7.06 (m, 3H), 5.16-4.88 (m, 3H), 4.18-3.83 (m, 5H), 3.62-3.33 (m, 1H), 3.21-3.10 (m, 1H), 3.03-2.93 (m, 3H), 2.81-2.52 (m, 2H).

Example #9: (S)-6-(difluoromethyl)-N-(2-hydroxy-3-phenylpropyl)-N-methyl-5-((1-methyl-1H-pyrazol-4-yl)ethynyl)nicotinamide

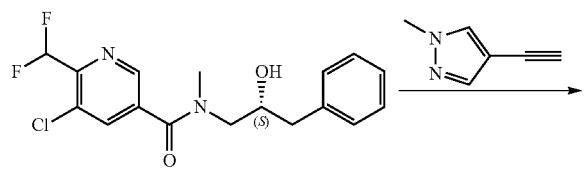

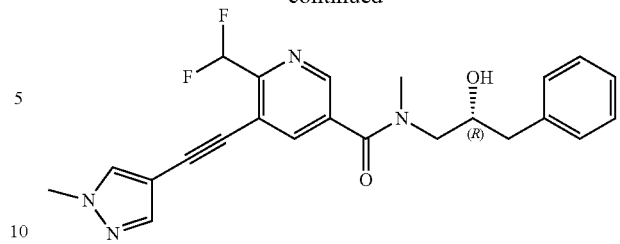

(S)-5-chloro-6-(difluoromethyl)-N-(2-hydroxy-3-phenylpropyl)-N-methylnicotinamide (100 mg, 0.28 mmol) (Preparation #6), 4-ethynyl-1-methyl-1H-pyrazole (Preparation #10) (30 mg, 0.28 mmol), 2-dicyclohexylphosphino-2',4',6'-triisopropylbiphenyl (X-Phos) (27 mg, 0.06 mmol), bis(acetonitrile)dichloropalladium (II) (Pd(MeCN)$_2$Cl$_2$) (7.31 mg, 0.03 mmol) and Cs$_2$CO$_3$ (184 mg, 0.56 mmol) were taken up in acetonitrile (MeCN) (2 mL) and the reaction mixture was sparged with $N_2$ for 10 minutes. The resulting mixture was then stirred at about 70° C. for about 3 hours. The reaction was cooled, and the solvents were removed in vacuo. The residue was subjected to flash column chromatography on silica gel eluting with 0-10% methanol/dichloromethane (DCM) to provide the title compound (54 mg, 43% yield). LC/MS (Table B, Method dd) R$_t$=1.85 min; MS m/z: 425 (M+H)$^+$; $^1$H NMR (500 MHz, 90° C., dimethylsulfoxide-d$_6$) δ 8.59 (s, 1H), 8.09 (s, 1H), 7.98 (s, 1H), 7.72 (s, 1H), 7.36-6.97 (m, 6H), 4.80 (br s, 1H), 4.04 (s, 1H), 3.90 (br s, 3H), 3.30 (br s, 1H), 3.02 (br s, 4H) 2.71 (br s, 2H).

Example #10: (S)-N-(2-hydroxy-3-phenylpropyl)-N-methyl-5-((2-(oxetan-3-yl)-2H-1,2,3-triazol-4-yl)ethynyl)nicotinamide

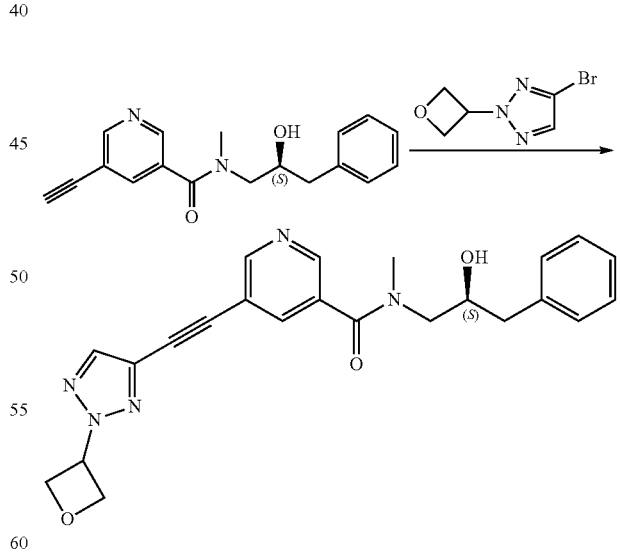

To a vial was added (S)-5-ethynyl-N-(2-hydroxy-3-phenylpropyl)-N-methylnicotinamide (Preparation #9) (0.120 g, 0.41 mmol), 4-bromo-2-(oxetan-3-yl)-2H-1,2,3-triazole (Preparation #7) (0.125 g, 0.61 mmol), Cs$_2$CO$_3$ (0.398 g, 1.22 mmol), bis(acetonitrile)dichloropalladium (II) (Pd (MeCN)$_2$Cl$_2$) (5 mg, 0.02 mmol), and 2-dicyclohexylphosphino-2',4',6'-triisopropylbiphenyl (X-Phos) (19 mg, 0.04 mmol) and the vial was evacuated and back-filled with N₂ (×3). To the vial was added acetonitrile (MeCN) (3.2 mL) and the mixture sparged with N₂ for about 5 minutes, then heated to about 70° C. for about 18 hours. The mixture was cooled to room temperature, filtered through Celite and washed with ethyl acetate (EtOAc) (40 mL). The solution was concentrated in vacuo and purified twice by flash chromatography on silica gel (0-5% methanol/dichloromethane (DCM)). The solid was triturated with methyl tert-butyl ether (MTBE) then dried to provide the title compound (13 mg, 7% yield); LC/MS (Table B, Method ee) $R_t$=1.77 min; MS m/z 418 (M+H)⁺; ¹H NMR (500 MHz, dimethylsulfoxide-$d_6$ at 90° C.) δ 8.78 (s, 1H), 8.61 (s, 1H), 8.20 (s, 1H), 7.98 (s, 1H), 7.30-7.11 (m, 5H), 5.93-5.86 (m, 1H), 5.08-5.03 (m, 2H), 5.00-4.96 (m, 2H), 4.83-4.71 (m, 1H), 4.11-3.97 (m, 1H), 3.45-3.24 (m, 2H), 3.02 (s, 3H), 2.76-2.60 (m, 2H).

Example #11: (S)-5-((5-cyclopropyl-1-methyl-1H-pyrazol-4-yl)ethynyl)-N-(2-hydroxy-3-phenylpropyl)-N-methylnicotinamide

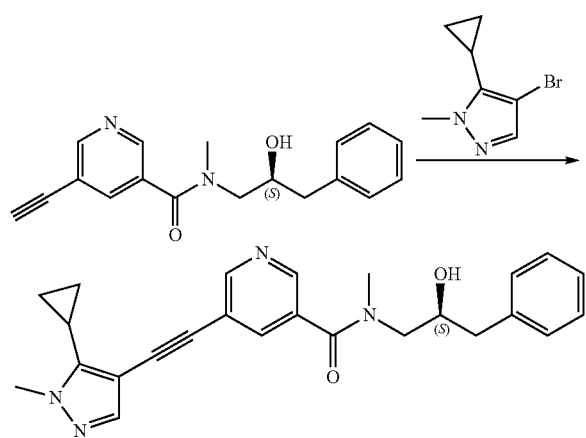

To a vial was added (S)-5-ethynyl-N-(2-hydroxy-3-phenylpropyl)-N-methylnicotin-amide (Preparation #9) (60 mg, 0.20 mmol), 4-bromo-5-cyclopropyl-1-methyl-1H-pyrazole (82 mg, 0.41 mmol), Cs₂CO₃ (199 mg, 0.61 mmol), bis(acetonitrile)dichloropalladium (II) (Pd(MeCN)₂Cl₂) (5 mg, 0.019 mmol), and 2-dicyclohexylphosphino-2',4',6'-triisopropylbiphenyl (X-Phos) (19 mg, 0.04 mmol) and the vial was evacuated and back-filled with N₂ (×3). To the vial was added acetonitrile (MeCN) (2 mL) and the mixture sparged with N₂ for about 5 min, then heated to about 70° C. for about 4 h. The mixture was filtered through Celite rinsing with Ethyl acetate (EtOAc) (10 mL). The solution was concentrated in vacuo and purified via flash chromatography on silica gel (0-100% Ethyl acetate (EtOAc)/isohexane) to provide the title compound (16 mg, 18% yield); LC/MS (Table B, Method b) $R_t$=1.21 min; MS m/z 415 (M+H)⁺; ¹H NMR (500 MHz, dimethylsulfoxide-$d_6$ at 90° C.) δ 8.63 (d, J=2.0 Hz, 1H), 8.50 (d, J=2.0 Hz, 1H), 7.80 (d, J=2.1 Hz, 1H), 7.53 (s, 1H), 7.27-7.13 (m, 5H), 4.76 (br s, 1H), 4.08-4.02 (m, 1H), 3.86 (s, 3H), 3.44-3.35 (m, 2H), 3.01 (s, 3H), 2.67-2.62 (m, 2H), 1.97 (ddd, J=13.8, 8.1, 5.7 Hz, 1H), 1.13-1.04 (m, 4H).

Example #12: (S)-N-(3-(3-fluorophenyl)-2-hydroxypropyl)-N-methyl-5-((1-methyl-1H-pyrazol-4-yl)ethynyl)nicotinamide

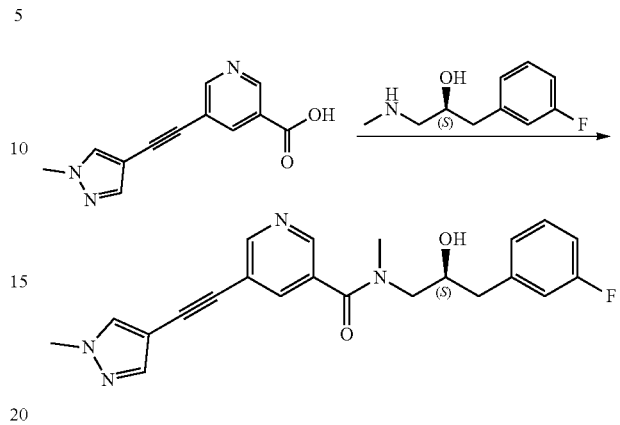

2-(3H-[1,2,3]triazolo[4,5-b]pyridin-3-yl)-1,1,3,3-tetramethylisouroniumtetrafluoro-borate (TBTU) (127 mg, 0.393 mmol) was added to a solution of (S)-1-(3-fluorophenyl)-3-(methylamino)propan-2-ol (Preparation #4) (60 mg, 0.327 mmol), 5-((1-methyl-1H-pyrazol-4-yl)ethynyl)nicotinic acid (Preparation #12) (74.4 mg, 0.327 mmol) and N,N-Diisopropylethylamine (DIEA) (0.172 mL, 0.982 mmol) in N,N-dimethylformamide (DMF) (2 mL) at room temperature and stirred for about 18 hours. The mixture was diluted with ethyl acetate (EtOAc) (10 mL) and saturated aq. NH₄Cl (10 mL) and the layers were separated. The organic layer was washed with saturated aq. NaCl (3×10 mL), dried over MgSO₄ and concentrated in vacuo. The crude material was purified by flash chromatography on silica gel (0-10% methanol/dichloromethane (DCM)) followed by reverse phase chromatography (15-75% acetonitrile (MeCN) in H₂O(+0.1% ammonium bicarbonate)) to provide the title compound (72 mg, 53% yield); LC/MS (Table B, Method ee) $R_t$=1.74 min; MS m/z 393 (M+H)⁺. ¹H NMR (500 MHz, dimethylsulfoxide-$d_6$ at 90° C.) δ 8.66 (d, J=2.0 Hz, 1H), 8.52 (d, J=2.0 Hz, 1H), 8.04 (s, 1H), 7.84 (s, 1H), 7.68 (s, 1H), 7.28 (q, J=7.5 Hz, 1H), 7.04 (s, 2H), 6.99-6.94 (m, 1H), 4.82 (br s, 1H), 4.04 (br s, 1H), 3.89 (s, 3H), 3.44-3.27 (m, 2H), 3.01 (s, 3H), 2.76-2.61 (m, 2H).

Example #13: (S)-N-(2-hydroxy-3-phenylpropyl)-6-methoxy-N-methyl-5-((1-methyl-1H-pyrazol-4-yl)ethynyl)nicotinamide

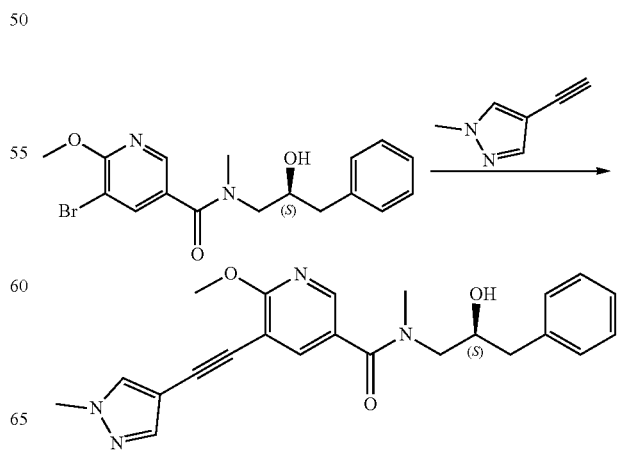

To a flask was added (S)-5-bromo-N-(2-hydroxy-3-phenylpropyl)-6-methoxy-N-methylnicotinamide (Preparation #18) (0.220 g, 0.464 mmol), $Cs_2CO_3$ (0.189 g, 0.580 mmol), bis(acetonitrile)dichloropalladium (II) ($Pd(MeCN)_2Cl_2$) (6 mg, 0.023 mmol), XPhos (0.022 g, 0.046 mmol) and acetonitrile (MeCN) (4 mL). The reaction was sparged with $N_2$ for 10 minutes and 4-ethynyl-1-methyl-1H-pyrazole (Preparation #10) (0.075 g, 0.707 mmol) in acetonitrile (MeCN) (1 mL) was added. The reaction was then heated to about 75° C. for about 30 minutes. The mixture was concentrated in vacuo and purified by flash chromatography on silica gel (0-100% Ethyl acetate (EtOAc)/isohexane) to give a colorless oil. The oil was taken into methanol (1 mL) and acetic acid (AcOH) (0.2 mL) and loaded onto a pad of Strong Cation Exchange (SCX). The pad was washed with methanol (20 mL) followed by 0.7 M $NH_3$ in methanol (20 mL). The basic solution was concentrated and purified by flash chromatography on silica gel (0-10% methanol/dichloromethane (DCM)) to provide the title compound (25 mg, 13% yield); LC/MS (Table B, Method b) $R_t$=1.86 min; MS m/z 405 $(M+H)^+$; $^1H$ NMR (500 MHz, dimethylsulfoxide-$d_6$ at 90° C.) δ 8.16 (d, J=2.3 Hz, 1H), 8.00 (s, 1H), 7.78 (d, J=2.3 Hz, 1H), 7.64 (s, 1H), 7.28-7.12 (m, 5H), 4.71 (d, J=5.6 Hz, 1H), 3.99 (s, 3H), 3.87 (s, 3H), 3.39 (s, 1H), 3.32 (dd, J=13.8, 8.4 Hz, 1H), 3.01 (s, 3H), 2.70-2.60 (m, 2H).

Example #14: (S)-N-(2-hydroxy-3-phenylpropyl)-N, 6-dimethyl-5-((1-methyl-1H-pyrazol-4-yl)ethynyl)nicotinamide

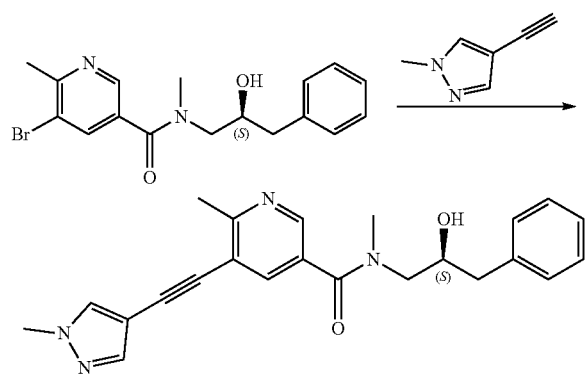

(S)-5-bromo-N-(2-hydroxy-3-phenylpropyl)-N,6-dimethylnicotinamide (Preparation #19) (130 mg, 0.358 mmol), 4-ethynyl-1-methyl-1H-pyrazole (Preparation #10) (76 mg, 0.716 mmol), 2-dicyclohexylphosphino-2',4',6'-triisopropylbiphenyl (X-Phos) (17 mg, 0.036 mmol), bis(acetonitrile)dichloropalladium (II) ($Pd(MeCN)_2Cl_2$) (5 mg, 0.018 mmol) and $Cs_2CO_3$ (140 mg, 0.429 mmol) were taken up in acetonitrile (MeCN) (6 mL) and the mixture was sparged with $N_2$ for about 10 minutes. The mixture was then stirred at about 70° C. for about 3 hours. The reaction was cooled and filtered through a pad of Celite rinsing with ethyl acetate (EtOAc) (20 mL). The solvents were removed in vacuo and the residue was pre-adsorbed onto Celite and purified by flash chromatography on silica gel (0-10% methanol/dichloromethane (DCM)) to provide the title compound (106 mg, 75% yield); LC/MS (Table B, Method a) $R_t$=1.73 min; MS m/z 389 $(M+H)^+$. $^1H$ NMR (500 MHz, dimethylsulfoxide-$d_6$ at 90° C.) δ 8.38 (d, J=2.1 Hz, 1H), 8.04 (s, 1H), 7.74 (d, J=2.1 Hz, 1H), 7.67 (s, 1H), 7.27-7.13 (m, 5H), 4.81-4.61 (m, 1H), 4.08-3.97 (m, 1H), 3.88 (s, 3H), 3.49-3.23 (m, 2H), 3.00 (s, 3H), 2.71-2.66 (m, 2H), 2.64 (s, 3H).

Example #15: (S)-N-(2-hydroxy-3-phenylpropyl)-N-methyl-5-((2-methylthiazol-5-yl)ethynyl) nicotinamide

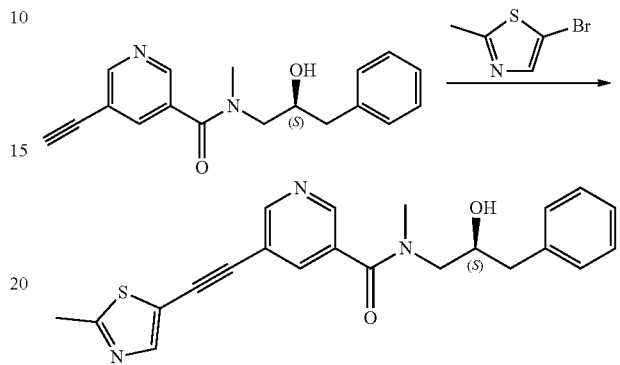

To a vial was added 5-bromo-2-methylthiazole (181 mg, 1.02 mmol), (S)-5-ethynyl-N-(2-hydroxy-3-phenylpropyl)-N-methylnicotinamide (Preparation #9) (150 mg, 0.51 mmol) $Cs_2CO_3$ (498 mg, 1.53 mmol), bis(acetonitrile)dichloropalladium (II) ($Pd(MeCN)_2Cl_2$) (9.3 mg, 0.04 mmol) and 2-dicyclohexylphosphino-2',4',6'-triisopropylbiphenyl (X-Phos) (24.3 mg, 0.05 mmol) and the vial was evacuated and back-filled with $N_2$ (×3). To the vial was added acetonitrile (5 mL) and the mixture sparged with $N_2$ for about 5 minutes, then heated to about 85° C. for about 3 hours. The mixture was filtered through Celite rinsing with ethyl acetate (EtOAc) (40 mL). The solution was concentrated in vacuo and purified by flash chromatography on silica gel (0-5% methanol/dichloromethane (DCM)) to provide a residue which was triturated with methyl tert-butyl ether (MTBE) and dried to provide the title compound (50 mg, 24% yield); LC/MS (Table B, Method ee) $R_t$=1.89 min; MS m/z 392 $(M+H)^+$; $^1H$ NMR (500 MHz, dimethylsulfoxide-$d_6$ at 90° C.) δ 8.73 (s, 1H), 8.57 (s, 1H), 7.96 (s, 1H), 7.92 (s, 1H), 7.30-7.10 (m, 5H), 4.82-4.70 (broad m, 1H), 4.10-3.95 (broad m, 1H), 3.51-3.21 (broad m, 2H), 3.01 (s, 3H), 2.71 (s, 3H), 2.73-2.58 (broad m, 2H).

Example #16: (S)-N-(2-hydroxy-3-phenylpropyl)-6-methyl-5-(thiazol-5-ylethynyl)nicotinamide

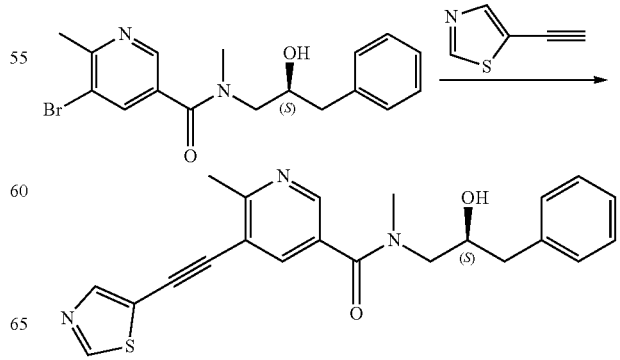

To a vial was charged 5-ethynylthiazole (30.6 mg, 0.28 mmol), (S)-5-bromo-N-(2-hydroxy-3-phenylpropyl)-6-methylnicotinamide (Preparation #20) (70 mg, 0.20 mmol) and CuI (7.6 mg, 0.04 mmol) and the vial was evacuated and back-filled with $N_2$ (×3). N,N-Dimethylformamide (DMF) (3 mL) and $Et_3N$ (498 mg, 1.53 mmol) were added and the reaction mixture was sparged with $N_2$ for about 15 minutes. Bis(triphenylphosphine)palladium (II) dichloride ($Pd(PPh_3)_2Cl_2$) (16.9 mg, 0.02 mmol) was added and the reaction mixture was heated to about 90° C. for about 18 hours. The mixture was filtered through Celite rinsing with ethyl acetate (EtOAc) (10 mL). The solution was concentrated in vacuo and the residue was purified by flash chromatography on silica gel (0-10% methanol/dichloromethane (DCM)) to provide the title compound (17 mg, 21% yield); LC/MS (Table B, Method ee) $R_t$=2.03 min; MS m/z 378 (M+H)$^+$; $^1$H NMR (500 MHz, dimethylsulfoxide-$d_6$) δ 9.23 (s, 1H), 8.88 (d, J=2.3 Hz, 1H), 8.64 (t, J=5.7 Hz, 1H), 8.33 (d, J=2.3 Hz, 1H), 8.31 (s, 1H), 7.31-7.21 (m, 4H), 7.21-7.14 (m, 1H), 4.92 (d, J=5.4 Hz, 1H), 3.92-3.84 (m, 1H), 3.38-3.29 (m, 1H), 3.25-3.18 (m, 1H), 2.76 (dd, J=13.6, 5.0 Hz, 1H), 2.69 (s, 3H), 2.65 (dd, J=13.7, 7.6 Hz, 1H).

Example #17: (S)-N-(2-hydroxy-3-phenylpropyl)-N-methyl-5-((2-methyloxazol-5-yl)ethynyl)nicotinamide

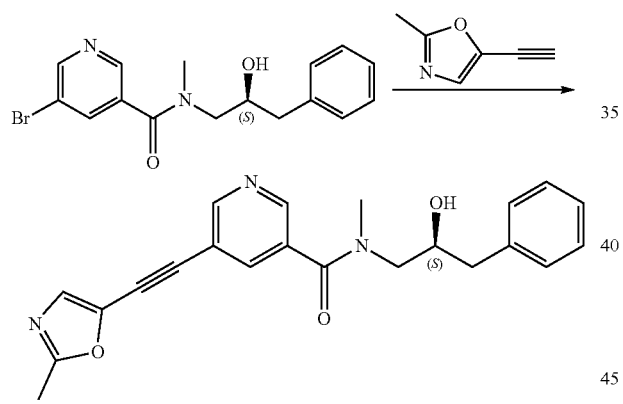

(S)-5-bromo-N-(2-hydroxy-3-phenylpropyl)-6-methylnicotinamide (Preparation #20) (318 mg, 0.91 mmol) $Cs_2CO_3$ (365 mg, 1.1 mmol), bis(acetonitrile)dichloropalladium (II) ($Pd(MeCN)_2Cl_2$) (12 mg, 0.05 mmol) and 2-dicyclohexylphosphino-2',4',6'-triisopropylbiphenyl (X-Phos) (43 mg, 0.09 mmol) were taken up in MeCN (9 mL) and a solution of 5-ethynyl-2-methyloxazole (Preparation #21) (0.19 g, 0.91 mmol) in MeCN (1 mL) was added. The reaction mixture was sparged with $N_2$ for about 5 min and then heated to about 60° C. for about 3 hours. The mixture was filtered through Celite, solvents were concentrated in vacuo and the resulting residue was purified by flash chromatography on silica gel (0-10% MeOH/DCM) to provide the title compound (25 mg, 7%); LC/MS (Table B, Method ee) $R_t$=1.92 min; MS m/z 376 (M+H)$^+$; $^1$H NMR (500 MHz, dimethylsulfoxide-$d_6$ at 90° C.) δ 8.79-8.72 (m, 1H), 8.59 (d, J=2.1 Hz, 1H), 7.94 (s, 1H), 7.49 (s, 1H), 7.21 (dt, J=31.1, 7.3 Hz, 5H), 4.76 (br s, 1H), 4.02 (br s, 1H), 3.30 (br s, 2H), 3.01 (s, 3H), 2.64 (d, J=9.1 Hz, 2H), 2.48 (s, 3H).

Examples #18 and 19: (S)-di-tert-butyl (1-(5-((1-(difluoromethyl)-1H-pyrazol-4-yl)ethynyl)-N-methylnicotinamido)-3-phenylpropan-2-yl) phosphate (Example #18) and (S)-1-(5-((1-(difluoromethyl)-1H-pyrazol-4-yl)ethynyl)-N-methylnicotinamido)-3-phenylpropan-2-yl dihydrogen phosphate (Example #19)

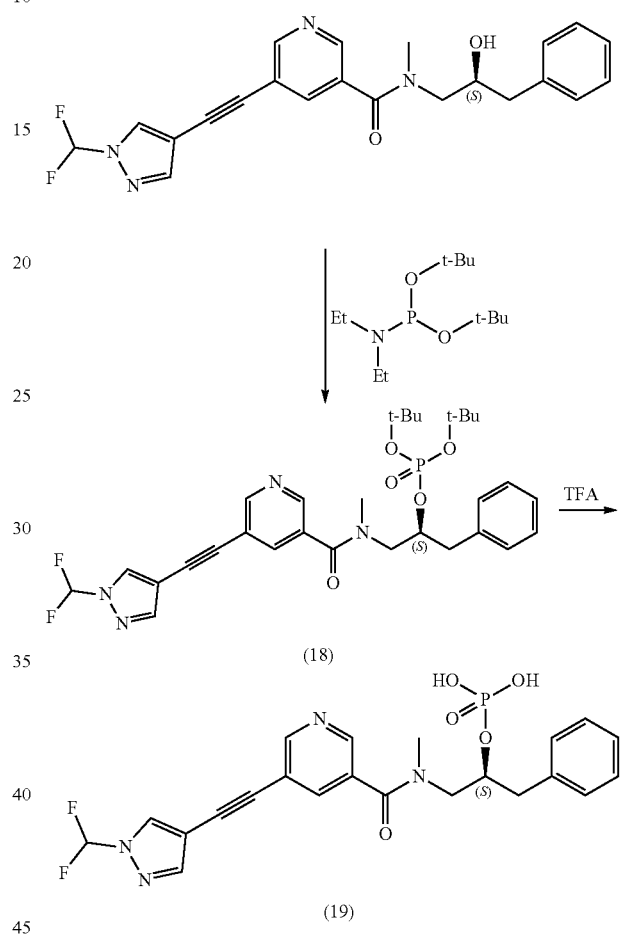

To a solution of (S)-5-((1-(difluoromethyl)-1H-pyrazol-4-yl)ethynyl)-N-(2-hydroxy-3-phenylpropyl)-N-methylnicotinamide (Example #2) (500 mg, 1.22 mmol) in N-Methyl-2-pyrrolidinone (1000 mL) was added di-tert-butyl diethylphosphoramidite (304 mg, 1.22 mmol) and 1H-tetrazole (10.8 mL, 4.87 mmol) in one portion at 20° C. under $N_2$. The mixture was stirred at 40° C. for 3 hours. Hydrogen peroxide (5.0 mL, 49 mmol) was added to the solution at 0° C., and the mixture was stirred for an additional 2 hours. The mixture was poured into saturated $Na_2SO_3$ (75 mL) and extracted with ethyl acetate (EtOAc) (3×100 mL). The organic phase was washed with brine (100 mL), dried over $Na_2SO_4$, concentrated under reduced pressure to give the crude t-butyl phosphate ester, which was chromatographed on silica gel (petroleum ether: ethyl acetate=1:1-1:4) to provide (S)-di-tert-butyl (1-(5-((1-(difluoromethyl)-1H-pyrazol-4-yl)ethynyl)-N-methylnicotinamido)-3-phenylpropan-2-yl) phosphate (Example #18) (384 mg, 0.64 mmol, 52% yield). LC/MS (Table B, Method aa) $R_t$=1.73 min; MS m/z: 545.20 (M-tBu)$^+$; $^1$H NMR (400 MHz, DMSO-$d_6$) δ 8.76-8.40 (m, 3H), 8.15-7.60 (m, 3H), 7.27-7.01 (m, 5H), 4.78-4.46 (br m, 1H), 3.75-2.72 (m, 7H), 1.50-1.18 (m, 18H). tBu=tert-butyl; Et=ethyl.

A flask was charged with (S)-di-tert-butyl (1-(5-((1-(difluoromethyl)-1H-pyrazol-4-yl)ethynyl)-N-methylnicotinamido)-3-phenylpropan-2-yl) phosphate (Example #18) (381 mg, 0.632 mmol), dichloromethane (DCM) (5 mL) and trifluoroacetic acid (TFA) (0.61 mL, 7.9 mmol) and stirred at room temperature for approximately 19 hours. The mixture was concentrated under reduced pressure, then purified via reverse phase liquid chromatography (Atlantis® Prep T3 Phenomenex 5 m 19×50 mm column, 5 to 95 acetonitrile (MeCN):water (formic acid buffer) at 1 mL/minute) to provide the title compound, Example #19 (230 mg, 0.47 mmol, 74% yield). LC/MS (Table B, Method ff) $R_t$=1.96 min; MS m/z: 491.0 (M+H)$^+$; $^1$H NMR (400 MHz, DMSO-d$_6$) δ 8.78-8.69 (m, 1H), 8.65-8.57 (m, 1H), 8.44 (d, J=1.0 Hz, 1H), 8.14-8.08 (m, 1H), 8.03-7.99 (m, 1H), 7.97 (s, 1H), 7.88-7.84 (m, 1H), 7.76 (s, 1H), 7.73-7.69 (m, 1H), 7.35-7.28 (m, 2H), 7.27-7.21 (m, 1H), 7.19-7.12 (m, 1H), 7.03 (br d, J=7.5 Hz, 1H), 4.80-4.73 (m, 1H), 4.52-4.45 (m, 1H), 3.84-3.76 (m, 1H), 3.66 (br d, J=13.5 Hz, 1H), 3.33 (br dd, J=9.5, 13.5 Hz, 1H), 3.27-3.11 (m, 1H), 3.08-3.00 (m, 1H), 2.97 (s, 1H), 2.95 (br s, 1H), 2.92 (s, 2H), 2.90-2.85 (m, 1H), 2.79-2.69 (m, 1H), 2.07 (s, 1H), 1.78 (s, 1H), 1.74 (s, 1H).

Example #20: (S)-1-(5-((1-(difluoromethyl)-1H-pyrazol-4-yl)ethynyl)-N-methylnicotinamido)-3-phenylpropan-2-yl acetate

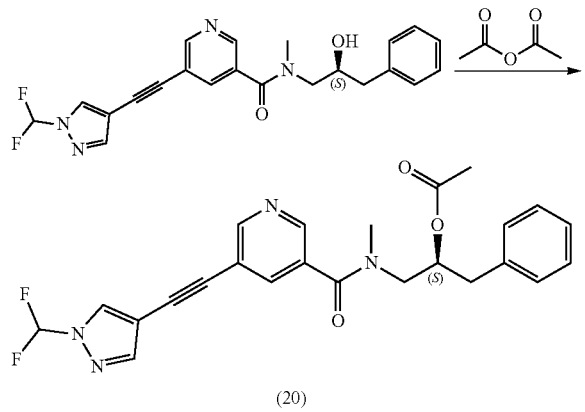

(20)

To a solution of (S)-5-((1-(difluoromethyl)-1H-pyrazol-4-yl)ethynyl)-N-(2-hydroxy-3-phenylpropyl)-N-methylnicotinamide (Example #2) (2.00 g, 4.87 mmol) in 20 mL of dicholoromethane was added triethylamine (2.38 mL, 17.1 mmol), acetic anhydride (1.0 mL, 11 mmol) and 4-dimethylaminopyridine (0.095 g, 0.78 mmol). The mixture was stirred at 20° C. for 2 hours. After this time, the mixture was poured into saturated ammonium chloride. The organic phase was extracted with brine (50 mL), dried over sodium sulfate, and concentrated. The resultant residue was purified by preparative HPLC (Table B, Method c) to provide the title compound (1.0 g, 2.1 mmol, 44% yield). $^1$H NMR (400 MHz, chloroform-d) δ=8.74 (br s, 1H), 8.54 (s, 1H), 8.06 (s, 1H), 7.82 (s, 1H), 7.75 (br s, 1H), 7.38-7.28 (m, 2H), 7.24-7.03 (m, 3H), 5.58-5.21 (m, 1H), 4.02-3.89 (m, 1H), 3.64-3.55 (m, 1H), 3.54-3.45 (m, 1H), 3.40-3.26 (m, 1H), 3.13-2.93 (m, 5H), 2.89-2.78 (m, 1H), 2.69-2.53 (m, 1H), 2.14-1.99 (m, 3H).

Example #21: (S)-1-(5-((1-(difluoromethyl)-1H-pyrazol-4-yl)ethynyl)-N-methylnicotinamido)-3-phenylpropan-2-yl 2-aminoacetate, hydrochloric acid

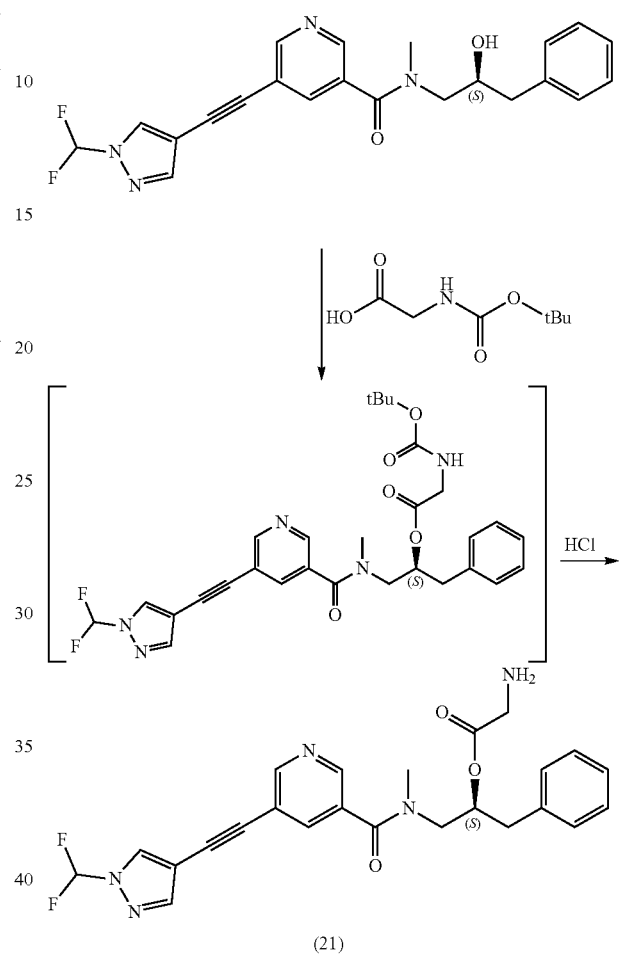

(21)

To a solution of 2-((tert-butoxycarbonyl)amino)acetic acid (0.854 g, 4.87 mmol) in 5.0 mL of acetonitrile was added (S)-5-((1-(difluoromethyl)-1H-pyrazol-3-yl)ethynyl)-N-(2-hydroxy-3-phenylpropyl)-N-methylnicotinamide (Example #2) (2.0 g, 4.9 mmol), N,N'-dicyclohexylcarbodiimide (DCC) (1.05 g, 5.08 mmol) and 4-dimethylaminopyridine (DMAP) (0.015 g, 0.12 mmol). The mixture was stirred at 20° C. for 12 hours. After this time, the reaction mixture was filtered and the filtrate was concentrated in vacuo to give a crude intermediate, (S)-1-(5-((1-(difluoromethyl)-1H-pyrazol-4-yl)ethynyl)-N-methylnicotinamido)-3-phenylpropan-2-yl (tert-butoxycarbonyl)glycinate (2.4 g, 4.2 mmol), which was then dissolved in ethyl acetate (15 mL). Hydrogen chloride solution in ethyl acetate (4M, 20 mL) was added, and the reaction mixture was stirred at 20° C. for 30 minutes. After this time, the mixture was concentrated under pressure to give a residue, which was purified by preparative HPLC (Table B, Method c; $R_t$=2.13 min) to provide the title compound (1.2 g, 2.3 mmol, 54% yield). $^1$H NMR (400 MHz, dimethylsulfoxide-d$_6$) δ=8.88-8.70 (m, 2H), 8.61 (d, J=1.5 Hz, 1H), 8.57-8.42 (m, 3H), 8.19-8.09 (m, 1H), 8.09-7.74 (m, 2H), 7.37-7.29 (m, 3H), 7.28-7.15 (m, 2H), 7.08 (br d, J=6.5 Hz, 1H), 5.54-5.17 (m, 1H), 3.86-3.62 (m, 2H), 3.70-3.62 (m, 1H), 3.52-3.38 (m, 1H), 3.09-3.00 (m, 1H), 2.99 (s, 1H), 2.96 (s, 2H), 2.95-2.89 (m, 1H), 2.82-2.66 (m, 1H). tBu=tert-butyl.

Examples #22 and #23: (S)-di-tert-butyl (1-(N-methyl-5-((2-methyl-5-2H-1,2,3-triazol-4-yl)ethynyl)nicotinamido)-3-phenylpropan-2-yl) phosphate (Example #22) and (S) (1-(N-methyl-5-((2-methyl-2H-1,2,3-triazol-4-yl)ethynyl)nicotinamido)-3-phenylpropan-2-yl) dihydrogen phosphate (Example #23)

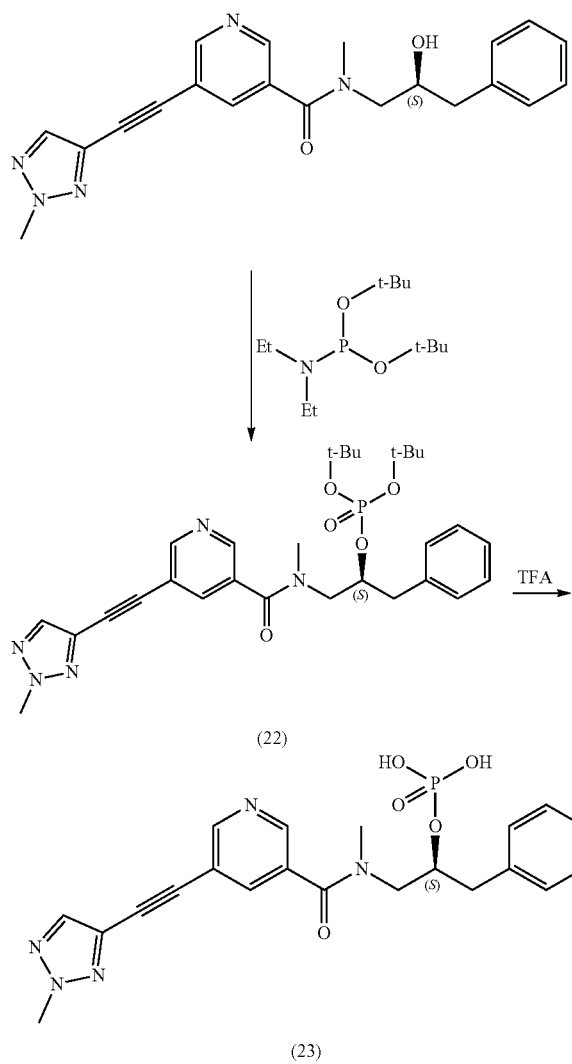

To a solution of (S)-N-(2-hydroxy-3-phenylpropyl)-N-methyl-5-((2-methyl-2H-1,2,3-triazol-4-yl)ethynyl)nicotinamide (Example #3) (2.00 g, 5.33 mmol) in 40 mL of N-methylpyrrolidine was added di-tert-butyl diethylphosphoramidite (20.0 mL, 5.33 mmol) and 1H-tetrazole (1.493 g, 21.31 mmol) in one portion at 20° C. under nitrogen, and stirred for 2 hours. After this time, hydrogen peroxide (20.0 mL, 555 mmol) was added to the solution at 0° C. The mixture was stirred at 20° C. for 1 hour, and an aliquot was removed and analyzed by LC-MS. LC-MS showed that the starting material was completely consumed and the desired product (phosphate ester) was detected. The resulting mixture was quenched by addition of 20 mL of sodium sulfite at 10° C., and then stirred for 30 minutes. The mixture was poured into ice water, then saturated sodium sulfite solution was added until pH=7. Ethyl acetate (200 mL) was added to the mixture, the mixture was agitated, and the layers were separated. This process was repeated three times. The organic layer was concentrated and the crude (S)-di-tert-butyl (1-(N-methyl-5-((2-methyl-2H-1,2,3-triazol-4-yl) ethynyl)nicotinamido)-3-phenylpropan-2-yl) phosphate (Example #22) was used in the next step without further purification. tBu=tert-butyl; Et=ethyl.

To a solution of (S)-di-tert-butyl (1-(N-methyl-5-((2-methyl-2H-1,2,3-triazol-4-yl)ethynyl)nicotinamido)-3-phenylpropan-2-yl) phosphate (Example #22) (2 g, 3.52 mmol) in 15 mL of dichlormethane was added trifluoroacetic acid (TFA) (5 mL, 64.9 mmol) at 20° C. under nitrogen. The mixture was stirred for 2 hours. After this time, the reaction was concentrated and purified by reverse phase column chromatography (Table B, Method d) to provide the title compound (Example #23) (930 mg, 2.00 mmol, 56.8% yield). $^1$H NMR (400 MHz, dimethylsulfoxide-d$_6$) δ 8.45-8.83 (m, 2H), 7.80-8.17 (m, 2H), 7.21-7.35 (m, 3H), 7.00-7.19 (m, 2H), 4.43-4.82 (m, 1H), 4.17-4.29 (m, 3H), 3.31-3.70 (m, 1H), 2.72-3.26 (m, 6H).

Example #24: (S)-1-(N-methyl-5-((2-methyl-2H-1,2,3-triazol-4-yl)ethynyl)nicotinamido)-3-phenylpropan-2-yl acetate

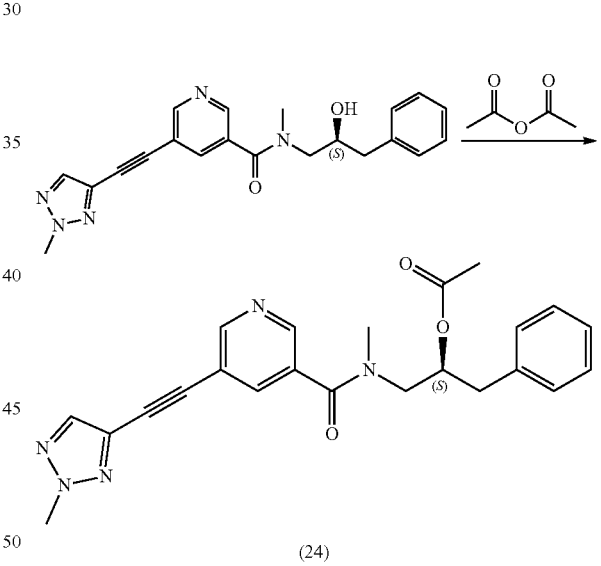

To a solution of (S)-N-(2-hydroxy-3-phenylpropyl)-N-methyl-5-((2-methyl-2H-1,2,3-triazol-4-yl)ethynyl)nicotinamide (Example #3) (1.50 g, 4.00 mmol) in 30 mL of dichloromethane was added triethylamine (1.89 mL, 13.6 mmol) and acetic anhydride (0.857 g, 8.39 mmol) in one portion at 20° C. under nitrogen. The mixture was stirred at 20° C. for 12 hours. After this time, the reaction was quenched with 50 mL of water. The organic and aqueous layers were separated, and the aqueous phase was extracted with dichloromethane (3×10 mL). The organic layers were combined, dried over magnesium sulfate, filtered and concentrated and the product was isolated by flash chromatography (20-50% EtOAc/hexanes) to provide the title compound (1.20 g, 2.86 mmol, 71.6% yield). $^1$H NMR (400 MHz, dimethylsulfoxide-d$_6$) δ 8.79 (s, 1H), 8.55 (d, J=1.75

Hz, 1H), 8.06 (s, 1H), 7.90 (s, 1H), 7.10-7.34 (m, 5H), 5.24-5.42 (m, 1H), 4.21 (s, 3H), 3.47-3.70 (m, 2H), 2.97 (s, 3H), 2.76-2.95 (m, 2H), 1.96 (s, 3H).

Example #25: (S)-1-(N-methyl-5-((2-methyl-2H-1,2,3-triazol-4-yl)ethynyl)nicotinamido)-3-phenylpropan-2-yl 2-aminoacetate, hydrochloric acid

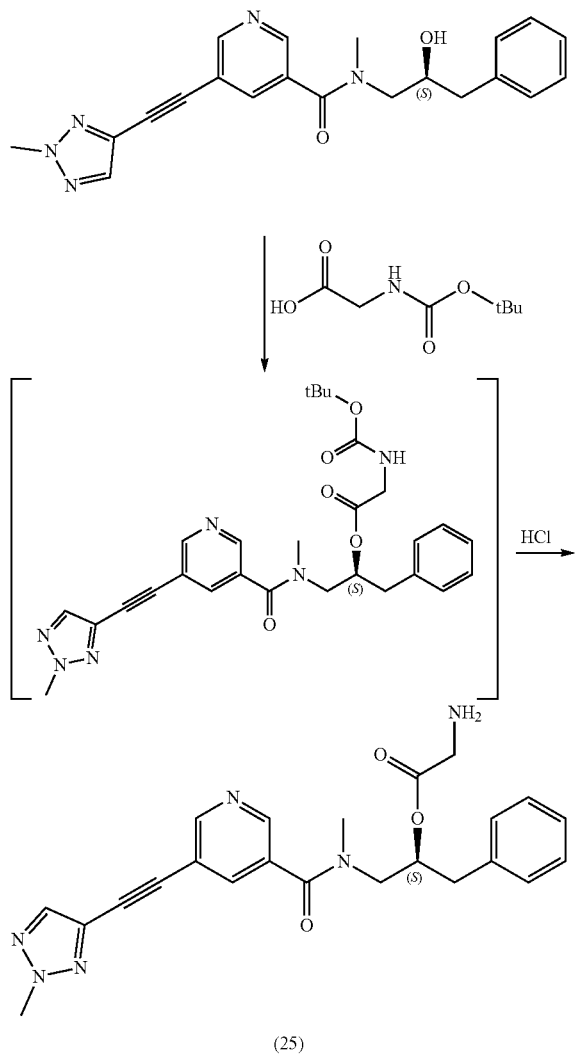

(25)

To a stirring solution of 2-((tert-butoxycarbonyl)amino) acetic acid (0.933 g, 5.33 mmol) in 5.0 mL of acetonitrile at 25° C. was added ((S)-N-(2-hydroxy-3-phenylpropyl)-N-methyl-5-((2-methyl-2H-1,2,3-triazol-4-yl)ethynyl)nicotinamide (Example #3) (2.00 g, 5.33 mmol). N,N'-dicyclohexylcarbodiimide (DCC) (1.37 g, 6.66 mmol) was added, followed by slow addition of a 5.3 mL acetonitrile solution of 4-dimethylaminopyridine (DMAP) (0.020 g, 0.16 mmol), keeping the reaction temperature between 20-25° C. The suspension was stirred for 2 hours at 25° C. After this time, the reaction mixture was filtered. The filtrate was concentrated and the resulting residue was purified by flash chromatography on silica gel (petroleum ether: ethyl acetate=4:1-1:1) to give the crude intermediate, (S)-1-(N-methyl-5-((2-methyl-2H-1,2,3-triazol-4-yl)ethynyl)nicotinamido)-3-phenylpropan-2-yl 2-((tert-butoxycarbonyl)-amino)acetate (2.2 g, 3.9 mmol, 74% yield), which was then dissolved in ethyl acetate (10 mL). Hydrogen chloride solution in ethyl acetate (4M, 20 mL, 80 mmol) was added to the solution, and the mixture was stirred for 1 hour at 25° C. The resulting suspension was dried under vacuum to provide the title compound (1.38 g, 2.85 mmol, 69.1% yield). $^1$H NMR (400 MHz, dimethylsulfoxide-$d_6$) δ 8.80 (s, 1H), 8.60 (br s, 1H), 8.47 (br s, 3H), 8.08 (s, 1H), 7.97 (br s, 1H), 7.16-7.35 (m, 5H), 5.25-5.57 (m, 1H), 4.63 (br s, 6H), 4.21 (s, 3H), 3.65-3.79 (m, 3H), 2.80-3.06 (m, 5H). tBu=tert-butyl.

Example #26: (S)-5-((1-(difluoromethyl)-5-methyl-1H-pyrazol-4-yl)ethynyl)-N-(2-hydroxy-3-phenylpropyl)-N-methylnicotinamide

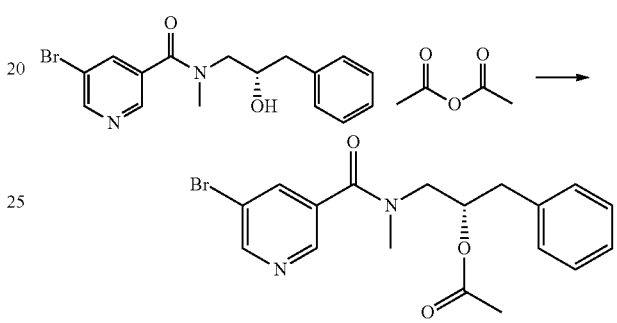

(S)-5-Bromo-N-(2-hydroxy-3-phenylpropyl)-N-methylnicotinamide (15 g, 43.0 mmol) (preparation #8), N,N-dimethylpyridin-4-amine (0.525 g, 4.30 mmol) and pyridine (17.37 mL, 215 mmol) were combined in dichloromethane (DCM) (150 mL) at about room temperature. Acetic anhydride (5.26 g, 51.5 mmol) was added dropwise. After about 4 h methyl tertbutyl ether (MTBE) (300 mL) and saturated copper sulfate (200 mL) were added, the organics were separated and washed with water (2×100 mL), dried (Na$_2$SO$_4$), filtered and concentrated in vacuo to provide (S)-1-(5-bromo-N-methylnicotinamido)-3-phenylpropan-2-yl acetate (16.8 g, 43.0 mmol, 100% yield) as an oil. LC/MS (Method aa) R$_t$=1.31 min.; MS m/z: 391.18, 393.16 (M+H)$^+$.

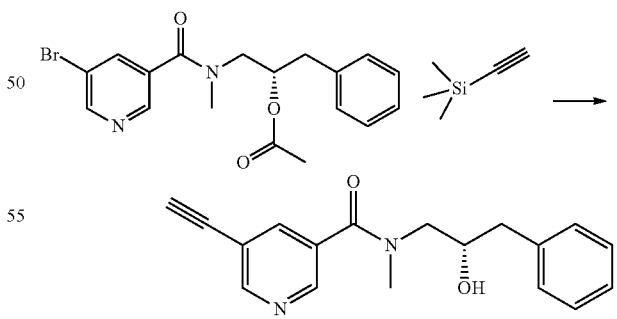

(S)-1-(5-bromo-N-methylnicotinamido)-3-phenylpropan-2-yl acetate (12.8 g, 32.7 mmol), ethynyltrimethylsilane (9.64 g, 98 mmol), diisopropylamine (9.33 mL, 65.4 mmol) were combined in dimethyl formamide (DMF) (60 mL) at about room temperature. 3 Å mole sieves were added. After about 2 h copper(I) iodide (0.062 g, 0.327 mmol) and bis(triphenylphosphine)palladium(II) chloride (0.230 g, 0.327 mmol) were added. The reaction mixture was warmed to about 80° C. After about 6 h, the mixture was cooled to room temperature. Satured NaHCO₃ (100 mL) and methyl tertbutyl ether (MTBE) (100 mL) and cysteine (2 g) were added and the reaction mixture was stirred at about room temperature. After about 4 h the mixture was filtered through celite, and the organics were separated, washed with brine (50 mL) and concentrated in vacuo. The crude alkyne was dissolved in methanol (MeOH) (100 mL) at about room temperature, and potassium carbonate (9.04 g, 65.4 mmol) was added. After about 4 h the mixture was partially concentrated in vacuo. Methyltertbutyl ether and ethyl acetate (MTBE/EtOAc) (1:1) (100 mL) and water (50 mL) were added. The organics were separated, concentrated in vacuo and purified by flash chromatography on silica gel (SiO₂) (EtOAc/Hep) to provide (S)-5-ethynyl-N-(2-hydroxy-3-phenylpropyl)-N-methylnicotinamide (6.8 g, 23.10 mmol, 70.6% yield) as an oil. HPLC method aa: R$_f$=0.94 min.; MS m/z: 295.3 (M+H)⁺.

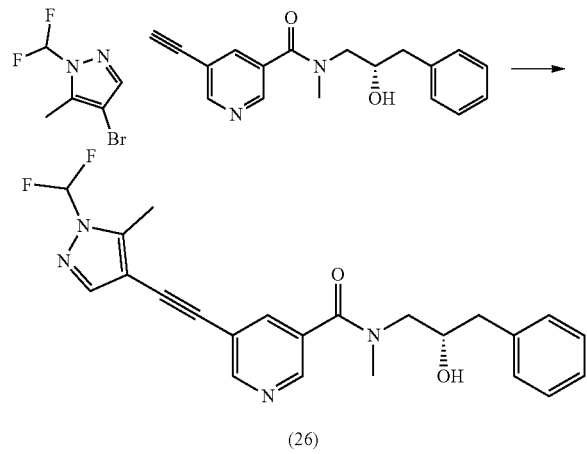

(26)

(S)-5-ethynyl-N-(2-hydroxy-3-phenylpropyl)-N-methylnicotinamide (6.8 g, 23.10 mmol), 4-bromo-1-(difluoromethyl)-5-methyl-1H-pyrazole (5.36 g, 25.4 mmol), diisopropylamine (6.59 mL, 46.2 mmol), copper(I) iodide (0.044 g, 0.231 mmol) and methanesulfonato(2-dicyclohexylphosphino-2',4',6'-tri-i-propyl-1,1'-biphenyl)(2'-amino-1,1'-biphenyl-2-yl)palladium(II) (0.196 g, 0.231 mmol) were combined in dimethyl formamide (DMF) (70 mL). The reaction mixture was sparged with nitrogen. After 10 min the rxn mixture was heated to 80° C. After 4 h cooled to room temperature. The mixture was diluted with methyltertbutyl ether and ethyl acetate (MTBE/EtOAc) (1:1) (20 mL) and water (20 mL), and cysteine (500 mg) was added. After stirring for 4 h, the organics were filtered and separated, washed with brine (10 mL), concentrated in vacuo and purified by flash chromatography on silica gel (SiO₂) (EtOAc/Hep). The product fractions were combined and concentrated in vacuo. The residue was dissolved in methyltertbutyl ether MTBE (20 mL) and heptane was added until the solution was cloudy. After stirring for 20 h, the solids were collected and dried in vacuo to provide (S)-5-((1-(difluoromethyl)-5-methyl-1H-pyrazol-4-yl)ethynyl)-N-(2-hydroxy-3-phenylpropyl)-N-methylnicotinamide (5.8 g, 13.66 mmol, 59.2% yield) as a white solid. HPLC method aa: R$_f$=1.28 min.; MS m/z: 425.3 (M+H)⁺. ¹H NMR (400 MHz, DMSO-d₆) δ 8.77-8.65 (m, 1H), 8.58-8.47 (m, 1H), 8.01-7.67 (m, 2H), 7.30-7.04 (m, 6H), 5.10-4.90 (m, 1H), 4.09-3.81 (m, 1H), 3.59-3.29 (m, 1H), 3.16-3.07 (m, 1H), 2.99-2.91 (m, 4H), 2.78-2.59 (m, 1H), 2.56-2.51 (m, 3H).

Assays and Activity Data

RIPK1 Binding Assay

Compounds were tested for their ability to displace a fluorescent probe from recombinant human RIPK1. Test compound RIPK1 binding (IC$_{50}$) data is provided in Table C.

Recombinant human RIPK1 (1-375) was prepared as described in Harris et al., *ACS Med. Chem. Letters* (2013) 4:1238-1243 (Supplementary Information), with the following exceptions: (i) instead of using the gene sequence from NM_003804.3, the gene was synthesized with codon optimization for BEV expression system, and (ii) the gene was cloned into the vector pFastBac1, not pDEST8.

A fluorescent probe containing an Oregon green fluorophore was synthesized from a compound known to bind to RIPK1.

The assay was performed in a buffer containing 50 mM N-2-Hydroxyethylpiperazine-N'-2-ethanesulfonic acid (HEPES) (pH 7.5), 10 mM MgCl₂, 1 mM ethylene diamine tetraacetic acid (EDTA), and 0.01% BRIJ-35 (Polyoxyethylene (23) lauryl ether). Test compounds were solvated in dimethyl sulfoxide (DMSO) at final concentrations 4-fold serially diluted from 100 to 0.000095 uM in technical duplicates into an empty 384 well plate. Recombinant RIPK1 (final concentration of 2.5 nM) was added to the wells and incubated with test compound for 1 hour at room temperature. A solution containing the fluorescent probe (final concentration 5 nM) and an LanthaScreen Tb-anti-GST antibody (Thermofisher Scientific; final concentration of 5 nM) was then added to each well, with the Tb-anti-GST antibody binding to the GST portion of the recombinant RIPK1 and providing the corresponding FRET pair to the fluorescent probe. The plate was incubated for 1 hour at room temperature and read on an Envision plate reader using a time resolved FRET protocol. Data was normalized and analyzed using Studies from Dotmatics.

U937 TNF/zVAD Cytotoxicity Cell Assay

Compounds were tested for their ability to prevent TNF induced necroptosis in U937 cells. Treatment with TNF and the caspase inhibitor zVAD-FMK results in the activation and phosphorylation of RIPK1 and subsequent phosphorylation of RIPK3 and MLKL (Mixed Lineage Kinase Domain Like Pseudokinase), leading to induction of necroptotic cell death that is measured as a reduction in cell viability. U937 TNF/zVAD induced cytotoxicity (IC$_{50}$) data, indicative of a test compound's ability to inhibit RIPK1, is provided in Table C. Similar U937 assay protocols have been previously described; see, e.g., Harris et al., *ACS Med. Chem. Letters* (2013) 4:1238-1243 and Supplementary Information.

Test compounds were solvated in dimethyl sulfoxide (DMSO) and 3-fold serially diluted from 10 uM to 0.0005 uM with technical duplicates into an empty 384 well plate. U937 cells were resuspended at a concentration of 500,000 cells/mL in fresh RPMI (Roswell Park Memorial Institute) 1640 growth medium containing 10% heat inactivated fetal bovine serum (FB1S) and seeded into a 384 well plate containing compounds and incubated for 1 hour at 37° C. Following incubation, the cells were challenged with TNFα (final concentration of 10 ng/mL) and Z-VAD FMK (N-Benzyloxycarbonyl-Val-Ala-Asp(O-Me) fluoromethyl ketone; final concentration of 20 μM) for 16-20 hours at 37° C. Following the incubation with TNFα/Z-VAD, cells were lysed with Cell Titer-Glo and incubated for 5-10 minutes.

The plate was then read on an Envision plate reader. Data was normalized and analyzed with Studies from Dotmatics.

TABLE C

| Example | RIPK1 Binding IC$_{50}$ (μM) | U937 TNF/zVAD Induced Cytotoxicity IC$_{50}$ (μM) |
|---|---|---|
| 1 | 0.011 | 0.034 |
| 2 | 0.004 | 0.011 |
| 3 | 0.036 | 0.196 |
| 4 | 0.030 | 0.199 |
| 5 | 0.014 | 0.049 |
| 6 | 0.003 | 0.006 |
| 7 | 0.007 | 0.009 |
| 8 | 0.006 | 0.013 |
| 9 | 0.018 | 0.029 |
| 10 | 0.043 | 0.380 |
| 11 | 0.002 | 0.005 |
| 12 | 0.013 | 0.020 |
| 13 | 0.095 | 0.382 |
| 14 | 0.008 | 0.018 |
| 15 | 25 | — |
| 16 | 0.515 | 2.580 |
| 17 | 0.032 | 0.146 |
| 26 | 0.0018 | 0.003 |

Selectivity Data

Compounds were tested in a screening platform for their ability to bind to hundreds of human kinases and disease-relevant mutant variants thereof. Binding affinities are provided in Table D.

The Method.

The screening method uses an immobilized ligand on a solid support, a DNA-tagged kinase, and a test compound. Test compounds that bind the kinase active site and directly (sterically) or indirectly (allosterically) prevent kinase binding to an immobilized ligand on a solid support will reduce the amount of kinase captured on the solid support. Conversely, test compound that do not bind the kinase have no effect on the amount of kinase captured on the solid support. Screening "hits" are identified by measuring the amount of kinase captured in test compound versus control samples by using a quantitative, precise and ultra-sensitive qPCR method that detects the DNA label associated with the kinase. In a similar manner, dissociation constants (K$_d$) for test compound-kinase interactions are calculated by measuring the amount of kinase captured on the solid support as a function of the test compound concentration.

Kinase Assays.

For most assays, kinase-tagged T7 phage strains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 m) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Percent Control calculation.

The compounds were screened at 100 nM concentration, and results for the binding interactions are shown below in Table D as percent control, where lower numbers indicate stronger hits. The calculation for percent control is shown below. The negative control was DMSO (100% control), and a control compound was used as positive control (0% control).

$$\left(\frac{\text{test compound signal} - \text{positive control signal}}{\text{negative control signal} - \text{positive control signal}}\right) \times 100$$

TABLE D

| DiscoveRx Gene Symbol | Compound #2 Percent Control at 100 nM Compound Concentration | Compound #19 Percent Control at 100 nM Compound Concentration |
|---|---|---|
| AAK1 | 96 | 100 |
| ABL1(E255K)-phosphorylated | 86 | 91 |
| ABL1(F317I)-nonphosphorylated | 100 | 100 |
| ABL1(F317I)-phosphorylated | 100 | 98 |
| ABL1(F317L)-nonphosphorylated | 100 | 100 |
| ABL1(F317L)-phosphorylated | 82 | 88 |
| ABL1(H396P)-nonphosphorylated | 88 | 96 |
| ABL1(H396P)-phosphorylated | 94 | 93 |
| ABL1(M351T)-phosphorylated | 86 | 97 |
| ABL1(Q252H)-nonphosphorylated | 92 | 100 |
| ABL1(Q252H)-phosphorylated | 99 | 99 |
| ABL1(T315I)-nonphosphorylated | 100 | 97 |
| ABL1(T315I)-phosphorylated | 80 | 92 |
| ABL1(Y253F)-pho sphorylated | 100 | 100 |
| ABL1-nonphosphorylated | 72 | 96 |
| ABL1-phosphorylated | 79 | 78 |
| ABL2 | 100 | 98 |
| ACVR1 | 100 | 100 |
| ACVR1B | 100 | 100 |
| ACVR2A | 94 | 100 |
| ACVR2B | 91 | 99 |
| ACVRL1 | 100 | 100 |
| ADCK3 | 100 | 100 |
| ADCK4 | 100 | 100 |
| AKT1 | 100 | 100 |
| AKT2 | 99 | 90 |
| AKT3 | 100 | 100 |
| ALK | 100 | 100 |
| ALK(C1156Y) | 100 | 100 |
| ALK(L1196M) | 100 | 100 |
| AMPK-alpha1 | 100 | 100 |
| AMPK-alpha2 | 89 | 100 |
| ANKK1 | 100 | 100 |
| ARK5 | 100 | 100 |
| ASK1 | 88 | 100 |
| ASK2 | 100 | 98 |
| AURKA | 100 | 100 |
| AURKB | 100 | 90 |
| AURKC | 100 | 100 |
| AXL | 100 | 96 |
| BIKE | 100 | 100 |
| BLK | 85 | 96 |

TABLE D-continued

| DiscoveRx Gene Symbol | Compound #2 Percent Control at 100 nM Compound Concentration | Compound #19 Percent Control at 100 nM Compound Concentration |
|---|---|---|
| BMPR1A | 86 | 94 |
| BMPR1B | 98 | 99 |
| BMPR2 | 100 | 89 |
| BMX | 100 | 100 |
| BRAF | 100 | 100 |
| BRAF(V600E) | 97 | 97 |
| BRK | 100 | 100 |
| BRSK1 | 99 | 99 |
| BRSK2 | 96 | 95 |
| BTK | 100 | 96 |
| BUB1 | 93 | 85 |
| CAMK1 | 100 | 62 |
| CAMK1B | 82 | 83 |
| CAMK1D | 100 | 74 |
| CAMK1G | 93 | 100 |
| CAMK2A | 97 | 100 |
| CAMK2B | 100 | 92 |
| CAMK2D | 100 | 100 |
| CAMK2G | 94 | 100 |
| CAMK4 | 100 | 100 |
| CAMKK1 | 100 | 100 |
| CAMKK2 | 99 | 100 |
| CASK | 99 | 94 |
| CDC2L1 | 100 | 100 |
| CDC2L2 | 100 | 100 |
| CDC2L5 | 100 | 100 |
| CDK11 | 4.8 | 92 |
| CDK2 | 100 | 100 |
| CDK3 | 100 | 100 |
| CDK4 | 100 | 93 |
| CDK4-cyclinD1 | 100 | 97 |
| CDK4-cyclinD3 | 100 | 100 |
| CDK5 | 100 | 100 |
| CDK7 | 100 | 100 |
| CDK8 | 10 | 98 |
| CDK9 | 100 | 100 |
| CDKL1 | 100 | 100 |
| CDKL2 | 100 | 95 |
| CDKL3 | 100 | 97 |
| CDKL5 | 93 | 86 |
| CHEK1 | 100 | 100 |
| CHEK2 | 100 | 100 |
| CIT | 98 | 95 |
| CLK1 | 100 | 100 |
| CLK2 | 95 | 100 |
| CLK3 | 97 | 93 |
| CLK4 | 92 | 100 |
| CSF1R | 100 | 100 |
| CSF1R-autoinhibited | 99 | 99 |
| CSK | 98 | 93 |
| CSNK1A1 | 100 | 92 |
| CSNK1A1L | 100 | 97 |
| CSNK1D | 100 | 100 |
| CSNK1E | 67 | 74 |
| CSNK1G1 | 100 | 100 |
| CSNK1G2 | 100 | 95 |
| CSNK1G3 | 99 | 100 |
| CSNK2A1 | 98 | 98 |
| CSNK2A2 | 100 | 100 |
| CTK | 100 | 90 |
| DAPK1 | 100 | 100 |
| DAPK2 | 100 | 90 |
| DAPK3 | 100 | 97 |
| DCAMKL1 | 100 | 100 |
| DCAMKL2 | 100 | 100 |
| DCAMKL3 | 100 | 100 |
| DDR1 | 100 | 100 |
| DDR2 | 100 | 100 |
| DLK | 100 | 100 |
| DMPK | 100 | 100 |
| DMPK2 | 97 | 96 |
| DRAK1 | 95 | 100 |
| DRAK2 | 100 | 100 |
| DYRK1A | 90 | 85 |
| DYRK1B | 97 | 79 |
| DYRK2 | 100 | 97 |
| EGFR | 93 | 100 |
| EGFR(E746-A750del) | 100 | 94 |
| EGFR(G719C) | 100 | 77 |
| EGFR(G719S) | 100 | 72 |
| EGFR(L747-E749del, A750P) | 100 | 84 |
| EGFR(L747-S752del, P753S) | 100 | 97 |
| EGFR(L747-T751del,Sins) | 100 | 79 |
| EGFR(L858R) | 100 | 94 |
| EGFR(L858R,T790M) | 83 | 94 |
| EGFR(L861Q) | 100 | 86 |
| EGFR(S752-I759del) | 100 | 100 |
| EGFR(T790M) | 100 | 100 |
| EIF2AK1 | 100 | 96 |
| EPHA1 | 100 | 100 |
| EPHA2 | 100 | 100 |
| EPHA3 | 100 | 100 |
| EPHA4 | 97 | 96 |
| EPHA5 | 100 | 100 |
| EPHA6 | 100 | 100 |
| EPHA7 | 97 | 96 |
| EPHA8 | 99 | 100 |
| EPHB1 | 100 | 100 |
| EPHB2 | 100 | 100 |
| EPHB3 | 100 | 100 |
| EPHB4 | 100 | 100 |
| EPHB6 | 100 | 100 |
| ERBB2 | 70 | 65 |
| ERBB3 | 100 | 100 |
| ERBB4 | 94 | 93 |
| ERK1 | 97 | 95 |
| ERK2 | 100 | 100 |
| ERK3 | 100 | 100 |
| ERK4 | 100 | 100 |
| ERK5 | 100 | 100 |
| ERK8 | 100 | 100 |
| ERN1 | 100 | 93 |
| FAK | 100 | 100 |
| FER | 100 | 96 |
| FES | 100 | 100 |
| FGFR1 | 94 | 95 |
| FGFR2 | 100 | 100 |
| FGFR3 | 100 | 100 |
| FGFR3(G697C) | 100 | 100 |
| FGFR4 | 100 | 100 |
| FGR | 100 | 99 |
| FLT1 | 100 | 100 |
| FLT3 | 100 | 100 |
| FLT3(D835H) | 100 | 100 |
| FLT3(D835V) | 100 | 100 |
| FLT3(D835Y) | 100 | 100 |
| FLT3(ITD) | 100 | 100 |
| FLT3(ITD,D835V) | 100 | 100 |
| FLT3(ITD,F691L) | 98 | 97 |
| FLT3(K663Q) | 100 | 100 |
| FLT3(N841I) | 99 | 96 |
| FLT3(R834Q) | 100 | 100 |
| FLT3-autoinhibited | 95 | 96 |
| FLT4 | 100 | 100 |
| FRK | 100 | 100 |
| FYN | 100 | 100 |
| GAK | 100 | 100 |
| GCN2(Kin.Dom.2,S808G) | 95 | 97 |
| GRK1 | 100 | 98 |
| GRK2 | 96 | 79 |
| GRK3 | 82 | 81 |
| GRK4 | 100 | 100 |
| GRK7 | 100 | 100 |
| GSK3A | 100 | 100 |
| GSK3B | 100 | 98 |
| HASPIN | 86 | 83 |
| HCK | 100 | 100 |
| HIPK1 | 72 | 82 |

TABLE D-continued

| DiscoveRx Gene Symbol | Compound #2 Percent Control at 100 nM Compound Concentration | Compound #19 Percent Control at 100 nM Compound Concentration |
|---|---|---|
| HIPK2 | 99 | 79 |
| HIPK3 | 100 | 88 |
| HIPK4 | 100 | 100 |
| HPK1 | 78 | 92 |
| HUNK | 82 | 96 |
| ICK | 100 | 93 |
| IGF1R | 100 | 98 |
| IKK-alpha | 100 | 99 |
| IKK-beta | 96 | 96 |
| IKK-epsilon | 100 | 94 |
| INSR | 100 | 100 |
| INSRR | 100 | 100 |
| IRAK1 | 91 | 86 |
| IRAK3 | 96 | 92 |
| IRAK4 | 91 | 83 |
| ITK | 99 | 100 |
| JAK1(JH1domain-catalytic) | 100 | 100 |
| JAK1(JH2domain-pseudokinase) | 93 | 86 |
| JAK2(JH1domain-catalytic) | 100 | 100 |
| JAK3(JH1domain-catalytic) | 100 | 100 |
| JNK1 | 92 | 87 |
| JNK2 | 91 | 92 |
| JNK3 | 83 | 86 |
| KIT | 100 | 99 |
| KIT(A829P) | 100 | 99 |
| KIT(D816H) | 100 | 98 |
| KIT(D816V) | 100 | 100 |
| KIT(L576P) | 100 | 98 |
| KIT(V559D) | 100 | 96 |
| KIT(V559D,T670I) | 97 | 100 |
| KIT(V559D,V654A) | 94 | 100 |
| KIT-autoinhibited | 94 | 94 |
| LATS1 | 100 | 88 |
| LATS2 | 98 | 100 |
| LCK | 100 | 95 |
| LIMK1 | 100 | 100 |
| LIMK2 | 95 | 93 |
| LKB1 | 70 | 79 |
| LOK | 100 | 100 |
| LRRK2 | 100 | 81 |
| LRRK2(G2019S) | 100 | 93 |
| LTK | 100 | 100 |
| LYN | 71 | 80 |
| LZK | 99 | 99 |
| MAK | 100 | 100 |
| MAP3K1 | 100 | 100 |
| MAP3K15 | 100 | 97 |
| MAP3K2 | 99 | 95 |
| MAP3K3 | 96 | 92 |
| MAP3K4 | 100 | 100 |
| MAP4K2 | 88 | 83 |
| MAP4K3 | 100 | 100 |
| MAP4K4 | 92 | 95 |
| MAP4K5 | 87 | 95 |
| MAPKAPK2 | 100 | 100 |
| MAPKAPK5 | 94 | 96 |
| MARK1 | 100 | 96 |
| MARK2 | 96 | 100 |
| MARK3 | 98 | 97 |
| MARK4 | 91 | 94 |
| MAST1 | 100 | 97 |
| MEK1 | 98 | 99 |
| MEK2 | 99 | 98 |
| MEK3 | 94 | 79 |
| MEK4 | 100 | 100 |
| MEK5 | 89 | 87 |
| MEK6 | 100 | 96 |
| MELK | 77 | 83 |
| MERTK | 100 | 100 |
| MET | 100 | 100 |
| MET(M1250T) | 100 | 100 |
| MET(Y1235D) | 98 | 99 |
| MINK | 100 | 100 |
| MKK7 | 98 | 96 |
| MKNK1 | 96 | 91 |
| MKNK2 | 82 | 79 |
| MLCK | 100 | 100 |
| MLK1 | 100 | 96 |
| MLK2 | 66 | 69 |
| MLK3 | 95 | 89 |
| MRCKA | 100 | 100 |
| MRCKB | 95 | 100 |
| MST1 | 100 | 100 |
| MST1R | 98 | 92 |
| MST2 | 100 | 99 |
| MST3 | 100 | 100 |
| MST4 | 97 | 84 |
| MTOR | 73 | 67 |
| MUSK | 100 | 100 |
| MYLK | 87 | 86 |
| MYLK2 | 100 | 96 |
| MYLK4 | 99 | 100 |
| MYO3A | 99 | 93 |
| MYO3B | 95 | 79 |
| NDR1 | 100 | 100 |
| NDR2 | 94 | 84 |
| NEK1 | 100 | 100 |
| NEK10 | 91 | 100 |
| NEK11 | 100 | 95 |
| NEK2 | 100 | 100 |
| NEK3 | 96 | 96 |
| NEK4 | 100 | 100 |
| NEK5 | 100 | 94 |
| NEK6 | 100 | 100 |
| NEK7 | 100 | 99 |
| NEK9 | 100 | 100 |
| NIK | 84 | 88 |
| NIM1 | 89 | 89 |
| NLK | 100 | 100 |
| OSR1 | 88 | 89 |
| p38-alpha | 100 | 100 |
| p38-beta | 100 | 97 |
| p38-delta | 100 | 100 |
| p38-gamma | 100 | 88 |
| PAK1 | 100 | 100 |
| PAK2 | 97 | 92 |
| PAK3 | 71 | 100 |
| PAK4 | 98 | 98 |
| PAK6 | 85 | 80 |
| PAK7 | 100 | 100 |
| PCTK1 | 91 | 84 |
| PCTK2 | 100 | 100 |
| PCTK3 | 100 | 100 |
| PDGFRA | 73 | 85 |
| PDGFRB | 100 | 100 |
| PDPK1 | 99 | 100 |
| PFCDPK1(P.falciparum) | 95 | 96 |
| PFPK5(P.falciparum) | 90 | 100 |
| PFTAIRE2 | 100 | 100 |
| PFTK1 | 100 | 100 |
| PHKG1 | 100 | 100 |
| PHKG2 | 100 | 100 |
| PIK3C2B | 100 | 100 |
| PIK3C2G | 85 | 78 |
| PIK3CA | 100 | 100 |
| PIK3CA(C420R) | 83 | 86 |
| PIK3CA(E542K) | 89 | 81 |
| PIK3CA(E545A) | 89 | 94 |
| PIK3CA(E545K) | 91 | 85 |
| PIK3CA(H1047L) | 85 | 71 |
| PIK3CA(H1047Y) | 71 | 72 |
| PIK3CA(I800L) | 96 | 87 |
| PIK3CA(M1043I) | 92 | 85 |
| PIK3CA(Q546K) | 96 | 88 |
| PIK3CB | 100 | 95 |
| PIK3CD | 99 | 85 |
| PIK3CG | 100 | 100 |
| PIK4CB | 100 | 98 |

TABLE D-continued

| DiscoveRx Gene Symbol | Compound #2 Percent Control at 100 nM Compound Concentration | Compound #19 Percent Control at 100 nM Compound Concentration |
|---|---|---|
| PIKFYVE | 57 | 57 |
| PIM1 | 98 | 100 |
| PIM2 | 95 | 100 |
| PIM3 | 100 | 100 |
| PIP5K1A | 100 | 92 |
| PIP5K1C | 100 | 85 |
| PIP5K2B | 100 | 95 |
| PIP5K2C | 63 | 74 |
| PKAC-alpha | 94 | 94 |
| PKAC-beta | 92 | 100 |
| PKMYT1 | 99 | 100 |
| PKN1 | 91 | 100 |
| PKN2 | 97 | 100 |
| PKNB(M.tuberculosis) | 100 | 100 |
| PLK1 | 87 | 87 |
| PLK2 | 98 | 91 |
| PLK3 | 97 | 92 |
| PLK4 | 100 | 100 |
| PRKCD | 98 | 94 |
| PRKCE | 72 | 68 |
| PRKCH | 100 | 91 |
| PRKCI | 96 | 92 |
| PRKCQ | 94 | 98 |
| PRKD1 | 100 | 100 |
| PRKD2 | 79 | 100 |
| PRKD3 | 100 | 100 |
| PRKG1 | 92 | 100 |
| PRKG2 | 100 | 97 |
| PRKR | 100 | 97 |
| PRKX | 100 | 100 |
| PRP4 | 89 | 82 |
| PYK2 | 100 | 100 |
| QSK | 88 | 85 |
| RAF1 | 100 | 100 |
| RET | 100 | 100 |
| RET(M918T) | 100 | 100 |
| RET(V804L) | 100 | 100 |
| RET(V804M) | 100 | 100 |
| RIOK1 | 100 | 100 |
| RIOK2 | 95 | 95 |
| RIOK3 | 100 | 100 |
| RIPK1 | 26 | 91 |
| RIPK2 | 100 | 100 |
| RIPK4 | 100 | 100 |
| RIPK5 | 100 | 96 |
| ROCK1 | 100 | 100 |
| ROCK2 | 100 | 100 |
| ROS1 | 100 | 91 |
| RPS6KA4(Kin.Dom.1-N-terminal) | 97 | 100 |
| RPS6KA4(Kin.Dom.2-C-terminal) | 97 | 100 |
| RPS6KA5(Kin.Dom.1-N-terminal) | 91 | 100 |
| RPS6KA5(Kin.Dom.2-C-terminal) | 95 | 90 |
| RSK1(Kin.Dom.1-N-terminal) | 96 | 100 |
| RSK1(Kin.Dom.2-C-terminal) | 100 | 100 |
| RSK2(Kin.Dom.1-N-terminal) | 100 | 94 |
| RSK2(Kin.Dom.2-C-terminal) | 100 | 100 |
| RSK3(Kin.Dom.1-N-terminal) | 97 | 100 |
| RSK3(Kin.Dom.2-C-terminal) | 100 | 100 |
| RSK4(Kin.Dom.1-N-terminal) | 100 | 93 |
| RSK4(Kin.Dom.2-C-terminal) | 100 | 100 |
| S6K1 | 95 | 95 |
| SBK1 | 97 | 95 |
| SGK | 96 | 90 |
| SgK110 | 81 | 77 |
| SGK2 | 100 | 93 |
| SGK3 | 100 | 100 |
| SIK | 100 | 100 |
| SIK2 | 89 | 96 |
| SLK | 99 | 97 |
| SNARK | 99 | 99 |
| SNRK | 100 | 100 |
| SRC | 97 | 100 |
| SRMS | 100 | 96 |
| SRPK1 | 100 | 100 |
| SRPK2 | 93 | 100 |
| SRPK3 | 90 | 100 |
| STK16 | 98 | 92 |
| STK33 | 88 | 100 |
| STK35 | 99 | 100 |
| STK36 | 100 | 100 |
| STK39 | 100 | 100 |
| SYK | 97 | 93 |
| TAK1 | 97 | 95 |
| TAOK1 | 100 | 100 |
| TAOK2 | 84 | 77 |
| TAOK3 | 92 | 85 |
| TBK1 | 79 | 84 |
| TEC | 99 | 93 |
| TESK1 | 100 | 100 |
| TGFBR1 | 100 | 100 |
| TGFBR2 | 100 | 100 |
| TIE1 | 100 | 100 |
| TIE2 | 100 | 88 |
| TLK1 | 100 | 100 |
| TLK2 | 100 | 100 |
| TNIK | 100 | 100 |
| TNK1 | 100 | 100 |
| TNK2 | 100 | 100 |
| TNNI3K | 100 | 100 |
| TRKA | 100 | 81 |
| TRKB | 100 | 94 |
| TRKC | 100 | 68 |
| TRPM6 | 99 | 95 |
| TSSK1B | 88 | 76 |
| TSSK3 | 82 | 100 |
| TTK | 100 | 82 |
| TXK | 100 | 100 |
| TYK2(JH1domain-catalytic) | 100 | 100 |
| TYK2(JH2domain-pseudokinase) | 100 | 90 |
| TYRO3 | 99 | 100 |
| ULK1 | 100 | 100 |
| ULK2 | 100 | 94 |
| ULK3 | 97 | 96 |
| VEGFR2 | 96 | 97 |
| VPS34 | 87 | 90 |
| VRK2 | 91 | 95 |
| WEE1 | 92 | 100 |
| WEE2 | 100 | 100 |
| WNK1 | 93 | 94 |
| WNK2 | 100 | 100 |
| WNK3 | 100 | 100 |
| WNK4 | 84 | 81 |
| YANK1 | 100 | 100 |
| YANK2 | 100 | 95 |
| YANK3 | 67 | 54 |
| YES | 100 | 100 |
| YSK1 | 100 | 97 |
| YSK4 | 99 | 90 |
| ZAK | 100 | 100 |
| ZAP70 | 98 | 98 |

Based on the binding affinities in Table D, a selectivity score (S-score) was calculated for each compound as a quantitative measure of compound selectivity. The S-score is calculated by dividing the number of kinases that a compound binds to by the total number of distinct kinases tested, excluding mutant variants. The selectivity score value can be calculated using % Ctrl as a potency threshold, as shown below, and provides a quantitative method of describing compound selectivity to facilitate comparison of different compounds.

S(10)=(number of non-mutant kinases with % Ctrl<35)/(number of non-mutant kinases tested).

S(35)=(number of non-mutant kinases with % Ctrl<10)/(number of non-mutant kinases tested).

S(35)=(number of non-mutant kinases with % Ctrl<1)/(number of non-mutant kinases tested).

Results are shown in Table E.

TABLE E

| Compound | Selectivity Score Type | Number of Hits | Number of Non-Mutant Kinases | Screening Concentration (nM) | Selectivity Score |
|---|---|---|---|---|---|
| Compound #2 | S(35) | 3 | 403 | 100 | 0.007 |
| Compound #2 | S(10) | 1 | 403 | 100 | 0.002 |
| Compound #2 | S(1) | 0 | 403 | 100 | 0 |
| Compound #19 | S(35) | 0 | 403 | 100 | 0 |
| Compound #19 | S(10) | 0 | 403 | 100 | 0 |
| Compound #19 | S(1) | 0 | 403 | 100 | 0 |

Prodrug Bioconversion

Phosphatase enzymes are ambiguously expressed with unique tissue specific isoforms and are key catalysts in the conversion of phosphate-containing prodrugs. To determine if exemplary phosphate prodrug compounds of the invention are enzymatically converted to the parent molecule across relevant species, the prodrug compounds were incubated with intestinal S9 cell fractions obtained from mouse, rat, dog, monkey, and human.

Phosphate prodrugs were incubated (1 μM) for up to 2 hours in Tris-Cl buffer (pH 7.4) containing 3 mM magnesium chloride, intestinal S9 protein (0.01 and 25 mg/mL (ms, rat, hu, Table F) from mouse, rat, dog, monkey or human. Incubations were conducted in the absence and presence of 1 mM sodium orthovanadate, a phosphatase inhibitor. Prodrug depletion and parent formation were monitored by LC-MS/MS and normalized to internal standard as the analyte peak area ratio.

TABLE F

In vitro intrinsic clearance as measured by prodrug disappearance in intestinal S9 cell fractions.

| | Clint (μL/min/mg intestinal S9 protein) (0.25 mg/mL) | | | Clint (μL/min/mg intestinal S9 protein) (0.01 mg/mL) | | |
|---|---|---|---|---|---|---|
| Example | Human | Rat | Mouse | Human | Rat | Mouse |
| 19 | 296 | 42.4 | 54.7 | 1608.5 | <137** | 116.8 |
| 21 | 592.9 | 901.6 | >4166.5* | 815.9 | 2599.5 | 11160 |
| 23 | 243.4 | 36.7 | 23.3 | 1180.2 | <137** | <137** |
| 25 | 410 | 393.8 | >1640.7* | 378.1 | 1087.6 | 6821.9 |

*Values were qualified because Clint was generated from a 2 time point curve
**The qualified value was estimated based on 15% remaining after 2 hour incubation

TABLE G

In vitro intrinsic clearance as measured by Example #19 disappearance in intestinal S9 cell fractions.
Clint (μL/min/mg intestinal S9 protein)
(0.25 mg/mL)

| Experiment | Human | Monkey | Dog | Rat | Mouse |
|---|---|---|---|---|---|
| 1 | 246 | 87.5 | 331 | 25.6 | 43.1 |
| 2 | 228 | 60.3 | 387 | 16.9 | 74.6 |
| 3 | 235 | 60.7 | 397 | 50.6 | 42.2 |
| Mean | 236.3 | 69.5 | 371.7 | 31 | 53.3 |
| SD | 9.1 | 15.6 | 35.6 | 17.5 | 18.5 |

Values are presented as Clint in units of μL/min/mg intestinal S9 protein.

TABLE H

In vitro intrinsic clearance as measured by Example #21 disappearance in intestinal S9 cell fractions.
Clint (μL/min/mg intestinal S9 protein)
0.25 mg/mL)

| Experiment | Human | Monkey | Dog | Rat | Mouse |
|---|---|---|---|---|---|
| 1 | 391 | 89.6 | 5.62 | 396 | >480* |
| 2 | 400 | 91.3 | 16.1 | 719 | >480* |
| 3 | 355 | 90.7 | 14.3 | 750 | >480* |
| Mean | 382 | 90.5 | 12.0 | 622 | >480* |
| SD | 24.3 | 0.861 | 5.62 | 196 | |

Values are presented as Clint in units of μL/min/mg intestinal S9 protein.
*-Values were qualified because CLint was generated from a 2 time-point curve

TABLE I

In vitro intrinsic clearance as measured by Example #23 disappearance in intestinal S9 cell fractions.
Clint (μL/min/mg intestinal S9 protein)
0.25 mg/mL)

| Experiment | Human | Monkey | Dog | Rat | Mouse |
|---|---|---|---|---|---|
| 1 | 199 | 55.4 | 354 | 29.1 | 26.2 |
| 2 | 241 | 47.7 | 369 | 33.8 | 34.3 |
| 3 | 203 | 48.1 | 345 | 28.2 | 31.3 |
| Mean | 214 | 50.4 | 356 | 30.4 | 30.6 |
| SD | 23.3 | 4.35 | 12.4 | 3.04 | 4.07 |

Values are presented as Clint in units of μL/min/mg intestinal S9 protein.
*-Values were qualified because CLint was generated from a 2 time-point curve

TABLE J

In vitro intrinsic clearance as measured by Example #25 disappearance in intestinal S9 cell fractions.
Clint (μL/min/mg intestinal S9 protein)
0.25 mg/mL)

| Experiment | Human | Monkey | Dog | Rat | Mouse |
|---|---|---|---|---|---|
| 1 | 272 | 38.1 | 10.2 | 217 | >480* |
| 2 | 294 | 49.0 | 14.4 | 318 | >480* |
| 3 | 293 | 40.7 | 11.5 | 299 | >480* |
| Mean | 286 | 42.6 | 12.0 | 278 | >480* |
| SD | 12.7 | 5.66 | 2.14 | 53.8 | |

Values are presented as Clint in units of μL/min/mg intestinal S9 protein.
*-Values were qualified because CLint was generated from a 2 time-point curve

OTHER EMBODIMENTS

This application refers to various issued patents, published patent applications, journal articles, and other publications, each of which is incorporated herein by reference.

The foregoing has been described of certain non-limiting embodiments of the present disclosure. Those of ordinary skill in the art will appreciate that various changes and modifications to this description may be made without departing from the spirit or scope of the present disclosure, as defined in the following claims.

What is claimed is:

1. A compound represented by the following structure:

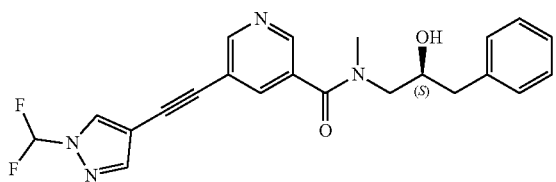

or a pharmaceutically acceptable salt thereof.

2. The compound of claim 1 represented by the following structure:

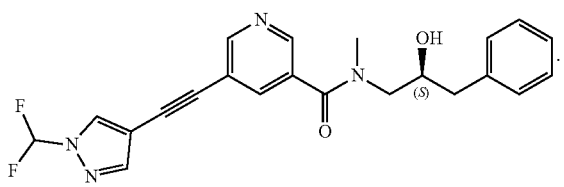

3. A compound represented by the following structure:

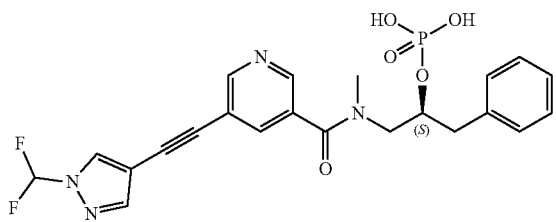

or a pharmaceutically acceptable salt thereof.

4. The compound of claim 3 represented by the following structure:

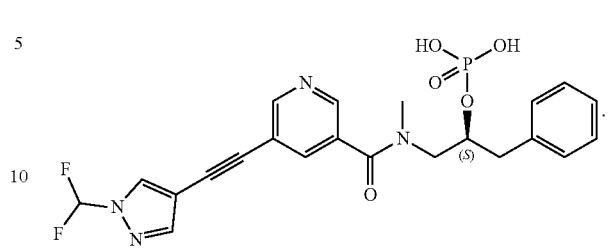

5. A pharmaceutical composition comprising the compound of claim 1, or a pharmaceutically acceptable salt thereof.

6. A pharmaceutical composition comprising the compound of claim 2.

7. A pharmaceutical composition comprising the compound of claim 3, or a pharmaceutically acceptable salt thereof.

8. A pharmaceutical composition comprising the compound of claim 4.

* * * * *